United States Patent
Gros et al.

(10) Patent No.: US 10,544,392 B2
(45) Date of Patent: Jan. 28, 2020

(54) METHODS OF ISOLATING T CELLS AND T CELL RECEPTORS HAVING ANTIGENIC SPECIFICITY FOR A CANCER-SPECIFIC MUTATION FROM PERIPHERAL BLOOD

(71) Applicant: The United States of America, as represented by the Secretary, Department of Health and Human Services, Bethesda, MD (US)

(72) Inventors: Alena Gros, Washington, DC (US); Steven A. Rosenberg, Potomac, MD (US)

(73) Assignee: The United States of America, as represented by the Secretary, Department of Health and Human Services, Bethesda, MD (US)

(*) Notice: Subject to any disclaimer, the term of this patent is extended or adjusted under 35 U.S.C. 154(b) by 0 days.

(21) Appl. No.: 15/567,157

(22) PCT Filed: Apr. 29, 2016

(86) PCT No.: PCT/US2016/030137
§ 371 (c)(1),
(2) Date: Oct. 17, 2017

(87) PCT Pub. No.: WO2016/179006
PCT Pub. Date: Nov. 10, 2016

(65) Prior Publication Data
US 2018/0148690 A1    May 31, 2018

Related U.S. Application Data

(60) Provisional application No. 62/155,830, filed on May 1, 2015.

(51) Int. Cl.
*C12N 5/0783* (2010.01)
*A61P 35/00* (2006.01)
*A61K 38/17* (2006.01)
*C12N 15/63* (2006.01)

(52) U.S. Cl.
CPC ........ *C12N 5/0636* (2013.01); *A61K 38/1703* (2013.01); *A61P 35/00* (2018.01); *C12N 15/63* (2013.01)

(58) Field of Classification Search
None
See application file for complete search history.

(56) References Cited

U.S. PATENT DOCUMENTS

| | | |
|---|---|---|
| 8,034,334 B2 | 10/2011 | Dudley et al. |
| 8,383,099 B2 | 2/2013 | Dudley et al. |
| 2011/0293637 A1 | 12/2011 | Hacohen et al. |
| 2012/0244133 A1 | 9/2012 | Rosenberg et al. |

FOREIGN PATENT DOCUMENTS

| | | | |
|---|---|---|---|
| WO | WO 2012/140130 A1 | 10/2012 | |
| WO | WO 2014/012051 A1 | 1/2014 | |
| WO | WO 2014/133567 A1 | 9/2014 | |
| WO | WO 2014/133568 A1 | 9/2014 | |
| WO | WO-2015184228 A1 * | 12/2015 | ......... C07K 14/7051 |
| WO | WO 2016/053338 A1 | 4/2016 | |
| WO | WO 2016/053339 A1 | 4/2016 | |
| WO | WO-2017189254 A1 * | 11/2017 | ......... C07K 14/7051 |

OTHER PUBLICATIONS

Gros et al. (Nat Med. Apr. 2016;22(4):433-8 and Supplementary Data pp. 1-42, e-published Feb. 22, 2016) (Year: 2016).*
The Memorandum from Deputy Commissioner for Patent Examination Policy Andrew H. Hirshfeld, dated Mar. 4, 2014, 19 pages in total with first page not numbered. (Year: 2014).*
"Evaluating subject Matter Eligibility Under 35 U.S.C. § 101," Mar. 19, 2014 update, pp. 1-93. (Year: 2014).*
Ahmadzadeh et al., "Tumor antigen-specific CD8 T cells infiltrating the tumor express high levels of PD-1 and are functionally impaired," *Blood*, 114(8): 1537-44 (2009).
Arai et al., "Upregulation of TIM-3 and PD-1 on CD4+ and CD8+ T Cells Associated with Dysfunction of Cell-Mediated Immunity after Colorectal Cancer Operation," *Yonago Acta Medica*, 55: 1-9 (2012).
Baitsch et al., "Exhaustion of tumor-specific CD8$^+$T cells in metastases from melanoma patients," *J. Clin. Invest.*, 121(6): 2350-60 (2011).
Baitsch et al., "Extended co-expression of inhibitory receptors by human CD8 T-cells depending on differentiation, antigen-specificity and anatomical localization," *PLoS One*, 7(2): e30852 1-10 (2012).
Cohen et al., "Enhanced antitumor activity of murine-human hybrid T-cell receptor (TCR) in human lymphocytes is associated with improved pairing and TCR/CD3 stability," *Cancer Res.*, 66: 8878-8886 (2006).
Cohen et al., "Enhanced antitumor activity of T cells engineered to express T-cell receptors with a second disulfide bond," *Cancer Res.*, 67: 3898-3903 (2007).
Dobin et al., "STAR: ultrafast universal RNA-seq aligner," *Bioinformatics*, 29: 15-21 (2013).
Dudley et al., "Generation of tumor-infiltrating lymphocyte cultures for use in adoptive transfer therapy for melanoma patients," *J. Immunother.*, 26:332-42 (2003).
Duraiswamy et al., "Phenotype, function, and gene expression profiles of programmed death-1(hi) CD8 T cells in healthy human adults," *J. Immunol.*, 186: 4200-12 (2011).
Gros et al., "PD-1 identifies the patient-specific CD8$^+$tumor-reactive repertoire infiltrating human tumors," *J. Clin. Invest.*, 124(5): 2246-59 (Mar. 25, 2014).

(Continued)

*Primary Examiner* — Zachary S Skelding
(74) *Attorney, Agent, or Firm* — Leydig, Voit & Mayer

(57) ABSTRACT

Disclosed are methods of isolating T cells and TCRs having antigenic specificity for a mutated amino acid sequence encoded by a cancer-specific mutation. Also disclosed are related methods of preparing a population of cells, populations of cells, TCRs, pharmaceutical compositions, and methods of treating or preventing cancer.

16 Claims, 2 Drawing Sheets

Specification includes a Sequence Listing.

(56) References Cited

OTHER PUBLICATIONS

Gros et al.., "Selection of PD-1, LAG-3, TIM3 and 41BB Positive CD8 T Cells in the Fresh Tumor Digest Enriches for Melanoma. Reactive Cells", *Abstracts for the 27th Annual Scientific Meetings of the Society for Immunotherapy of Cancer (SITC)*, Retrieved from the Internet: http://sitcancer.org/UserFiles/file/Abstracts_for_the_27th_Annual_Scientfic_Meeting.9_v1.pdf (May 13, 2014).

Haga-Friedman et al., "Incorporation of transmembrane hydrophobic mutations in the TCR enhance its surface expression and T cell functional avidity," *J. Immunol.*, 188: 5538-5546 (2012).

Inozume et al., "Selection of CD8+PD-1+ lymphocytes in fresh human melanomas enriches for tumor-reactive T cells," *J. Immunother.*, 33(9): 956-64 (2010).

International Searching Authority, International Search Report in International Application No. PCT/US2016/030137, dated Aug. 1, 2016.

International Searching Authority, Written Opinion in International Application No. PCT/US2016/030137, dated Aug. 1, 2016.

Linnemann et al., "High-throughput identification of antigen-specific TCRs by TCR gene capture," *Nature Med.*, 19(11): 1534-1541 (2013).

Lu et al., "Efficient identification of mutated cancer antigens recognized by T cells associated with durable tumor regressions," *Clin. Cancer Res.*, 20: 3401-3410 (2014).

Nielsen et al., "An in vitro-transcribed-mRNA polyepitope construct encoding 32 distinct HLA class I-restricted epitopes from CMV, EBV, and Influenza for use as a functional control in human immune monitoring studies," *J. Immunol., Meth.*, 360: 149-156 (2010).

Riddell et al., "The use of anti-CD3 and anti-CD28 monoclonal antibodies to clone and expand human antigen-specific T cells," *J. Immunol. Methods*, 128:189-201 (1990).

Robbins et al., "A pilot trial using lymphocytes genetically engineered with an NY-ESO-1-reactive T-cell receptor: long-term follow-up and correlates with response," *Clin. Cancer Res.*, 21(5): 1019-27 (Dec. 23, 2014).

Robbins et al., "Mining exomic sequencing data to identify mutated antigens recognized by adoptively transferred tumor-reactive T cells," *Nature Med.*, 19(6): 747-752 (2013).

Ronaghi et al., "A sequencing method based on real-time pyrophosphate," *Science*, 281(5375): 363-365 (1998).

Rosenberg et al., "Durable complete responses in heavily pretreated patients with metastatic melanoma using T-cell transfer immunotherapy," *Clin. Cancer Res.*, 17(13): 4550-57 (2011).

Rosenberg, Steven A., "The Curative Potential of T Cell Immunotherapy for Cancer," *Plenary Talk given at the American Association for Cancer Research conference*, Apr. 7, 2014.

Tran et al., "Cancer immunotherapy based on mutation-specific CD4+ T cells in a patient with epithelial cancer," *Science*, 344: 641-645 (May 8, 2014).

Tran et al., "T-cell therapy against cancer mutations," *Oncotarget*, 5(13): 4579-4580 (Jul. 19, 2014).

Trapnell et al., "Transcript assembly and quantification by RNA-Seq reveals unannotated transcripts and isoform switching during cell differentiation," *Nature Biotechnol.*, 8: 511-515 (2010).

Turcotte et al., "Tumor-reactive CD8+ T cells in metastatic gastrointestinal cancer refractory to chemotherapy," *Clin. Cancer Res.*, 20(2): 331-43 (2013).

Vita et al., "The immune epitope database (IEDB) 3.0," *Nucleic Acids Res.*, 43: D405-412 (2015).

Voelkerding et al., "Next-generation sequencing: from basic research to diagnostics," *Clinical Chemistry*, 55: 641-658 (2009).

Zhang et al., "The impact of next-generation sequencing on genomics," *J. Genet. Genomics*, 38(3): 95-109 (2011).

"TRA T-cell receptor alpha locus [*Homo sapiens* (human)]," Gene ID: 6955, (updated Oct. 9, 2016), Entrez Gene (www.ncbi.nlm.nih.gov/gene), printed on Dec. 8, 2016.

"TRB T cell receptor beta locus [*Homo sapiens* (human)]," Gene ID: 6957, (updated Oct. 9, 2016), Entrez Gene (www.ncbi.nlm.nih.gov/gene), printed on Dec. 8, 2016.

\* cited by examiner

METHODS OF ISOLATING T CELLS AND T CELL RECEPTORS HAVING ANTIGENIC SPECIFICITY FOR A CANCER-SPECIFIC MUTATION FROM PERIPHERAL BLOOD

CROSS-REFERENCE TO RELATED APPLICATIONS

This patent application is the U.S. national stage of PCT/US2016/030137, filed Apr. 29, 2016, which claims the benefit of U.S. Provisional Patent Application No. 62/155,830, filed May 1, 2015, each of which is incorporated by reference in its entirety herein.

STATEMENT REGARDING FEDERALLY SPONSORED RESEARCH AND DEVELOPMENT

This invention was made with Government support under project number ZIABC010984 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 98,375 Byte ASCII (Text) file named "730741_ST25.TXT" dated Oct. 16, 2017.

BACKGROUND OF THE INVENTION

Adoptive cell therapy (ACT) using tumor infiltrating lymphocytes (TIL) or cells that have been genetically engineered to express an anti-cancer antigen T cell receptor (TCR) can produce positive clinical responses in some cancer patients. Nevertheless, obstacles to the successful use of ACT for the widespread treatment of cancer and other diseases remain. For example, T cells and TCRs that specifically recognize cancer antigens may be difficult to identify and/or isolate from a patient. Accordingly, there is a need for improved methods of obtaining cancer-reactive T cells and TCRs.

BRIEF SUMMARY OF THE INVENTION

An embodiment of the invention provides a method of isolating T cells having antigenic specificity for a mutated amino acid sequence encoded by a cancer-specific mutation, the method comprising obtaining a bulk population of peripheral blood mononuclear cells (PBMCs) from a sample of peripheral blood from a patient; selecting T cells that express programmed cell death 1 (PD-1) from the bulk population; separating the T cells that express PD-1 from cells that do not express PD-1 to obtain a T cell population enriched for T cells that express PD-1; identifying one or more genes in the nucleic acid of a cancer cell of the patient, each gene containing a cancer-specific mutation that encodes a mutated amino acid sequence; inducing autologous antigen presenting cells (APCs) of the patient to present the mutated amino acid sequence; co-culturing T cells from the population enriched for T cells that express PD-1 with the autologous APCs that present the mutated amino acid sequence; and selecting the T cells that (a) were co-cultured with the autologous APCs that present the mutated amino acid sequence and (b) have antigenic specificity for the mutated amino acid sequence presented in the context of a major histocompatibility complex (MHC) molecule expressed by the patient.

Another embodiment of the invention provides a method of isolating T cells having antigenic specificity for a mutated amino acid sequence encoded by a cancer-specific mutation, the method comprising obtaining a first population of PBMCs from a sample of peripheral blood from a patient; selecting T cells that express PD-1 from the bulk population; separating the T cells that express PD-1 from cells that do not express PD-1 to obtain a T cell population enriched for T cells that express PD-1; isolating nucleotide sequence(s) that encode(s) one or more TCR(s), or antigen-binding portion(s) thereof, from the T cells of the population enriched for T cells that express PD-1; introducing the nucleotide sequence(s) encoding the TCR(s), or antigen binding portion(s) thereof, into further population(s) of PBMCs to obtain T cells that express the TCR(s), or antigen binding portion(s) thereof; identifying one or more genes in the nucleic acid of a cancer cell of the patient, each gene containing a cancer-specific mutation that encodes a mutated amino acid sequence; inducing autologous APCs of the patient to present the mutated amino acid sequence; co-culturing the T cells that express the TCR(s), or antigen binding portion(s) thereof, with the autologous APCs that present the mutated amino acid sequence; and selecting the T cells that (a) were co-cultured with the autologous APCs that present the mutated amino acid sequence and (b) have antigenic specificity for the mutated amino acid sequence presented in the context of a MHC molecule expressed by the patient.

Another embodiment of the invention provides an isolated or purified TCR comprising the amino acid sequences of (a) SEQ ID NOs: 5-10; (b) SEQ ID NOs: 13-18; (c) SEQ ID NOs: 21-26; (d) SEQ ID NOs: 29-34; or (e) SEQ ID NOs: 37-42.

Another embodiment of the invention provides an isolated or purified polypeptide comprising the amino acid sequences of (a) SEQ ID NOs: 5-10; (b) SEQ ID NOs: 13-18; (c) SEQ ID NOs: 21-26; (d) SEQ ID NOs: 29-34; or (e) SEQ ID NOs: 37-42.

An isolated or purified protein comprising (a) a first polypeptide chain comprising the amino acid sequences of SEQ ID NOs: 5-7 and a second polypeptide chain comprising the amino acid sequences of SEQ ID NOs: 8-10; (b) a first polypeptide chain comprising the amino acid sequences of SEQ ID NOs: 13-15 and a second polypeptide chain comprising the amino acid sequences of SEQ ID NOs: 16-18; (c) a first polypeptide chain comprising the amino acid sequences of SEQ ID NOs: 21-23 and a second polypeptide chain comprising the amino acid sequences of SEQ ID NOs: 24-26; (d) a first polypeptide chain comprising the amino acid sequences of SEQ ID NOs: 29-31 and a second polypeptide chain comprising the amino acid sequences of SEQ ID NOs: 32-34; or (e) a first polypeptide chain comprising the amino acid sequences of SEQ ID NOs: 37-39 and a second polypeptide chain comprising the amino acid sequences of SEQ ID NOs: 40-42.

Additional embodiments of the invention provide related nucleic acids, recombinant expression vectors, host cells, populations of cells, pharmaceutical compositions, and methods of treating or preventing cancer.

BRIEF DESCRIPTION OF THE SEVERAL VIEWS OF THE DRAWING(S)

FIG. 1 is a graph showing the frequency of 4-1BB+ cells (%) in the populations of peripheral blood lymphocytes (PBL) transduced with a control (empty) vector (Vector Td) or a TCR isolated from tandem minigene (TMG)-1 specific cells isolated from PD-1hi population (Vb3 TCR Td) cultured alone (unshaded bars) or upon co-culture with OKT3 antibody (grey bars) or target autologous dendritic cells pulsed with no peptide (vertically striped bars), wild type CASP8 (wt CASP8) peptide (checkered bars), or mutated CASP8 (mut CASP8) peptide (diagonally striped bars).

DETAILED DESCRIPTION OF THE INVENTION

Figure 1:
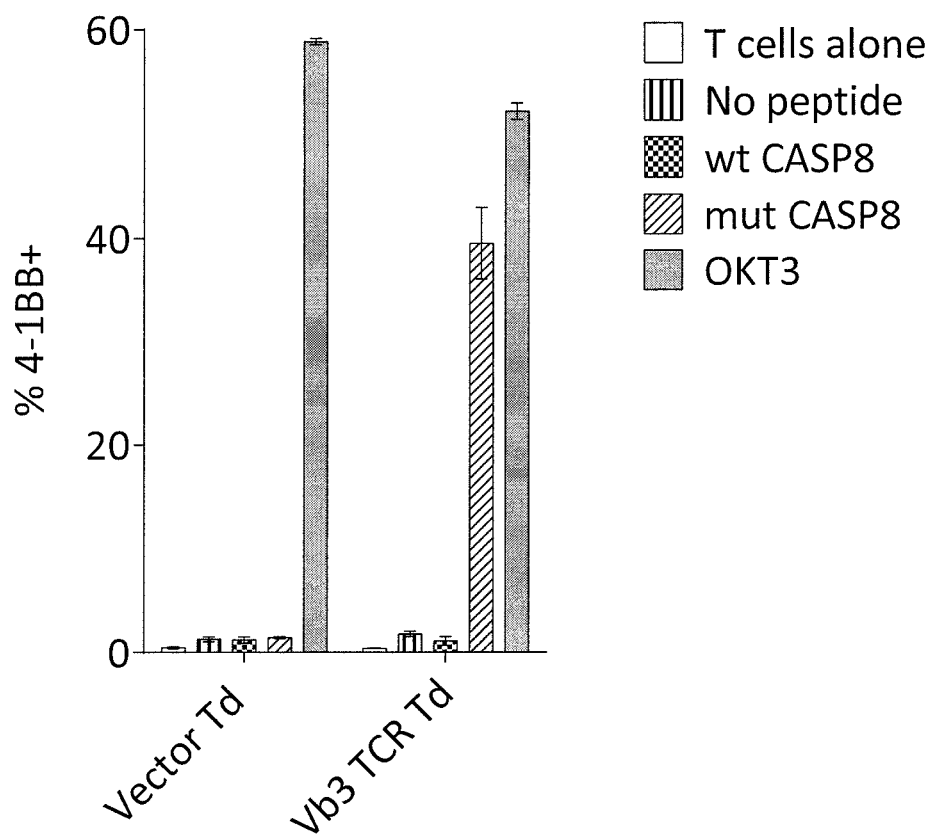

An embodiment of the invention provides a method of isolating T cells having antigenic specificity for a mutated amino acid sequence encoded by a cancer-specific mutation. The invention provides many advantages. For example, the inventive methods may, advantageously, obtain cancer antigen-reactive T cells from a patient's peripheral blood, which is a more accessible and abundant source of T cells as compared to other tissues such as, for example, tumor. By obtaining cancer antigen-reactive T cells from the peripheral blood, the inventive methods may, advantageously, obtain cancer antigen-reactive T cells without using invasive techniques such as, for example, surgery or biopsy, which may be required when obtaining T cells from other tissues such as, for example, a tumor. Cancer antigen-reactive T cells are not frequently found in the peripheral blood. Nevertheless, the inventive methods overcome this obstacle, and effectively and efficiently identify and enrich for these infrequent, cancer antigen-reactive T cells from the peripheral blood. In addition, the inventive methods make it possible to administer ACT to patients that have no tumors available for TIL harvest. The inventive methods may also reduce the cost of ACT, making ACT available for a larger number of patients.

Moreover, the inventive methods may rapidly assess a large number of mutations restricted by all of the patient's MHC molecules at one time, which may identify the full repertoire of the patient's mutation-reactive T cells. Additionally, by distinguishing immunogenic cancer mutations from (a) silent cancer-specific mutations (which do not encode a mutated amino acid sequence) and (b) cancer-specific mutations that encode a non-immunogenic amino acid sequence, the inventive methods may identify one or more cancer-specific, mutated amino acid sequences that may be targeted by a T cell, a TCR, or an antigen-binding portion thereof. The mutated amino acid sequences could be used to synthesize peptides and immunize patients to treat or prevent cancer recurrence. In addition, the invention may provide T cells, TCRs, and antigen-binding portions thereof, having antigenic specificity for mutated amino acid sequences encoded by cancer-specific mutations that are unique to the patient, thereby providing "personalized" T cells, TCRs, and antigen-binding portions thereof, that may be useful for treating or preventing the patient's cancer. The inventive methods may also avoid the technical biases inherent in traditional methods of identifying cancer antigens such as, for example, those using cDNA libraries, and may also be less time-consuming and laborious than those methods. For example, the inventive methods may select mutation-reactive T cells without co-culturing the T cells with tumor cell lines, which may be difficult to generate, particularly for e.g., epithelial cancers. Without being bound to a particular theory or mechanism, it is believed that the inventive methods may identify and isolate T cells and TCRs, or antigen-binding portions thereof, that target the destruction of cancer cells while minimizing or eliminating the destruction of normal, non-cancerous cells, thereby reducing or eliminating toxicity. Accordingly, the invention may also provide T cells, TCRs, or antigen-binding portions thereof, that successfully treat or prevent cancer such as, for example, cancers that do not respond to other types of treatment such as, for example, chemotherapy alone, surgery, or radiation.

The method may comprise obtaining a bulk population of PBMCs from a sample of peripheral blood of a patient by any suitable method known in the art. Suitable methods of obtaining a bulk population of PBMCs may include, but are not limited to, a blood draw and/or a leukopheresis. The bulk population of PBMCs obtained from a peripheral blood sample may comprise T cells, including tumor-reactive T cells.

The method may comprise selecting T cells that express PD-1 from the bulk population. In an embodiment of the invention, the T cells that express PD-1 may be PD-1hi cells. In a preferred embodiment, selecting T cells that express PD-1 from the bulk population comprises selecting T cells that co-express (a) PD-1 and (b) any one or more of CD3, CD4, CD8, T cell immunoglobulin and mucin domain 3 (TIM-3), and CD27. In an embodiment of the invention, the cells that express CD3, CD4, CD8, TIM-3, or CD27 may be CD3hi, CD4hi, CD8hi, TIM-3hi, or CD27hi cells, respectively. The method may comprise specifically selecting the cells in any suitable manner. Preferably, the selecting is carried out using flow cytometry. The flow cytometry may be carried out using any suitable method known in the art. The flow cytometry may employ any suitable antibodies and stains. For example, the specific selection of PD-1, CD3, CD4, CD8, TIM-3, or CD27 may be carried out using anti-PD-1, anti-CD3, anti-CD4, anti-CD8, anti-TIM-3, or anti-CD27 antibodies, respectively. Preferably, the antibody is chosen such that it specifically recognizes and binds to the particular biomarker being selected. The antibody or antibodies may be conjugated to a bead (e.g., a magnetic bead) or to a fluorochrome. Preferably, the flow cytometry is fluorescence-activated cell sorting (FACS).

In an embodiment of the invention, selecting may comprise specifically selecting PD-1+ T cells that are also positive for expression of (i) any one of CD4, CD8, TIM-3, and CD27; (ii) both of CD8 and TIM-3; (iii) both of CD8 and CD27; (iv) both of TIM-3 and CD27; (v) all three of CD8, TIM-3, and CD27; (vi) both of CD4 and TIM-3; (vii) both of CD4 and CD27; or (viii) all three of CD4, TIM-3, and CD27. In another embodiment of the invention, any one or more of the populations of (i)-(viii) may also co-express CD3.

In an embodiment of the invention, selecting T cells that express PD-1 from the bulk population comprises selecting any one or more of (a) CD8+PD-1+; (b) PD-1+TIM-3+; (c) PD-1+CD27+; (d) CD8+PD-1 hi; (e) CD8+PD-1+TIM-3+;

(f) CD8+PD-1+CD27hi; (g) CD8+PD-1+CD27+; (h) CD8+PD-1+TIM-3−; (i) CD8+PD-1+CD27−; (j) CD4+PD-1+; (k) CD4+PD-1hi; (l) CD4+PD-1+TIM-3+; (m) CD4+PD-1+CD27hi; (n) CD4+PD-1+CD27+; (o) CD4+PD-1+TIM-3−; and (p) CD4+PD-1+CD27− T cells. In another embodiment of the invention, any one or more of the populations of (a)-(p) may also co-express CD3.

As used herein, the term "positive" (which may be abbreviated as "+"), with reference to expression of the indicated cell marker, means that the cell expresses the indicated cell marker at any detectable level, which may include, for example, expression at a low (but detectable) level as well as expression at a high (hi) level. The term "negative" (which may be abbreviated as "−"), as used herein with reference to expression of the indicated cell marker, means that the cell does not express the indicated cell marker at a detectable level. The term "high" (which may be abbreviated as "hi"), as used herein with reference to expression of the indicated cell marker, refers to a subset of cells that are positive for expression of the indicated cell marker which stain more brightly for the indicated cell marker using one of the following methods (e.g., FACS, flow cytometry, immunofluorescence assays or microscopy) than other cells that are positive for expression of the indicated cell marker. For example, cells with a "high" level of expression of the indicated cell marker may stain more brightly than about 50%, about 60%, about 70%, about 80%, about 90%, or about 95%, or a range of any two of the foregoing values, of the other cells that are positive for expression of the indicated cell marker.

In an embodiment of the invention, selecting T cells that express PD-1 may comprise selecting combinations of PD-1$^+$ cells, each PD-1+ cell expressing any one, two, or more different markers as described herein. In this regard, the method may produce a cell population that is enriched for tumor-reactive cells that comprises a mixture of PD-1+ cells, each PD-1+ cell expressing any one, two, or more different markers described herein. In an embodiment of the invention, selecting T cells that express PD-1 comprises selecting a combination of (i) both PD-1−CD8+ cells and PD-1+TIM-3+ cells; (ii) both PD-1+CD8+ cells and PD-1+CD27+ cells; (iii) both PD-1+TIM-3+ cells and PD-1+CD27+ cells; (iv) all of PD-1+CD8+ cells, PD-1+TIM-3+ cells, and PD-1+CD27+ cells; (v) both PD-1+CD4+ cells and PD-1+TIM-3+ cells; (vi) both PD-1+CD4+ cells and PD-1+CD27+ cells; (vii) all of PD-1+CD4+ cells, PD-1+TIM-3+ cells, and PD-1+CD27+ cells, or (viii) a combination of any of the populations of (i)-(vii). In another embodiment of the invention, any one or more of the populations of (i)-(vii) may also co-express CD3. In another embodiment of the invention, selecting T cells that express PD-1 comprises selecting a combination of any two or more of (a) CD8+PD-1+; (b) PD-1+TIM-3+; (c) PD-1+CD27+; (d) CD8+PD-1hi; (e) CD8+PD-1+TIM-3+; (f) CD8+PD-1+CD27hi; (g) CD8+PD-1+CD27+; (h) CD8+PD-1+TIM-3−; (i) CD8+PD-1+CD27−; (j) CD4+PD-1+; (k) CD4+PD-1hi; (l) CD4+PD-1+TIM-3+; (m) CD4+PD-1+CD27hi; (n) CD4+PD-1+CD27+; (o) CD4+PD-1+TIM-3−; and (p) CD4+PD-1+CD27− cells. In another embodiment of the invention, any one or more of the populations of (a)-(p) may also co-express CD3.

The method may comprise separating the T cells that express PD-1 from cells that do not express PD-1 to obtain a T cell population enriched for T cells that express PD-1. In this regard, the selected cells may be physically separated from unselected cells, i.e., the cells that do not express PD-1. The selected cells may be separated from unselected cells by any suitable method such as, for example, sorting.

The method may comprise identifying one or more genes in the nucleic acid of a cancer cell of a patient, each gene containing a cancer-specific mutation that encodes a mutated amino acid sequence. The cancer cell may be obtained from any bodily sample derived from a patient which contains or is expected to contain tumor or cancer cells. The bodily sample may be any tissue sample such as blood, a tissue sample obtained from the primary tumor or from tumor metastases, or any other sample containing tumor or cancer cells. The nucleic acid of the cancer cell may be DNA or RNA.

In order to identify cancer-specific mutations, the method may further comprise sequencing nucleic acid such as DNA or RNA of normal, noncancerous cells and comparing the nucleic acid sequence of the cancer cell with the sequence of the normal, noncancerous cell. The normal, noncancerous cell may be obtained from the patient or a different individual.

The cancer-specific mutation may be any mutation in any gene which encodes a mutated amino acid sequence (also referred to as a "non-silent mutation") and which is expressed in a cancer cell but not in a normal, noncancerous cell. Non-limiting examples of cancer-specific mutations that may be identified in the inventive methods include missense, nonsense, insertion, deletion, duplication, frameshift, and repeat expansion mutations. In an embodiment of the invention, the method comprises identifying at least one gene containing a cancer-specific mutation which encodes a mutated amino acid sequence. However, the number of genes containing such a cancer-specific mutation that may be identified using the inventive methods is not limited and may include more than one gene (for example, about 2, about 3, about 4, about 5, about 10, about 11, about 12, about 13, about 14, about 15, about 20, about 25, about 30, about 40, about 50, about 60, about 70, about 80, about 90, about 100, about 150, about 200, about 400, about 600, about 800, about 1000, about 1500, about 2000 or more, or a range defined by any two of the foregoing values). Likewise, in an embodiment of the invention, the method comprises identifying at least one cancer-specific mutation which encodes a mutated amino acid sequence. However, the number of such cancer-specific mutations that may be identified using the inventive methods is not limited and may include more than one cancer-specific mutation (for example, about 2, about 3, about 4, about 5, about 10, about 11, about 12, about 13, about 14, about 15, about 20, about 25, about 30, about 40, about 50, about 60, about 70, about 80, about 90, about 100, about 150, about 200, about 400, about 600, about 800, about 1000, about 1500, about 2000 or more, or a range defined by any two of the foregoing values). In an embodiment in which more than one cancer-specific mutation is identified, the cancer-specific mutations may be located in the same gene or in different genes.

In an embodiment, identifying one or more genes in the nucleic acid of a cancer cell comprises sequencing the whole exome, the whole genome, or the whole transcriptome of the cancer cell. Sequencing may be carried out in any suitable manner known in the art. Examples of sequencing techniques that may be useful in the inventive methods include Next Generation Sequencing (NGS) (also referred to as "massively parallel sequencing technology") or Third Generation Sequencing. NGS refers to non-Sanger-based high-throughput DNA sequencing technologies. With NGS, millions or billions of DNA strands may be sequenced in parallel, yielding substantially more throughput and minimizing the need for the fragment-cloning methods that are often used in Sanger sequencing of genomes. In NGS, nucleic acid templates may be randomly read in parallel along the entire genome by breaking the entire genome into small pieces. NGS may, advantageously, provide nucleic acid sequence information of a whole genome, exome, or transcriptome in very short time periods, e.g., within about 1 to about 2 weeks, preferably within about 1 to about 7 days, or most preferably, within less than about 24 hours. Multiple NGS platforms which are commercially available or which are described in the literature can be used in the context of the inventive methods, e.g., those described in Zhang et al., *J. Genet. Genomics*, 38(3): 95-109 (2011) and Voelkerding et al., *Clinical Chemistry*, 55: 641-658 (2009).

Non-limiting examples of NGS technologies and platforms include sequencing-by-synthesis (also known as "pyrosequencing") (as implemented, e.g., using the GS-FLX 454 Genome Sequencer, 454 Life Sciences (Branford, Conn.), ILLUMINA SOLEXA Genome Analyzer (Illumina Inc., San Diego, Calif.), or the ILLUMINA HISEQ 2000 Genome Analyzer (Illumina), or as described in, e.g., Ronaghi et al., *Science*, 281(5375): 363-365 (1998)), sequencing-by-ligation (as implemented, e.g., using the SOLID platform (Life Technologies Corporation, Carlsbad, Calif.) or the POLONATOR G.007 platform (Dover Systems, Salem, N.H.)), single-molecule sequencing (as implemented, e.g., using the PACBIO RS system (Pacific Biosciences (Menlo Park, Calif.) or the HELISCOPE platform (Helicos Biosciences (Cambridge, Mass.)), nano-technology for single-molecule sequencing (as implemented, e.g., using the GRIDON platform of Oxford Nanopore Technologies (Oxford, UK), the hybridization-assisted nano-pore sequencing (HANS) platforms developed by Nabsys (Providence, R.I.), and the ligase-based DNA sequencing platform with DNA nanoball (DNB) technology referred to as probe-anchor ligation (cPAL)), electron microscopy-based technology for single-molecule sequencing, and ion semiconductor sequencing.

The method may comprise inducing autologous APCs of the patient to present the mutated amino acid sequence. The APCs may include any cells which present peptide fragments of proteins in association with MHC molecules on their cell surface. The APCs may include, for example, any one or more of macrophages, dendritic cells (DCs), langerhans cells, B-lymphocytes, and T-cells. Preferably, the APCs are DCs. By using autologous APCs from the patient, the inventive methods may, advantageously, identify T cells, TCRs, and antigen-binding portions thereof, that have antigenic specificity for a mutated amino acid sequence encoded by a cancer-specific mutation that is presented in the context of an MHC molecule expressed by the patient. The MHC molecule can be any MHC molecule expressed by the patient including, but not limited to, MHC Class I, MHC Class II, HLA-A, HLA-B, HLA-C, HLA-DM, HLA-DO, HLA-DP, HLA-DQ, and HLA-DR molecules. The inventive methods may, advantageously, identify mutated amino acid sequences presented in the context of any MHC molecule expressed by the patient without using, for example, epitope prediction algorithms to identify MHC molecules or mutated amino acid sequences, which may be useful only for a select few MHC class I alleles and may be constrained by the limited availability of reagents to select mutation-reactive T cells (e.g., an incomplete set of MHC tetramers). Accordingly, in an embodiment of the invention, the inventive methods advantageously identify mutated amino acid sequences presented in the context of any MHC molecule expressed by the patient and are not limited to any particular MHC molecule. Preferably, the autologous APCs are antigen-negative autologous APCs.

Inducing autologous APCs of the patient to present the mutated amino acid sequence may be carried out using any suitable method known in the art. In an embodiment of the invention, inducing autologous APCs of the patient to present the mutated amino acid sequence comprises pulsing the autologous APCs with peptides comprising the mutated amino acid sequence or a pool of peptides, each peptide in the pool comprising a different mutated amino acid sequence. Each of the mutated amino acid sequences in the pool may be encoded by a gene containing a cancer specific mutation. In this regard, the autologous APCs may be cultured with a peptide or a pool of peptides comprising the mutated amino acid sequence in a manner such that the APCs internalize the peptide(s) and display the mutated amino acid sequence(s), bound to an MHC molecule, on the cell membrane. In an embodiment in which more than one gene is identified, each gene containing a cancer-specific mutation that encodes a mutated amino acid sequence, the method may comprise pulsing the autologous APCs with a pool of peptides, each peptide in the pool comprising a different mutated amino acid sequence. Methods of pulsing APCs are known in the art and are described in, e.g., Solheim (Ed.), *Antigen Processing and Presentation Protocols* (*Methods in Molecular Biology*), Human Press, (2010). The peptide(s) used to pulse the APCs may include the mutated amino acid(s) encoded by the cancer-specific mutation. The peptide(s) may further comprise any suitable number of contiguous amino acids from the endogenous protein encoded by the identified gene on each of the carboxyl side and the amino side of the mutated amino acid(s). The number of contiguous amino acids from the endogenous protein flanking each side of the mutation is not limited and may be, for example, about 4, about 5, about 6, about 7, about 8, about 9, about 10, about 11, about 12, about 13, about 14, about 15, about 16, about 17, about 18, about 19, about 20, or a range defined by any two of the foregoing values. Preferably, the peptide(s) comprise(s) about 12 contiguous amino acids from the endogenous protein on each side of the mutated amino acid(s).

In an embodiment of the invention, inducing autologous APCs of the patient to present the mutated amino acid sequence comprises introducing a nucleotide sequence encoding the mutated amino acid sequence into the APCs. The nucleotide sequence is introduced into the APCs so that the APCs express and display the mutated amino acid sequence, bound to an MHC molecule, on the cell membrane. The nucleotide sequence encoding the mutated amino acid may be RNA or DNA. Introducing a nucleotide sequence into APCs may be carried out in any of a variety of different ways known in the art as described in, e.g., Solheim et al. supra. Non-limiting examples of techniques that are useful for introducing a nucleotide sequence into APCs include transformation, transduction, transfection, and electroporation. In an embodiment in which more than one gene is identified, the method may comprise preparing more than one nucleotide sequence, each encoding a mutated amino acid sequence encoded by a different gene, and introducing each nucleotide sequence into a different population of autologous APCs. In this regard, multiple populations of autologous APCs, each population expressing and displaying a different mutated amino acid sequence, may be obtained.

In an embodiment in which more than one gene is identified, each gene containing a cancer-specific mutation that encodes a mutated amino acid sequence, the method may comprise introducing a nucleotide sequence encoding the more than one gene. In this regard, in an embodiment of the invention, the nucleotide sequence introduced into the autologous APCs is a tandem minigene (TMG) construct, each minigene comprising a different gene, each gene including a cancer-specific mutation that encodes a mutated amino acid sequence. Each minigene may encode one mutation identified by the inventive methods flanked on each side of the mutation by any suitable number of contiguous amino acids from the endogenous protein encoded by the identified gene, as described herein with respect to other aspects of the invention. The number of minigenes in the construct is not limited and may include for example, about 5, about 10, about 11, about 12, about 13, about 14, about 15, about 20, about 25, or more, or a range defined by any two of the foregoing values. The APCs express the mutated amino acid sequences encoded by the TMG construct and display the mutated amino acid sequences, bound to an MHC molecule, on the cell membranes. In an embodiment, the method may comprise preparing more than one TMG construct, each construct encoding a different set of mutated amino acid sequences encoded by different genes, and introducing each TMG construct into a different population of autologous APCs. In this regard, multiple populations of autologous APCs, each population expressing and displaying mutated amino acid sequences encoded by different TMG constructs, may be obtained.

The method may comprise co-culturing T cells from the population enriched for T cells that express PD-1 with the autologous APCs that present the mutated amino acid sequence. The T cells from the population enriched for T cells that express PD-1 are obtained from peripheral blood as described herein with respect to other aspects of the invention. The T cells can express PD-1 and any of the other cell markers described herein with respect to other aspects of the invention. The method may comprise co-culturing the T cells that express PD-1 and autologous APCs so that the T cells encounter the mutated amino acid sequence presented by the APCs in such a manner that the T cells specifically bind to and immunologically recognize a mutated amino acid sequence presented by the APCs. In an embodiment of the invention, the T cells are co-cultured in direct contact with the autologous APCs.

The method may comprise selecting the T cells that (a) were co-cultured with the autologous APCs that present the mutated amino acid sequence and (b) have antigenic specificity for the mutated amino acid sequence presented in the context of a MHC molecule expressed by the patient. The phrase "antigenic specificity," as used herein, means that a T cell, TCR, or the antigen-binding portion thereof, expressed by the T cell, can specifically bind to and immunologically recognize the mutated amino acid sequence encoded by the cancer-specific mutation. The selecting may comprise identifying the T cells that have antigenic specificity for the mutated amino acid sequence and separating them from T cells that do not have antigenic specificity for the mutated amino acid sequence. Selecting the T cells having antigenic specificity for the mutated amino acid sequence may be carried out in any suitable manner. In an embodiment of the invention, the method comprises expanding the numbers of T cells that express PD-1, e.g., by co-culturing with a T cell growth factor, such as interleukin (IL)-2 or IL-15, or as described herein with respect to other aspects of the invention, prior to selecting the T cells that have antigenic specificity for the mutated amino acid sequence. In an embodiment of the invention, the method does not comprise expanding the numbers of T cells that express PD-1 with a T cell growth factor, such as IL-2 or IL-15 prior to selecting the T cells that have antigenic specificity for the mutated amino acid sequence.

For example, upon co-culture of the T cells that express PD-1 with the APCs that present the mutated amino acid sequence, T cells having antigenic specificity for the mutated amino acid sequence may express any one or more of a variety of T cell activation markers which may be used to identify those T cells having antigenic specificity for the mutated amino acid sequence. Such T cell activation markers may include, but are not limited to, PD-1, lymphocyte-activation gene 3 (LAG-3), TIM-3, 4-1BB, OX40, and CD107a. Accordingly, in an embodiment of the invention, selecting the T cells that have antigenic specificity for the mutated amino acid sequence comprises selecting the T cells that express any one or more of PD-1, LAG-3, TIM-3, 4-1BB, OX40, and CD107a. Cells expressing one or more T cell activation markers may be sorted on the basis of expression of the marker using any of a variety of techniques known in the art such as, for example, FACS or magnetic-activated cell sorting (MACS) as described in, e.g., Turcotte et al., *Clin. Cancer Res.*, 20(2): 331-43 (2013) and Gros et al., *J. Clin. Invest.*, 124(5): 2246-59 (2014).

In another embodiment of the invention, selecting the T cells that have antigenic specificity for the mutated amino acid sequence comprises selecting the T cells (i) that secrete a greater amount of one or more cytokines upon co-culture with APCs that present the mutated amino acid sequence as compared to the amount of the one or more cytokines secreted by a negative control or (ii) in which at least twice as many of the numbers of T cells secrete one or more cytokines upon co-culture with APCs that present the mutated amino acid sequence as compared to the numbers of negative control T cells that secrete the one or more cytokines. The one or more cytokines may comprise any cytokine the secretion of which by a T cell is characteristic of T cell activation (e.g., a TCR expressed by the T cells specifically binding to and immunologically recognizing the mutated amino acid sequence). Non-limiting examples of cytokines, the secretion of which is characteristic of T cell activation, include IFN-γ, IL-2, and tumor necrosis factor alpha (TNF-α), granulocyte/monocyte colony stimulating factor (GM-CSF), IL-4, IL-5, IL-9, IL-10, IL-17, and IL-22.

For example, the T cells may be considered to have "antigenic specificity" for the mutated amino acid sequence if the T cells secrete at least twice as much IFN-γ upon co-culture with (a) antigen-negative APCs pulsed with a concentration of a peptide comprising the mutated amino acid sequence (e.g., about 0.001 ng/mL to about 10 μg/mL, e.g., 0.001 ng/ml, 0.005 ng/mL, 0.01 ng/ml, 0.05 ng/ml, 0.1 ng/mL, 0.5 ng/mL, 1 ng/mL, 5 ng/mL, 100 ng/mL, 1 μg/mL, 5 μg/mL, or 10 μg/mL) or (b) APCs into which a nucleotide sequence encoding the mutated amino acid sequence has been introduced as compared to the amount of IFN-γ secreted by a negative control. The negative control may be, for example, autologous T cells (e.g., derived from PBMCs) co-cultured with (a) antigen-negative APCs pulsed with the same concentration of an irrelevant peptide (e.g., the wild-type amino acid sequence, or some other peptide with a different sequence from the mutated amino acid sequence) or (b) APCs into which a nucleotide sequence encoding an irrelevant peptide sequence has been introduced. The T cells may also have "antigenic specificity" for the mutated amino acid sequence if the T cells secrete a greater amount of IFN-γ upon co-culture with antigen-negative APCs pulsed with higher concentrations of a peptide comprising the mutated amino acid sequence as compared to a negative control, for example, the negative control described above. IFN-γ secretion may be measured by methods known in the art such as, for example, enzyme-linked immunosorbent assay (ELISA).

Alternatively or additionally, the T cells may be considered to have "antigenic specificity" for the mutated amino acid sequence if at least twice as many of the numbers of T cells secrete IFN-γ upon co-culture with (a) antigen-negative APCs pulsed with a concentration of a peptide comprising the mutated amino acid sequence or (b) APCs into which a nucleotide sequence encoding the mutated amino acid sequence has been introduced as compared to the numbers of negative control T cells that secrete IFN-γ. The concentration of peptide and the negative control may be as described herein with respect to other aspects of the invention. The numbers of cells secreting IFN-γ may be measured by methods known in the art such as, for example, ELISPOT.

While T cells having antigenic specificity for the mutated amino acid sequence may both (1) express any one or more T cells activation markers described herein and (2) secrete a greater amount of one or more cytokines as described herein, in an embodiment of the invention, T cells having antigenic specificity for the mutated amino acid sequence may express any one or more T cell activation markers without secreting a greater amount of one or more cytokines or may secrete a greater amount of one or more cytokines without expressing any one or more T cell activation markers.

In another embodiment of the invention, selecting the T cells that have antigenic specificity for the mutated amino acid sequence comprises selectively growing the T cells that have antigenic specificity for the mutated amino acid sequence. In this regard, the method may comprise co-culturing the T cells with autologous APCs in such a manner as to favor the growth of the T cells that have antigenic specificity for the mutated amino acid sequence over the T cells that do not have antigenic specificity for the mutated amino acid sequence. Accordingly, a population of T cells is provided that has a higher proportion of T cells that have antigenic specificity for the mutated amino acid sequence as compared to T cells that do not have antigenic specificity for the mutated amino acid sequence.

In an embodiment of the invention in which T cells are co-cultured with autologous APCs expressing multiple mutated amino acid sequences (e.g., multiple mutated amino acid sequences encoded by a TMG construct or multiple mutated amino acid sequences in a pool of peptides pulsed onto autologous APCs), selecting the T cells may further comprise separately assessing T cells for antigenic specificity for each of the multiple mutated amino acid sequences. For example, the inventive method may further comprise separately inducing autologous APCs of the patient to present each mutated amino acid sequence encoded by the construct (or included in the pool), as described herein with respect to other aspects of the invention (for example, by providing separate APC populations, each presenting a different mutated amino acid sequence encoded by the construct (or included in the pool)). The method may further comprise separately co-culturing T cells with the different populations of autologous APCs that present each mutated amino acid sequence, as described herein with respect to other aspects of the invention. The method may further comprise separately selecting the T cells that (a) were co-cultured with the autologous APCs that present the mutated amino acid sequence and (b) have antigenic specificity for the mutated amino acid sequence presented in the context of a MHC molecule expressed by the patient, as described herein with respect to other aspects of the invention. In this regard, the method may comprise determining which mutated amino acid sequence encoded by a TMG construct that encodes multiple mutated amino acid sequences (or included in the pool) are immunologically recognized by the T cells (e.g., by process of elimination).

The method may further comprise isolating a nucleotide sequence that encodes the TCR, or the antigen-binding portion thereof, from the selected T cells, wherein the TCR, or the antigen-binding portion thereof, has antigenic specificity for the mutated amino acid sequence encoded by the cancer-specific mutation. In an embodiment of the invention, prior to isolating the nucleotide sequence that encodes the TCR, or the antigen-binding portion thereof, the numbers selected T cells that have antigenic specificity for the mutated amino acid sequence may be expanded. Expansion of the numbers of T cells can be accomplished by any of a number of methods as are known in the art as described in, for example, U.S. Pat. Nos. 8,034,334; 8,383,099; U.S. Patent Application Publication No. 2012/0244133; Dudley et al., *J. Immunother.*, 26:332-42 (2003); and Riddell et al., *J. Immunol. Methods*, 128:189-201 (1990). In an embodiment, expansion of the numbers of T cells is carried out by culturing the T cells with OKT3 antibody, IL-2, and feeder PBMC (e.g., irradiated allogeneic PBMC). In another embodiment of the invention, the numbers of selected T cells that have antigenic specificity for the mutated amino acid sequence are not expanded prior to isolating the nucleotide sequence that encodes the TCR, or the antigen-binding portion thereof. For example, the TCR, or antigen binding portion thereof, may be isolated from a single cell.

The "the antigen-binding portion" of the TCR, as used herein, refers to any portion comprising contiguous amino acids of the TCR of which it is a part, provided that the antigen-binding portion specifically binds to the mutated amino acid sequence encoded by the gene identified as described herein with respect to other aspects of the invention. The term "antigen-binding portion" refers to any part or fragment of the TCR of the invention, which part or fragment retains the biological activity of the TCR of which it is a part (the parent TCR). Antigen-binding portions encompass, for example, those parts of a TCR that retain the ability to specifically bind to the mutated amino acid sequence, or detect, treat, or prevent cancer, to a similar extent, the same extent, or to a higher extent, as compared to the parent TCR. In reference to the parent TCR, the functional portion can comprise, for instance, about 10%, 25%, 30%, 50%, 68%, 80%, 90%, 95%, or more, of the parent TCR.

The antigen-binding portion can comprise an antigen-binding portion of either or both of the α and β chains of the TCR of the invention, such as a portion comprising one or more of the complementarity determining region (CDR)1, CDR2, and CDR3 of the variable region(s) of the α chain and/or β chain of the TCR of the invention. In an embodiment of the invention, the antigen-binding portion can comprise the amino acid sequence of the CDR1 of the α chain (CDR1α), the CDR2 of the α chain (CDR2α), the CDR3 of the α chain (CDR3α), the CDR1 of the β chain (CDR1β), the CDR2 of the β chain (CDR2β), the CDR3 of the β chain (CDR3β), or any combination thereof. Preferably, the antigen-binding portion comprises the amino acid sequences of CDR1α, CDR2α, and CDR3α; the amino acid sequences of CDR1β, CDR2β, and CDR3β; or the amino acid sequences of all of CDR1α, CDR2α, CDR3α, CDR1β, CDR2β, and CDR3β of the inventive TCR.

In an embodiment of the invention, the antigen-binding portion can comprise, for instance, the variable region of the inventive TCR comprising a combination of the CDR regions set forth above. In this regard, the antigen-binding portion can comprise the amino acid sequence of the variable region of the α chain (Vα), the amino acid sequence of the variable region of the β chain (Vβ), or the amino acid sequences of both of the Vα and Vβ of the inventive TCR.

In an embodiment of the invention, the antigen-binding portion may comprise a combination of a variable region and a constant region. In this regard, the antigen-binding portion can comprise the entire length of the α or β chain, or both of the α and β chains, of the inventive TCR.

Isolating the nucleotide sequence that encodes the TCR, or the antigen-binding portion thereof, from the selected T cells may be carried out in any suitable manner known in the art. For example, the method may comprise isolating RNA from the selected T cells and sequencing the TCR, or the antigen-binding portion thereof, using established molecular cloning techniques and reagents such as, for example, 5' Rapid Amplification of cDNA Ends (RACE) polymerase chain reaction (PCR) using TCR-α and -β chain constant primers.

In an embodiment of the invention, the method may comprise cloning the nucleotide sequence that encodes the TCR, or the antigen-binding portion thereof, into a recombinant expression vector using established molecular cloning techniques as described in, e.g., Green et al. (Eds.), *Molecular Cloning: A Laboratory Manual*, Cold Spring Harbor Laboratory Press; 4th Ed. (2012). For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The recombinant expression vectors can comprise any type of nucleotides, including, but not limited to DNA (e.g., complementary DCA (cDNA)) and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages does not hinder the transcription or replication of the vector.

The recombinant expression vector of the invention can be any suitable recombinant expression vector, and can be used to transform or transfect any suitable host cell. Suitable vectors include those designed for propagation and expansion or for expression or both, such as plasmids and viruses. The vector can be selected from the group consisting of transposon/transposase, the pUC series (Fennentas Life Sciences), the pBluescript series (Stratagene, La Jolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM and pMAMneo (Clontech). Preferably, the recombinant expression vector is a viral vector, e.g., a retroviral vector.

The TCR, or the antigen-binding portion thereof, isolated by the inventive methods may be useful for preparing cells for adoptive cell therapies. In this regard, an embodiment of the invention provides a method of preparing a population of cells that express a TCR, or an antigen-binding portion thereof, having antigenic specificity for a mutated amino acid sequence encoded by a cancer-specific mutation, the method comprising isolating a TCR, or an antigen-binding portion thereof, as described herein with respect to other aspects of the invention, and introducing the nucleotide sequence encoding the isolated TCR, or the antigen-binding portion thereof, into host cells to obtain cells that express the TCR, or the antigen-binding portion thereof.

Introducing the nucleotide sequence (e.g., a recombinant expression vector) encoding the isolated TCR, or the antigen-binding portion thereof, into host cells may be carried out in any of a variety of different ways known in the art as described in, e.g., Green et al. supra. Non-limiting examples of techniques that are useful for introducing a nucleotide sequence into host cells include transformation, transduction, transfection, and electroporation.

The host cell into which the nucleotide sequence encoding the TCR, or antigen binding portion thereof, is introduced may be any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell, can be an adherent cell or a suspended cell, i.e., a cell that grows in suspension. Suitable host cells are known in the art and include, for instance, DH5α *E. coli* cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH59α cell. For purposes of producing the TCR, or antigen binding portion thereof, the host cell is preferably a mammalian cell. Most preferably, the host cell is a human cell. While the host cell can be of any cell type, can originate from any type of tissue, and can be of any developmental stage, the host cell preferably is a PBL or a PBMC. More preferably, the host cell is a T cell.

In an embodiment of the invention, the PBMC include T cells. The T cells may be any type of T cell. Without being bound to a particular theory or mechanism, it is believed that less differentiated, "younger" T cells may be associated with any one or more of greater in vivo persistence, proliferation, and antitumor activity as compared to more differentiated, "older" T cells. Accordingly, the inventive methods may, advantageously, identify and isolate a TCR, or an antigen-binding portion thereof, that has antigenic specificity for the mutated amino acid sequence and introduce the TCR, or an antigen-binding portion thereof, into "younger" T cells that may provide any one or more of greater in vivo persistence, proliferation, and antitumor activity as compared to "older" T cells (e.g., effector cells in a patient's tumor).

In an embodiment of the invention, the host cells are autologous to the patient. In this regard, the TCRs, or the antigen-binding portions thereof, identified and isolated by the inventive methods may be personalized to each patient. However, in another embodiment, the inventive methods may identify and isolate TCRs, or the antigen-binding portions thereof, that have antigenic specificity against a mutated amino acid sequence that is encoded by a recurrent (also referred to as "hot-spot") cancer-specific mutation. In this regard, the method may comprise introducing the nucleotide sequence encoding the isolated TCR, or the antigen-binding portion thereof, into host cells that are allogeneic to the patient. For example, the method may comprise introducing the nucleotide sequence encoding the isolated TCR, or the antigen-binding portion thereof, into the host cells from another patient whose tumors express the same mutation in the context of the same MHC molecule.

In an embodiment of the invention, the method further comprises expanding the numbers of host cells that express the TCR, or the antigen-binding portion thereof. The numbers of host cells may be expanded, for example, as described herein with respect to other aspects of the invention. In this regard, the inventive methods may, advantageously, generate a large number of T cells having antigenic specificity for the mutated amino acid sequence.

Another embodiment of the invention provides a TCR, or an antigen-binding portion thereof, isolated by any of the methods described herein with respect to other aspects of the invention. An embodiment of the invention provides a TCR comprising two polypeptides (i.e., polypeptide chains), such as an alpha ($\alpha$) chain of a TCR, a beta ($\beta$) chain of a TCR, a gamma ($\gamma$) chain of a TCR, a delta ($\delta$) chain of a TCR, or a combination thereof. Another embodiment of the invention provides an antigen-binding portion of the TCR comprising one or more CDR regions, one or more variable regions, or one or both of the $\alpha$ and $\beta$ chains of the TCR, as described herein with respect to other aspects of the invention. The polypeptides of the inventive TCR, or the antigen-binding portion thereof, can comprise any amino acid sequence, provided that the TCR, or the antigen-binding portion thereof, has antigenic specificity for the mutated amino acid sequence encoded by the cancer-specific mutation.

In an embodiment of the invention, the TCR, or antigen binding portion thereof, has antigenic specificity for MAGE-A6$_{E168K}$. The phrase "antigenic specificity," as used herein, means that the TCR can specifically bind to and immunologically recognize the particular antigen under discussion. Wild-type, non-mutated MAGE-A6 comprises the amino acid sequence of SEQ ID NO: 74. MAGE-A6$_{E168K}$ comprises the amino acid sequence of SEQ ID NO: 74 except that the glutamic acid at position 168 of SEQ ID NO: 74 is substituted with lysine. In an embodiment of the invention, the TCR has antigenic specificity for the MAGE-A6$_{E168K}$ amino acid sequence of SEQ ID NO: 77.

The anti-MAGE-A6$_{E168K}$ TCR, or antigen binding portion thereof, comprises a CDR1 comprising the amino acid sequence of SEQ ID NO: 5 or 13 (CDR1 of $\alpha$ chain), a CDR2 comprising the amino acid sequence of SEQ ID NO: 6 or 14 (CDR2 of $\alpha$ chain), and a CDR3 comprising the amino acid sequence of SEQ ID NO: 7 or 15 (CDR3 of $\alpha$ chain), and a second polypeptide chain comprising a CDR1 comprising the amino acid sequence of SEQ ID NO: 8 or 16 (CDR1 of $\beta$ chain), a CDR2 comprising the amino acid sequence of SEQ ID NO: 9 or 17 (CDR2 of $\beta$ chain), and a CDR3 comprising the amino acid sequence of SEQ ID NO: 10 or 18 (CDR3 of $\beta$ chain). In this regard, the inventive TCR, or antigen binding portion thereof, can comprise any one or more of the amino acid sequences selected from the group consisting of SEQ ID NOs: 5-10 and SEQ ID NOs: 13-18. In an especially preferred embodiment, the TCR, or antigen binding portion thereof, comprises the amino acid sequences of (i) all of SEQ ID NOs: 5-10 or (ii) all of SEQ ID NOs: 13-18.

In an embodiment of the invention, the TCR, or antigen binding portion thereof, has antigenic specificity for PDS5A$_{Y1000F;\ H1007Y}$. Wild-type, non-mutated PDS5A comprises the amino acid sequence of SEQ ID NO: 75. PDS5A$_{Y1000F;\ H1007Y}$ comprises the amino acid sequence of SEQ ID NO: 75 except that the tyrosine at position 1000 of SEQ ID NO: 75 is substituted with phenylalanine and the histidine at position 1007 of SEQ ID NO: 75 is substituted with tyrosine. In an embodiment of the invention, the TCR, or antigen binding portion thereof, has antigenic specificity for the PDS5A$_{Y1000F;\ H1007Y}$ amino acid sequence of SEQ ID NO: 78.

In an embodiment of the invention, the anti-PDS5A$_{Y1000F;\ H1007Y}$ TCR, or antigen binding portion thereof comprises the amino acid sequence of SEQ ID NO: 21 (CDR1 of $\alpha$ chain), a CDR2 comprising the amino acid sequence of SEQ ID NO: 22 (CDR2 of $\alpha$ chain), and a CDR3 comprising the amino acid sequence of SEQ ID NO: 23 (CDR3 of $\alpha$ chain), and a second polypeptide chain comprising a CDR1 comprising the amino acid sequence of SEQ ID NO: 24 (CDR1 $\beta$ chain), a CDR2 comprising the amino acid sequence of SEQ ID NO: 25 (CDR2 of $\beta$ chain), and a CDR3 comprising the amino acid sequence of SEQ ID NO: 26 (CDR3 of $\beta$ chain). In this regard, the inventive TCR, or antigen binding portion thereof, can comprise any one or more of the amino acid sequences selected from the group consisting of SEQ ID NOs: 21-26. In an especially preferred embodiment, the TCR, or antigen binding portion thereof, comprises the amino acid sequences of all of SEQ ID NOs: 21-26.

In an embodiment of the invention, the TCR, or antigen binding portion thereof, has antigenic specificity for MED13$_{P1691S}$. Wild-type, non-mutated MED13 comprises the amino acid sequence of SEQ ID NO: 76. MED13$_{P1691S}$ comprises the amino acid sequence of SEQ ID NO: 76 except that the proline at position 1691 of SEQ ID NO: 76 is substituted with serine. In an embodiment of the invention, the TCR, or antigen binding portion thereof, has antigenic specificity for the MED13$_{P1691S}$ amino acid sequence of SEQ ID NO: 79.

In an embodiment of the invention, the anti-MED13$_{P1691S}$ TCR, or antigen binding portion thereof, comprises a CDR1 comprising the amino acid sequence of SEQ ID NO: 29 or 37 (CDR1 of $\alpha$ chain), a CDR2 comprising the amino acid sequence of SEQ ID NO: 30 or 38 (CDR2 of $\alpha$ chain), and a CDR3 comprising the amino acid sequence of SEQ ID NO: 31 or 39 (CDR3 of $\alpha$ chain), and a second polypeptide chain comprising a CDR1 comprising the amino acid sequence of SEQ ID NO: 32 or 40 (CDR1 of $\beta$ chain), a CDR2 comprising the amino acid sequence of SEQ ID NO: 33 or 41 (CDR2 of $\beta$ chain), and a CDR3 comprising the amino acid sequence of SEQ ID NO: 34 or 42 (CDR3 of $\beta$ chain). In this regard, the inventive TCR, or antigen binding portion thereof, can comprise any one or more of the amino acid sequences selected from the group consisting of SEQ ID NOs: 29-34 and SEQ ID NOs: 37-42. In an especially preferred embodiment, the TCR, or antigen binding portion thereof, comprises the amino acid sequences of (i) all of SEQ ID NOs: 29-34 or (ii) all of SEQ ID NOs: 37-42.

In an embodiment of the invention, the TCR can comprise an amino acid sequence of a variable region of a TCR comprising the CDRs set forth above. In this regard, the TCR can comprise the amino acid sequence of SEQ ID NO: 11 or 19 (the variable region of an $\alpha$ chain of an anti-MAGE-A6$_{E168K}$ TCR); SEQ ID NO: 12, wherein X at position 2 of SEQ ID NO: 12 is Gly or Ala (the variable region of a $\beta$ chain of an anti-MAGE-A6$_{E168K}$ TCR); SEQ ID NO: 20, wherein X at position 2 of SEQ ID NO: 20 is Gly or Ala (the variable region of a $\beta$ chain of an anti-MAGE-A6$_{E168K}$ TCR); both SEQ ID NOs: 11 and 12; both SEQ ID NOs: 19 and 20; SEQ ID NO: 27 (the variable region of an $\alpha$ chain of the anti-PDS5A$_{Y1000F;\ H1007Y}$TCR); SEQ ID NO: 28, wherein X at position 2 of SEQ ID NO: 28 is Gly or Ala (the variable region of a β chain of the anti-PDS5A$_{Y1000F; H1007Y}$ TCR); both SEQ ID NOs: 27 and 28; SEQ ID NO: 35 or 43 (the variable region of an α chain of an anti-MED13$_{P1691S}$ TCR); SEQ ID NO: 36, wherein X at position 2 of SEQ ID NO: 36 is Gly or Ala (the variable region of a β chain of an anti-MED13$_{P1691S}$ TCR); SEQ ID NO: 44, wherein X at position 2 of SEQ ID NO: 44 is Gly or Ala (the variable region of a β chain of an anti-MED13$_{P1691S}$ TCR); both SEQ ID NOs: 35 and 36; or both SEQ ID NOs: 43 and 44. Preferably, the inventive TCR comprises the amino acid sequences of (a) SEQ ID NOs: 11-12; (b) SEQ ID NOs: 19-20; (c) SEQ ID NOs: 27-28; (d) SEQ ID NOs: 35-36; or (e) SEQ ID NOs: 43-44.

The inventive TCRs may further comprise a constant region derived from any suitable species such as, e.g., human or mouse. As used herein, the term "murine" or "human," when referring to a TCR or any component of a TCR described herein (e.g., complementarity determining region (CDR), variable region, constant region, alpha chain, and/or beta chain), means a TCR (or component thereof) which is derived from a mouse or a human, respectively, i.e., a TCR (or component thereof) that originated from or was, at one time, expressed by a mouse T cell or a human T cell, respectively.

In an embodiment of the invention, the constant region is a human constant region. In this regard, the TCR can comprise SEQ ID NO: 61 (constant region of a human α chain); SEQ ID NO: 62 (constant region of a human β chain); SEQ ID NO: 63 (constant region of a human β chain); both SEQ ID NO: 61 and SEQ ID NO: 62; or both SEQ ID NOs: 61 and 63. The TCR may comprise any of the CDR regions as described herein with respect to other aspects of the invention. In another embodiment of the invention, the TCR may comprise any of the variable regions described herein with respect to other aspects of the invention.

In an embodiment of the invention, the TCR further comprises a murine constant region. For example, the TCR may be a chimeric TCR comprising a human variable region and a murine constant region. In this regard, the TCR can comprise SEQ ID NO: 47 (constant region of a murine α chain); SEQ ID NO: 48 (constant region of a murine β chain); or both SEQ ID NO: 47 and SEQ ID NO: 48. The chimeric TCR may comprise any of the CDR regions as described herein with respect to other aspects of the invention. In another embodiment of the invention, the chimeric TCR may comprise any of the variable regions described herein with respect to other aspects of the invention. In an embodiment of the invention, the TCR comprises a murine constant region, optionally with one, two, three, or four amino acid substitution(s) in the constant region of one or both of the alpha and beta chains, as described herein with respect to other aspects of the invention. In an embodiment of the invention, the TCR comprises a murine constant region, optionally with one, two, three, or four amino acid substitution(s) in the murine constant region of the alpha chain and one amino acid substitution in the murine constant region of the beta chain, as described herein with respect to other aspects of the invention.

In some embodiments, the TCRs comprising the substituted amino acid sequence(s) advantageously provide one or more of increased recognition of mutated amino acid sequence-positive targets, increased expression by a host cell, and increased anti-tumor activity as compared to the parent TCR comprising an unsubstituted amino acid sequence. In general, the substituted amino acid sequences of the murine constant regions of the TCR α and β chains, SEQ ID NOs: 45 and 46, respectively, correspond with all or portions of the unsubstituted murine constant region amino acid sequences SEQ ID NOs: 47 and 48, respectively, with SEQ ID NO: 45 having one, two, three, or four amino acid substitution(s) when compared to SEQ ID NO: 47 and SEQ ID NO: 46 having one amino acid substitution when compared to SEQ ID NO: 48. In this regard, an embodiment of the invention provides a TCR comprising the amino acid sequences of one or both of (a) SEQ ID NO: 45 (constant region of alpha chain), wherein (i) X at position 48 is Thr or Cys; (ii) X at position 112 is Ser, Gly, Ala, Val, Leu, Ile, Pro, Phe, Met, or Trp; (iii) X at position 114 is Met, Gly, Ala, Val, Leu, Ile, Pro, Phe, Met, or Trp; and (iv) X at position 115 is Gly, Ala, Val, Leu, Ile, Pro, Phe, Met, or Trp; and (b) SEQ ID NO: 46 (constant region of beta chain), wherein X at position 57 is Ser or Cys. In an embodiment of the invention, the TCR comprising SEQ ID NO: 45 does not comprise SEQ ID NO: 47 (unsubstituted murine constant region of alpha chain). In an embodiment of the invention, the TCR comprising SEQ ID NO: 46 does not comprise SEQ ID NO: 48 (unsubstituted murine constant region of beta chain).

In an embodiment of the invention, the substituted amino acid sequence includes cysteine substitutions in the constant region of one or both of the α and β chains to provide a cysteine-substituted TCR. Opposing cysteines in the α and the β chains provide a disulfide bond that links the constant regions of the α and the β chains of the substituted TCR to one another and which is not present in a TCR comprising the unsubstituted human constant region or the unsubstituted murine constant region. In this regard, the TCR is a cysteine-substituted TCR in which one or both of the native Thr48 of SEQ ID NO: 47 and the native Ser57 of SEQ ID NO: 48 may be substituted with Cys. Preferably, both of the native Thr48 of SEQ ID NO: 47 and the native Ser57 of SEQ ID NO: 48 are substituted with Cys. In an embodiment, the cysteine-substituted TCR comprises an alpha chain constant region comprising the amino acid sequence of SEQ ID NO: 45, wherein X at position 48 is Cys, X at position 112 is the native Ser, X at position 114 is the native Met, and X at position 115 is the native Gly, and a beta chain constant region comprising the amino acid sequence of SEQ ID NO: 46, wherein X at position 57 is Cys. The cysteine-substituted TCRs of the invention may include the substituted constant region in addition to any of the CDRs or variable regions described herein.

In an embodiment of the invention, the substituted amino acid sequence includes substitutions of one, two, or three amino acids in the transmembrane (TM) domain of the constant region of one or both of the α and β chains with a hydrophobic amino acid to provide a hydrophobic amino acid-substituted TCR. The hydrophobic amino acid substitution(s) in the TM domain of the TCR may increase the hydrophobicity of the TM domain of the TCR as compared to a TCR that lacks the hydrophobic amino acid substitution(s) in the TM domain. In this regard, the TCR may be a hydrophobic amino acid-substituted TCR in which one, two, or three of the native Ser112, Met114, and Gly115 of SEQ ID NO: 47 may, independently, be substituted with Gly, Ala, Val, Leu, Ile, Pro, Phe, Met, or Trp; preferably with Leu, Ile, or Val. Preferably, all three of the native Ser112, Met114, and Gly115 of SEQ ID NO: 47 are, independently, substituted with Gly, Ala, Val, Leu, Ile, Pro, Phe, Met, or Trp; preferably with Leu, Ile, or Val. In an embodiment, the hydrophobic amino acid-substituted TCR comprises an alpha chain constant region comprising the amino acid sequence of SEQ ID NO: 45, wherein X at position 48 is the native Thr, X at position 112 is Ser, Gly, Ala, Val, Leu, Ile, Pro, Phe, Met, or Trp, X at position 114 is Met, Gly, Ala, Val, Leu, Ile, Pro, Phe, Met, or Trp, and X at position 115 is Gly, Ala, Val, Leu, Ile, Pro, Phe, Met, or Trp, and a beta chain constant region comprising the amino acid sequence of SEQ ID NO: 46, wherein X at position 57 is the native Ser, wherein the hydrophobic amino acid-substituted TCR comprising SEQ ID NO: 45 does not comprise SEQ ID NO: 47 (unsubstituted murine constant region of alpha chain). Preferably, the hydrophobic amino acid-substituted TCR comprises an alpha chain constant region comprising the amino acid sequence of SEQ ID NO: 45, wherein X at position 48 is the native Thr, X at position 112 is Leu, X at position 114 is Ile, and X at position 115 is Val, and a beta chain constant region comprising the amino acid sequence of SEQ ID NO: 46, wherein X at position 57 is the native Ser. The hydrophobic amino acid-substituted TCRs of the invention may include the substituted constant region in addition to any of the CDRs or variable regions described herein.

In an embodiment of the invention, the substituted amino acid sequence includes the cysteine substitutions in the constant region of one or both of the α and β chains in combination with the substitution(s) of one, two, or three amino acids in the transmembrane (TM) domain of the constant region of one or both of the α and β chains with a hydrophobic amino acid (also referred to herein as "cysteine-substituted, hydrophobic amino acid-substituted TCR"). In this regard, the TCR is a cysteine-substituted, hydrophobic amino acid-substituted TCR in which the native Thr48 of SEQ ID NO: 47 is substituted with Cys; one, two, or three of the native Ser112, Met114, and Gly115 of SEQ ID NO: 47 are, independently, substituted with Gly, Ala, Val, Leu, Ile, Pro, Phe, Met, or Trp; preferably with Leu, Ile, or Val; and the native Ser57 of SEQ ID NO: 48 is substituted with Cys. Preferably, all three of the native Ser112, Met114, and Gly115 of SEQ ID NO: 47 are, independently, substituted with Gly, Ala, Val, Leu, Ile, Pro, Phe, Met, or Trp; preferably with Leu, Ile, or Val. In an embodiment, the cysteine-substituted, hydrophobic amino acid-substituted TCR comprises an alpha chain constant region comprising the amino acid sequence of SEQ ID NO: 45, wherein X at position 48 is Cys, X at position 112 is Ser, Gly, Ala, Val, Leu, Ile, Pro, Phe, Met, or Trp, X at position 114 is Met, Gly, Ala, Val, Leu, Ile, Pro, Phe, Met, or Trp, and X at position 115 is Gly, Ala, Val, Leu, Ile, Pro, Phe, Met, or Trp, and a beta chain constant region comprising the amino acid sequence of SEQ ID NO: 46, wherein X at position 56 is Cys, wherein the cysteine-substituted, hydrophobic amino acid-substituted TCR comprising SEQ ID NO: 45 does not comprise SEQ ID NO: 47 (unsubstituted murine constant region of alpha chain). Preferably, the cysteine-substituted, hydrophobic amino acid-substituted TCR comprises an alpha chain constant region comprising the amino acid sequence of SEQ ID NO: 49 and a beta chain constant region comprising the amino acid sequence of SEQ ID NO: 50. The cysteine-substituted, hydrophobic amino acid-substituted, TCRs of the invention may include the substituted constant region in addition to any of the CDRs or variable regions described herein. In an especially preferred embodiment, the cysteine-substituted, hydrophobic amino acid-substituted TCR comprises a full-length alpha chain comprising the amino acid sequence of SEQ ID NO: 51, 53, 55, 57, or 59 and a full-length beta chain comprising the amino acid sequence of SEQ ID NO: 52, 54, 56, 58, or 60. In this regard, the Cys-substituted, hydrophobic amino acid-substituted TCR can comprise the amino acid sequences of (a) both of SEQ ID NOs: 51-52; (b) both of SEQ ID NOs: 53-54; (c) both of SEQ ID NOs: 55-56; (d) both of SEQ ID NOs: 57-58; or (e) both of SEQ ID NOs: 59-60.

Also provided by the invention is a polypeptide comprising an antigen-binding portion of any of the TCRs described herein. The term "polypeptide" as used herein includes oligopeptides and refers to a single chain of amino acids connected by one or more peptide bonds. The antigen-binding portion can comprise additional amino acids at the amino or carboxy terminus of the portion, or at both termini, which additional amino acids are not found in the amino acid sequence of the parent TCR. Desirably, the additional amino acids do not interfere with the biological function of the antigen-binding portion, e.g., specifically binding to a mutated amino acid sequence; and/or having the ability to detect cancer, treat or prevent cancer, etc. More desirably, the additional amino acids enhance the biological activity, as compared to the biological activity of the parent TCR.

The polypeptide can comprise an antigen-binding portion of either or both of the α and β chains of the TCRs of the invention, such as an antigen-binding portion comprising one of more of CDR1, CDR2, and CDR3 of the variable region(s) of the α chain and/or β chain of a TCR of the invention. In an embodiment of the invention, the polypeptide can comprise an antigen-binding portion comprising the amino acid sequence of SEQ ID NO: 5, 13, 21, 29, or 37 (CDR1 of α chain), SEQ ID NO: 6, 14, 22, 30, or 38 (CDR2 of α chain), SEQ ID NO: 7, 15, 23, 31, or 39 (CDR3 of α chain), SEQ ID NO: 8, 16, 24, 32, or 40 (CDR1 of β chain), SEQ ID NO: 9, 17, 25, 33, or 41 (CDR2 of β chain), SEQ ID NO: 10, 18, 26, 34, or 42 (CDR3 of β chain), or a combination thereof. Preferably, the inventive polypeptide comprises the amino acid sequences of (a) all of SEQ ID NOs: 5-10; (b) all of SEQ ID NOs: 13-18; (c) all of SEQ ID NOs: 21-26; (d) all of SEQ ID NOs: 29-34; or (e) all of SEQ ID NOs: 37-42.

In an embodiment of the invention, the inventive polypeptide can comprise, for instance, the variable region of the inventive TCR comprising a combination of the CDR regions set forth above. In this regard, the polypeptide can comprise the amino acid sequence of SEQ ID NO: 11 or 19 (the variable region of an α chain of an anti-MAGE-A6$_{E168K}$ TCR); SEQ ID NO: 12, wherein X at position 2 of SEQ ID NO: 12 is Gly or Ala (the variable region of a β chain of an anti-MAGE-A6$_{E168K}$ TCR); SEQ ID NO: 20, wherein X at position 2 of SEQ ID NO: 20 is Gly or Ala (the variable region of a β chain of an anti-MAGE-A6$_{E168K}$ TCR); both SEQ ID NOs: 11 and 12; both SEQ ID NOs: 19 and 20; SEQ ID NO: 27 (the variable region of an α chain of the anti-PDS5A$_{Y1000F;\ H1007Y}$ TCR); SEQ ID NO: 28, wherein X at position 2 of SEQ ID NO: 28 is Gly or Ala (the variable region of a β chain of the anti-PDS5A$_{Y1000F;\ H1007Y}$ TCR); both SEQ ID NOs: 27 and 28; SEQ ID NO: 35 or 43 (the variable region of an α chain of an anti-MED13$_{P1691S}$ TCR); SEQ ID NO: 36, wherein X at position 2 of SEQ ID NO: 36 is Gly or Ala (the variable region of a β chain of an anti-MED13$_{P1691S}$ TCR); SEQ ID NO: 44, wherein X at position 2 of SEQ ID NO: 44 is Gly or Ala (the variable region of a β chain of an anti-MED13$_{P1691S}$ TCR); both SEQ ID NOs: 35 and 36; or both SEQ ID NOs: 43 and 44. Preferably, the inventive polypeptide comprises the amino acid sequences of (a) SEQ ID NOs: 11-12; (b) SEQ ID NOs: 19-20; (c) SEQ ID NOs: 27-28; (d) SEQ ID NOs: 35-36; or (e) SEQ ID NOs: 43-44.

The inventive polypeptide may further comprise a constant region derived from any suitable species such as, e.g., human or mouse, described herein or any of the substituted constant regions described herein. In this regard, the polypeptide can comprise the amino acid sequence of SEQ ID NO: 45 (constant region of α chain, substituted as described herein with respect to other aspects of the invention), SEQ ID NO: 47 (the unsubstituted constant region of a murine α chain), SEQ ID NO: 46 (constant region of β chain, substituted as described herein with respect to other aspects of the invention), SEQ ID NO: 48 (the unsubstituted constant region of a murine β chain), SEQ ID NO: 49 (constant region of a cysteine-substituted, hydrophobic amino acid-substituted α chain), SEQ ID NO: 50 (constant region of a cysteine-substituted β chain), both SEQ ID NOs: 45 and 46, both SEQ ID NOs: 47 and 48, both SEQ ID NOs: 49 and 50, SEQ ID NO: 61 (constant region of a human α chain); SEQ ID NO: 62 (constant region of a human β chain); SEQ ID NO: 63 (constant region of a human β chain); both SEQ ID NO: 61 and SEQ ID NO: 62; or both SEQ ID NOs: 61 and 63.

In an embodiment of the invention, the inventive polypeptide can comprise the entire length of an α or β chain of one of the TCRs described herein. In this regard, the inventive polypeptide can comprise an amino acid sequence of SEQ ID NO: 51, 52, 53, 54, 55, 56, 57, 58, 59, or 60. Preferably, the polypeptide comprises the amino acid sequences of (a) both of SEQ ID NOs: 51-52; (b) both of SEQ ID NOs: 53-54; (c) both of SEQ ID NOs: 55-56; (d) both of SEQ ID NOs: 57-58; or (e) both of SEQ ID NOs: 59-60.

The invention further provides a protein comprising at least one of the polypeptides described herein. By "protein" is meant a molecule comprising one or more polypeptide chains.

In an embodiment of the invention, the protein may comprise the CDR sequences of the inventive TCR. In this regard, the protein of the invention can comprise: (a) a first polypeptide chain comprising the amino acid sequences of SEQ ID NOs: 5-7 and a second polypeptide chain comprising the amino acid sequences of: SEQ ID NOs: 8-10; (b) a first polypeptide chain comprising the amino acid sequences of SEQ ID NOs: 13-15 and a second polypeptide chain comprising the amino acid sequences of: SEQ ID NOs: 16-18; (c) a first polypeptide chain comprising the amino acid sequences of SEQ ID NOs: 21-23 and a second polypeptide chain comprising the amino acid sequences of: SEQ ID NOs: 24-26; (d) a first polypeptide chain comprising the amino acid sequences of SEQ ID NOs: 29-31 and a second polypeptide chain comprising the amino acid sequences of: SEQ ID NOs: 32-34; or (e) a first polypeptide chain comprising the amino acid sequences of SEQ ID NOs: 37-39 and a second polypeptide chain comprising the amino acid sequences of: SEQ ID NOs: 40-42.

In an embodiment of the invention, the protein may comprise the variable region sequences of the inventive TCR. In this regard, the protein of the invention can comprise: (a) a first polypeptide chain comprising the amino acid sequence of SEQ ID NO: 11 and a second polypeptide chain comprising the amino acid sequence of SEQ ID NO: 12, wherein X at position 2 of SEQ ID NO: 12 is Gly or Ala; (b) a first polypeptide chain comprising the amino acid sequence of SEQ ID NO: 19 and a second polypeptide chain comprising the amino acid sequence of SEQ ID NO: 20, wherein X at position 2 of SEQ ID NO: 20 is Gly or Ala; (c) a first polypeptide chain comprising the amino acid sequence of SEQ ID NO: 27 and a second polypeptide chain comprising the amino acid sequence of SEQ ID NO: 28, wherein X at position 2 of SEQ ID NO: 28 is Gly or Ala; (d) a first polypeptide chain comprising the amino acid sequence of SEQ ID NO: 35 and a second polypeptide chain comprising the amino acid sequence of SEQ ID NO: 36, wherein X at position 2 of SEQ ID NO: 36 is Gly or Ala; or (e) a first polypeptide chain comprising the amino acid sequence of SEQ ID NO: 43 and a second polypeptide chain comprising the amino acid sequence of SEQ ID NO: 44, wherein X at position 2 of SEQ ID NO: 44 is Gly or Ala.

In an embodiment of the invention, the inventive protein may further comprise TCR constant region sequences. In this regard, the first polypeptide chain of the inventive protein may further comprise the amino acid sequence of SEQ ID NO: 45 (constant region of the alpha chain, substituted as described herein with respect to other aspects of the invention), SEQ ID NO: 47 (the unsubstituted constant region of a murine α chain), or SEQ ID NO: 49 (constant region of a cysteine-substituted, hydrophobic amino acid-substituted α chain); and the second polypeptide chain of the inventive protein may further comprise the amino acid sequence of SEQ ID NO: 46 (constant region of β chain, substituted as described herein with respect to other aspects of the invention), SEQ ID NO: 48 (the unsubstituted constant region of a murine β chain), SEQ ID NO: 50 (constant region of a cysteine-substituted β chain) SEQ ID NO: 61 (constant region of a human α chain); SEQ ID NO: 62 (constant region of a human β chain); SEQ ID NO: 63 (constant region of a human β chain); both SEQ ID NO: 61 and SEQ ID NO: 62; or both SEQ ID NOs: 61 and 63. In a preferred embodiment of the invention, the protein comprises: (a) a first polypeptide chain comprising the amino acid sequence of SEQ ID NO: 45 and a second polypeptide chain comprising the amino acid sequence of SEQ ID NO: 46; (b) a first polypeptide chain comprising the amino acid sequence of SEQ ID NO: 47 and a second polypeptide chain comprising the amino acid sequence of SEQ ID NO: 48; or (c) a first polypeptide chain comprising the amino acid sequence of SEQ ID NO: 49 and a second polypeptide chain comprising the amino acid sequence of SEQ ID NO: 50.

In an embodiment of the invention, the protein may comprise the full length alpha and beta chains of the inventive TCR. In this regard, the protein may comprise (a) a first polypeptide chain comprising the amino acid sequence of SEQ ID NO: 51 and a second polypeptide chain comprising the amino acid sequence of SEQ ID NO: 52; (b) a first polypeptide chain comprising the amino acid sequence of SEQ ID NO: 53 and a second polypeptide chain comprising the amino acid sequence of SEQ ID NO: 54; (c) a first polypeptide chain comprising the amino acid sequence of SEQ ID NO: 55 and a second polypeptide chain comprising the amino acid sequence of SEQ ID NO: 56; (d) a first polypeptide chain comprising the amino acid sequence of SEQ ID NO: 57 and a second polypeptide chain comprising the amino acid sequence of SEQ ID NO: 58; or (e) a first polypeptide chain comprising the amino acid sequence of SEQ ID NO: 59 and a second polypeptide chain comprising the amino acid sequence of SEQ ID NO: 60. In this instance, the protein of the invention can be a TCR. Alternatively, if, for example, the protein comprises a single polypeptide chain comprising SEQ ID NOs: 5-10; or if the first and/or second polypeptide chain(s) of the protein further comprise(s) other amino acid sequences, e.g., an amino acid sequence encoding an immunoglobulin or a portion thereof, then the inventive protein can be a fusion protein. In this regard, the invention also provides a fusion protein comprising at least one of the inventive polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide can encode any peptidic or proteinaceous molecule, or a portion thereof, including, but not limited to an immunoglobulin, CD3, CD4, CD8, an MHC molecule, a CD1 molecule, e.g., CD1a, CD1b, CD1c, CD1d, etc.

The fusion protein can comprise one or more copies of the inventive polypeptide and/or one or more copies of the other polypeptide. For instance, the fusion protein can comprise 1, 2, 3, 4, 5, or more, copies of the inventive polypeptide and/or of the other polypeptide. Suitable methods of making fusion proteins are known in the art, and include, for example, recombinant methods.

The protein of the invention can be a recombinant antibody comprising at least one of the inventive polypeptides described herein. As used herein, "recombinant antibody" refers to a recombinant (e.g., genetically engineered) protein comprising at least one of the polypeptides of the invention and a polypeptide chain of an antibody, or a portion thereof. The polypeptide of an antibody, or portion thereof, can be a heavy chain, a light chain, a variable or constant region of a heavy or light chain, a single chain variable fragment (scFv), or an Fc, Fab, or F(ab)$_2$' fragment of an antibody, etc. The polypeptide chain of an antibody, or portion thereof, can exist as a separate polypeptide of the recombinant antibody. Alternatively, the polypeptide chain of an antibody, or portion thereof, can exist as a polypeptide, which is expressed in frame (in tandem) with the polypeptide of the invention. The polypeptide of an antibody, or portion thereof, can be a polypeptide of any antibody or any antibody fragment.

The TCRs, polypeptides, and proteins of the invention can be of any length, i.e., can comprise any number of amino acids, provided that the TCRs, polypeptides, or proteins retain their biological activity, e.g., the ability to specifically bind to a mutated amino acid sequence; detect cancer; or treat or prevent cancer in a mammal, etc. For example, the polypeptide can be in the range of from about 50 to about 5000 amino acids long, such as 50, 70, 75, 100, 125, 150, 175, 200, 300, 400, 500, 600, 700, 800, 900, 1000 or more amino acids in length. In this regard, the polypeptides of the invention also include oligopeptides.

The TCRs, polypeptides, and proteins of the invention of the invention can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

Included in the scope of the invention are functional variants of the inventive TCRs, polypeptides, and proteins described herein. The teen "functional variant," as used herein, refers to a TCR, polypeptide, or protein having substantial or significant sequence identity or similarity to a parent TCR, polypeptide, or protein, which functional variant retains the biological activity of the TCR, polypeptide, or protein of which it is a variant. Functional variants encompass, for example, those variants of the TCR, polypeptide, or protein described herein (the parent TCR, polypeptide, or protein) that retain the ability to specifically bind to a mutated amino acid sequence for which the parent TCR has antigenic specificity or to which the parent polypeptide or protein specifically binds, to a similar extent, the same extent, or to a higher extent, as the parent TCR, polypeptide, or protein. In reference to the parent TCR, polypeptide, or protein, the functional variant can, for instance, be at least about 30%, 50%, 75%, 80%, 90%, 95%, 96%, 97%, 98%, 99% or more identical in amino acid sequence to the parent TCR, polypeptide, or protein.

The functional variant can, for example, comprise the amino acid sequence of the parent TCR, polypeptide, or protein with at least one conservative amino acid substitution. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

Alternatively or additionally, the functional variants can comprise the amino acid sequence of the parent TCR, polypeptide, or protein with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the parent TCR, polypeptide, or protein.

The TCR, polypeptide, or protein can consist essentially of the specified amino acid sequence or sequences described herein, such that other components of the TCR, polypeptide, or protein, e.g., other amino acids, do not materially change the biological activity of the TCR, polypeptide, or protein.

An embodiment of the invention provides a nucleic acid sequence comprising a nucleotide sequence encoding any of the TCRs, polypeptides, or proteins described herein. "Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In an embodiment, the nucleic acid comprises complementary DNA (cDNA). It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Green and Sambrook et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleic acid can comprise any nucleotide sequence which encodes any of the TCRs, polypeptides, or proteins described herein. In an embodiment of the invention, the nucleotide sequence may comprise, consist, or consist essentially of SEQ ID NO: 64 or 66 (the variable region of an α chain of an anti-MAGE-A6$_{E168K}$ TCR); SEQ ID NO: 65 or 67 (the variable region of a β chain of an anti-MAGE-A6$_{E168K}$ TCR); both SEQ ID NOs: 64 and 65; both SEQ ID NOs: 66 and 67; SEQ ID NO: 68 (the variable region of an α chain of the anti-PDS5A$_{Y1000F; H1007Y}$ TCR); SEQ ID NO: 69 (the variable region of a β chain of the anti-PDS5A$_{Y1000F; H1007Y}$ TCR); both SEQ ID NOs: 68 and 69; SEQ ID NO: 70 or 72 (the variable region of an α chain of an anti-MED13$_{P1691S}$ TCR); SEQ ID NO: 71 or 73 (the variable region of a β chain of an anti-MED13$_{P1691S}$ TCR); both SEQ ID NOs: 70 and 71; or both SEQ ID NOs: 72 and 73. Preferably, the nucleotide sequence comprises (a) SEQ ID NOs: 64-65; (b) SEQ ID NOs: 66-67; (c) SEQ ID NOs: 68-69; (d) SEQ ID NOs: 70-71; or (e) SEQ ID NOs: 72-73.

In an embodiment of the invention, the nucleic acid comprises a codon-optimized nucleotide sequence. Without being bound to a particular theory or mechanism, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency.

The invention also provides a nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive TCRs. It is generally appreciated that conditions can be rendered more stringent by the addition of increasing amounts of formamide.

The invention also provides a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

The nucleic acids of the invention can be incorporated into a recombinant expression vector. In this regard, the invention provides recombinant expression vectors comprising any of the nucleic acids of the invention. The recombinant expression vectors may be as described herein with respect to other aspects of the invention.

Another embodiment of the invention further provides a host cell comprising any of the recombinant expression vectors described herein and populations of host cells. The host cell, and populations thereof, may be as described herein with respect to other aspects of the invention.

The inventive TCRs, polypeptides, proteins, nucleic acids, recombinant expression vectors, and host cells (including populations thereof) can be isolated and/or purified. The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70%, 80%, 90%, 95%, or can be 100%.

Another embodiment of the invention provides an isolated population of cells prepared according to any of the methods described herein with respect to other aspects of the invention. The population of cells can be a heterogeneous population comprising the host cells expressing the isolated TCR, or the antigen-binding portion thereof, in addition to at least one other cell, e.g., a host cell (e.g., a PBMC), which does not express the isolated TCR, or the antigen-binding portion thereof, or a cell other than a T cell, e.g., a B cell, a macrophage, a neutrophil, an erythrocyte, a hepatocyte, an endothelial cell, an epithelial cells, a muscle cell, a brain cell, etc. Alternatively, the population of cells can be a substantially homogeneous population, in which the population comprises mainly of host cells (e.g., consisting essentially of) expressing the isolated TCR, or the antigen-binding portion thereof. The population also can be a clonal population of cells, in which all cells of the population are clones of a single host cell expressing the isolated TCR, or the antigen-binding portion thereof, such that all cells of the population express the isolated TCR, or the antigen-binding portion thereof. In one embodiment of the invention, the population of cells is a clonal population comprising host cells expressing the isolated TCR, or the antigen-binding portion thereof, as described herein. By introducing the nucleotide sequence encoding the isolated TCR, or the antigen binding portion thereof, into host cells, the inventive methods may, advantageously, provide a population of cells that comprises a high proportion of host cells that express the isolated TCR and have antigenic specificity for the mutated amino acid sequence. In an embodiment of the invention, about 1% to about 100%, for example, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, or about 100%, or a range defined by any two of the foregoing values, of the population of cells comprises host cells that express the isolated TCR and have antigenic specificity for the mutated amino acid sequence. Without being bound to a particular theory or mechanism, it is believed that populations of cells that comprise a high proportion of host cells that express the isolated TCR and have antigenic specificity for the mutated amino acid sequence have a lower proportion of irrelevant cells that may hinder the function of the host cell, e.g., the ability of the host cell to target the destruction of cancer cells and/or treat or prevent cancer.

The inventive TCRs, or the antigen-binding portions thereof, polypeptides, proteins, nucleic acids, recombinant expression vectors, host cells, and populations of cells (hereinafter, "inventive TCR material(s)") can be formulated into a composition, such as a pharmaceutical composition. In this regard, the invention provides a pharmaceutical composition comprising any of the inventive TCRs, or the antigen-binding portions thereof, polypeptides, proteins, nucleic acids, recombinant expression vectors, host cells, or populations of cells and a pharmaceutically acceptable carrier. The inventive pharmaceutical composition can comprise an inventive TCR, or an antigen-binding portion thereof, or population of cells in combination with another pharmaceutically active agent(s) or drug(s), such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used for the particular inventive TCR material under consideration. Such pharmaceutically acceptable carriers are well-known to those skilled in the art and are readily available to the public. It is preferred that the pharmaceutically acceptable carrier be one which has no detrimental side effects or toxicity under the conditions of use.

The choice of carrier will be determined in part by the particular inventive TCR material, as well as by the particular method used to administer the inventive TCR material. Accordingly, there are a variety of suitable formulations of the pharmaceutical composition of the invention. Suitable formulations may include any of those for oral, parenteral, subcutaneous, intravenous, intramuscular, intraarterial, intrathecal, or interperitoneal administration. More than one route can be used to administer the inventive TCR material, and in certain instances, a particular route can provide a more immediate and more effective response than another route.

Preferably, the inventive TCR material is administered by injection, e.g., intravenously. When the inventive population of cells is to be administered, the pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, Ill.), PLASMA-LYTE A (Baxter, Deerfield, Ill.), about 5% dextrose in water, or Ringer's lactate. In an embodiment, the pharmaceutically acceptable carrier is supplemented with human serum albumin.

It is contemplated that the inventive TCR materials, and pharmaceutical compositions can be used in methods of treating or preventing cancer. Without being bound to a particular theory or mechanism, the inventive TCRs, or the antigen-binding portions thereof, are believed to bind specifically to a mutated amino acid sequence encoded by a cancer-specific mutation, such that the TCR, or the antigen-binding portion thereof, when expressed by a cell, is able to mediate an immune response against a target cell expressing the mutated amino acid sequence. In this regard, the invention provides a method of treating or preventing cancer in a patient, comprising administering to the patient any of the pharmaceutical compositions, TCRs, antigen-binding portions thereof, polypeptides, proteins, nucleic acids, recombinant expression vectors, host cells, or populations of cells described herein, in an amount effective to treat or prevent cancer in the patient.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a patient. Furthermore, the treatment or prevention provided by the inventive method can include treatment or prevention of one or more conditions or symptoms of the cancer being treated or prevented. For example, treatment or prevention can include promoting the regression of a tumor. Also, for purposes herein, "prevention" can encompass delaying the onset of the cancer, or a symptom or condition thereof.

For purposes of the invention, the amount or dose of the inventive TCR material or pharmaceutical composition administered (e.g., numbers of cells when the inventive population of cells is administered) should be sufficient to effect, e.g., a therapeutic or prophylactic response, in the patient over a reasonable time frame. For example, the dose of the inventive TCR material or pharmaceutical composition should be sufficient to bind to a mutated amino acid sequence encoded by a cancer-specific mutation, or detect, treat or prevent cancer in a period of from about 2 hours or longer, e.g., 12 to 24 or more hours, from the time of administration. In certain embodiments, the time period could be even longer. The dose will be determined by the efficacy of the particular inventive TCR material or pharmaceutical composition administered and the condition of the patient, as well as the body weight of the patient to be treated.

Many assays for determining an administered dose are known in the art. For purposes of the invention, an assay, which comprises comparing the extent to which target cells are lysed or IFN-γ is secreted by T cells expressing the inventive TCR, or the antigen-binding portion thereof, or the inventive populations of cells, upon administration of a given dose of such T cells to a mammal among a set of mammals of which is each given a different dose of the cells, could be used to determine a starting dose to be administered to a patient. The extent to which target cells are lysed or IFN-γ is secreted upon administration of a certain dose can be assayed by methods known in the art.

The dose of the inventive TCR material or pharmaceutical composition also will be determined by the existence, nature and extent of any adverse side effects that might accompany the administration of a particular inventive TCR material or pharmaceutical composition. Typically, the attending physician will decide the dosage of the inventive TCR material or pharmaceutical composition with which to treat each individual patient, taking into consideration a variety of factors, such as age, body weight, general health, diet, sex, inventive TCR material or pharmaceutical composition to be administered, route of administration, and the severity of the condition being treated.

In an embodiment in which the inventive population of cells is to be administered, the number of cells administered per infusion may vary, for example, in the range of one million to 200 billion cells; however, amounts below or above this exemplary range are within the scope of the invention. For example, the daily dose of inventive host cells can be about 1 million to about 200 billion cells (e.g., about 5 million cells, about 25 million cells, about 500 million cells, about 1 billion cells, about 5 billion cells, about 20 billion cells, about 30 billion cells, about 40 billion cells, about 60 billion cells, about 80 billion cells, about 100 billion cells, about 120 billion cells, about 130 billion cells, about 150 billion cells, about 160 billion cells, about 170 billion cells, about 180 billion cells, about 190 billion cells, about 200 billion cells, or a range defined by any two of the foregoing values), preferably about 10 million to about 200 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, about 100 billion cells, about 110 billion cells, about 120 billion cells, about 130 billion cells, about 140 billion cells, about 150 billion cells, about 160 billion cells, about 170 billion cells, about 180 billion cells, about 190 billion cells, about 200 billion cells, or a range defined by any two of the foregoing values), more preferably about 100 million cells to about 200 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells, about 50 billion cells, about 75 billion cells, about 90 billion cells, about 100 billion cells, about 110 billion cells, about 120 billion cells, about 130 billion cells, about 140 billion cells, about 150 billion cells, about 160 billion cells, about 170 billion cells, about 180 billion cells, about 190 billion cells, about 200 billion cells, or a range defined by any two of the foregoing values).

For purposes of the inventive methods, wherein populations of cells are administered, the cells can be cells that are allogeneic or autologous to the patient. Preferably, the cells are autologous to the patient.

Another embodiment of the invention provides any of the TCR materials or pharmaceutical compositions described herein for use in treating or preventing cancer in a patient.

The cancer may, advantageously, be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vagina, cancer of the vulva, cholangiocarcinoma, chronic lymphocytic leukemia, chronic myeloid cancer, colon cancer, esophageal cancer, uterine cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, cancer of the oropharynx, ovarian cancer, cancer of the penis, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, cancer of the uterus, ureter cancer, urinary bladder cancer, solid tumors, and liquid tumors. Preferably, the cancer is an epithelial cancer. In an embodiment, the cancer is cholangiocarcinoma, melanoma, colon cancer, or rectal cancer.

The mammal referred to in the inventive methods can be any mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). Preferably, the mammals are from the order Artiodactyla, including Bovines (cows) and Swines (pigs) or of the order Perssodactyla, including Equines (horses). Preferably, the mammals are of the order Primates, Ceboids, or Simoids (monkeys) or of the order Anthropoids (humans and apes). A more preferred mammal is the human. In an especially preferred embodiment, the mammal is the patient expressing the cancer-specific mutation.

In an embodiment of the invention, TCR(s), or antigen-binding portion(s) thereof, may be isolated from the T cells that express PD-1 immediately after separating the T cells that express PD-1 from cells that do not express PD-1. These TCR(s), or antigen-binding portion(s) thereof, may be cloned into a recombinant expression vector, and introduced into host cells to obtain expression of the TCR(s), or antigen binding portion(s) thereof, by the host cells. The host cells that express the TCR(s), or antigen binding portions thereof, could then be screened for antigenic specificity for a mutated amino acid sequence encoded by a cancer-specific mutation.

In this regard, an embodiment of the invention provides a method of isolating T cells having antigenic specificity for a mutated amino acid sequence encoded by a cancer-specific mutation, the method comprising obtaining a first population of PBMCs from a sample of peripheral blood from a patient; selecting T cells that express PD-1 from the bulk population;

separating the T cells that express PD-1 from cells that do not express PD-1 to obtain a T cell population enriched for T cells that express PD-1; isolating nucleotide sequence(s) that encode(s) one or more TCR(s), or antigen-binding portion(s) thereof, from the T cells of the population enriched for T cells that express PD-1; introducing the nucleotide sequence(s) encoding the TCR(s), or antigen binding portion(s) thereof, into further population(s) of PBMCs to obtain T cells that express the TCR(s), or antigen binding portion(s) thereof; identifying one or more genes in the nucleic acid of a cancer cell of the patient, each gene containing a cancer-specific mutation that encodes a mutated amino acid sequence; inducing autologous APCs of the patient to present the mutated amino acid sequence; co-culturing the T cells that express the TCR(s), or antigen binding portion(s) thereof, with the autologous APCs that present the mutated amino acid sequence; and selecting the T cells that (a) were co-cultured with the autologous APCs that present the mutated amino acid sequence and (b) have antigenic specificity for the mutated amino acid sequence presented in the context of a MHC molecule expressed by the patient.

Obtaining a first population of PBMCs from a sample of peripheral blood; selecting T cells that express PD-1; and separating the T cells that express PD-1 from cells that do not express PD-1 may be carried out as described herein with respect to other aspects of the invention.

The method may further comprise isolating nucleotide sequence(s) that encode(s) one or more TCR(s), or antigen binding portion(s) thereof, from the T cells of the population enriched for T cells that express PD-1. While the method may further comprise expanding the numbers of the T cells that express PD-1 prior to isolating the nucleotide sequence, in a preferred embodiment, the method comprises isolating the nucleotide sequence from the T cells without expanding the numbers of the T cells that express PD-1 prior to isolating the nucleotide sequence. For example, the TCR, or antigen binding portion thereof, may be isolated from a single cell. In an embodiment of the invention, the method comprises isolating nucleotide sequence(s) that encode(s) at least one TCR, or antigen binding portion thereof. However, the number of TCR(s), or antigen binding portion(s) thereof, that may be isolated using the inventive methods is not limited and may include more than one TCR(s), or antigen binding portion(s) thereof (for example, about 2, about 3, about 4, about 5, about 10, about 11, about 12, about 13, about 14, about 15, about 20, about 25, about 30, about 40, about 50, about 60, about 70, about 80, about 90, about 100, about 150, about 200, about 400, about 600, about 800, about 1000, about 1500, about 2000 or more, or a range defined by any two of the foregoing values). The nucleotide sequence(s) that encode(s) one or more TCR(s), or antigen binding portion(s) thereof, may otherwise be isolated as described herein with respect to other aspects of the invention.

The method may further comprise introducing the nucleotide sequence(s) encoding the TCR(s), or antigen binding portion(s) thereof, into further population(s) of PBMCs to obtain T cells that express the TCR(s), or antigen binding portion(s) thereof. Each TCR, or antigen binding portion thereof, isolated according to this embodiment of the invention may be introduced into a different population of PBMCs to provide multiple populations of cells, each population of cells expressing a different TCR or antigen binding portion thereof. Introducing the nucleotide sequence(s) encoding the TCR(s), or antigen binding portion(s) thereof, into further population(s) of PBMCs may otherwise be carried out as described herein with respect to other aspects of the invention.

Identifying one or more genes in the nucleic acid of a cancer cell of the patient; inducing APCs of the patient to present the mutated amino acid sequence; co-culturing the T cells with the autologous APCs that present the mutated amino acid sequence; and selecting the T cells that (a) were co-cultured with the autologous APCs that present the mutated amino acid sequence and (b) have antigenic specificity for the mutated amino acid sequence may all be carried out as described herein with respect to other aspects of the invention. In an embodiment of the invention in which more than one TCR, or antigen binding portion thereof, is isolated and a nucleotide sequence encoding each TCR, or antigen binding portion thereof is introduced into a different population of cells, co-culturing may comprise separately co-culturing each population of cells (each expressing a different TCR, or antigen binding portion thereof) with the autologous APCs. Selecting may comprise determining which TCR, or antigen binding portion thereof, has antigenic specificity for the mutated amino acid sequence (e.g., by process of elimination). In an embodiment of the invention, the numbers of selected cells may be expanded as described herein with respect to other aspects of the invention. In an embodiment of the invention, the numbers of selected cells are not expanded.

In an embodiment of the invention, the method may further comprise isolating a nucleotide sequence that encodes a TCR, or an antigen-binding portion thereof, from the selected T cells that have antigenic specificity for the mutated amino acid sequence, wherein the TCR, or the antigen-binding portion thereof, has antigenic specificity for the mutated amino acid sequence. Isolating a nucleotide sequence that encodes a TCR, or an antigen-binding portion thereof, from the selected T cells may be carried out as described herein with respect to other aspects of the invention. Further embodiments of the invention may provide methods of preparing a population of cells that expresses the TCR, or antigen binding portion thereof; a TCR, or an antigen-binding portion thereof, isolated according to the inventive methods; isolated populations of cells prepared according to the inventive methods; pharmaceutical compositions comprising the inventive TCR, or antigen binding portion thereof, or the inventive population of cells; and methods of treating cancer using the inventive compositions, all of which may be as described herein with respect to other aspects of the invention.

The following examples further illustrate the invention but, of course, should not be construed as in any way limiting its scope.

Example 1

This example demonstrates the expression of PD-1 and TIM-3 in the CD8+ cell population in the peripheral blood of a melanoma patient and the purity of the cells separated according to PD-1 and TIM-3.

PBMC from melanoma patient 3713 were rested overnight in the absence of IL-2, stained with antibodies, and sorted according to expression of CD8 and CD3 by FACS. Then, the CD3+CD8+ cells were sorted according to expression of PD-1 and TIM-3 by FACS. The gates of the stained samples were set based on the isotype control. The frequency of the CD8+ PBMC populations expressing each of the markers is indicated in Table 1 below.

TABLE 1

| Population | Phenotype | Percentage of cells expressing indicated phenotype |
|---|---|---|
| Non-specific Staining | TIM-3+PD-1+ | 0.1 |
| | TIM-3−PD-1+ | 4.4 |
| | TIM-3+PD-1− | 1.0 |
| | TIM-3−PD-1− | 94.5 |
| PD-1− | TIM-3+PD-1+ | 0.0 |
| | TIM-3−PD-1+ | 0.0 |
| | TIM-3+PD-1− | 2.0 |
| | TIM-3−PD-1− | 98.0 |
| PD-1+ | TIM-3+PD-1+ | 14.3 |
| | TIM-3−PD-1+ | 77.6 |
| | TIM-3+PD-1− | 2.0 |
| | TIM-3−PD-1− | 6.1 |
| PD-1hi | TIM-3+PD-1+ | 3.3 |
| | TIM-3−PD-1+ | 93.3 |
| | TIM-3+PD-1− | 0.0 |
| | TIM-3−PD-1− | 3.3 |
| TIM-3+ | TIM-3+PD-1+ | 1.9 |
| | TIM-3−PD-1+ | 0.0 |
| | TIM-3+PD-1− | 83.0 |
| | TIM-3−PD-1− | 15.1 |
| PD-1+TIM-3+ | TIM-3+PD-1+ | 83.3 |
| | TIM-3−PD-1+ | 16.7 |
| | TIM-3+PD-1− | 0.0 |
| | TIM-3−PD-1− | 0.0 |

Example 2

This example demonstrates that CD8+PD-1+, CD8+PD-1+TIM-3−, and CD8+PD-1+TIM-3+ cell populations, but not bulk CD8+, CD8+PD-1−, CD8+TIM-3−, or CD8+TIM-3+ cell populations, isolated from peripheral blood recognize target cells pulsed with unique, patient-specific mutated epitopes.

Pheresis from a melanoma patient (3713) was thawed and rested overnight in the absence of cytokines. CD8+ cells were sorted according to PD-1 and TIM-3 expression into the following populations: CD8+ bulk, CD8+PD-1−, CD8+PD-1+, CD8+TIM-3−, CD8+TIM-3+, CD8+PD-1+TIM-3−, and CD8+PD-1+TIM-3+. The numbers of the sorted cells were expanded in vitro for 15 days. On day 15, the cells were washed and co-cultured with target autologous B cells pulsed with wild type (wt) or mutated (mut) epitopes known to be recognized by the patient's tumor-infiltrating lymphocytes at a ratio of 2×10⁴ effector cells: 1×10⁵ B cells. T cells were also co-cultured with the autologous tumor cell line (TC3713) in the absence or presence of HLA-I blocking antibody W6/32 or with an allogeneic tumor cell line (TC3903). T cells were also co-cultured with anti-CD3 antibody as a control. Reactivity was assessed by quantifying IFN-gamma spots 16 hours (h) after the co-culture by IFN-γ ELISpot. The results are shown in Tables 2A and 2B.

As shown in Tables 2A and 2B, CD8+PD-1+, CD8+PD-1+TIM-3−, and CD8+PD-1+TIM-3+ cell populations, but not bulk CD8+, CD8+PD-1−, CD8+TIM-3−, or CD8+TIM-3+ cell populations, isolated from peripheral blood recognized target cells pulsed with unique, patient-specific mutated epitopes.

TABLE 2A

| | Number of IFN-γ spots measured per 2 × 10⁴ effector cells in each blood-derived CD8+ subset | | |
|---|---|---|---|
| Epitope | CD8+ | CD8+PD-1− | CD8+PD-1+ |
| No target | 1 | 1 | 2 |
| CEF peptide pool | 72 | 58 | 4 |
| WDR wt | 1 | 4 | 0 |
| WDR mut | 5 | 0 | >750 |
| SRPX wt | 2 | 2 | 1 |
| SRPX mut | 11 | 1 | 77 |
| AFMID wt | 3 | 1 | 61 |
| AFMID mut | 3 | 1 | 246 |
| HELZ2 wt | 3 | 2 | 9 |
| HELZ2 mut | 0 | 1 | 219 |
| PLSCR4 wt | 1 | 2 | 0 |
| PLSCR4 mut | 5 | 1 | 2 |
| GCN1L1 wt | 2 | 1 | 2 |
| GCN1L1 mut | 2 | 0 | 5 |
| CENPL wt | 1 | 0 | 0 |
| CENPL mut | 3 | 1 | >750 |
| AHNAK wt | 1 | 0 | 2 |
| AHNAK mut | 1 | 0 | 5 |
| TC3713 | 17 | 24 | >750 |
| TC3713 + W6/32 | 0 | 0 | 44 |
| TC3903 | 8 | 11 | 9 |
| Anti-CD3 | >750 | >750 | >750 |

TABLE 2B

| | Number of IFN-γ spots measured per 2 × 10⁴ effector cells in each blood-derived CD8+ subset | | | |
|---|---|---|---|---|
| Epitope | CD8+TIM-3− | CD8+TIM-3+ | CD8+PD-1+TIM-3− | CD8+PD-1+TIM-3+ |
| No target | 0 | 0 | 0 | 0 |
| CEF peptide pool | 40 | 8 | 25 | 1 |
| WDR wt | 1 | 3 | 5 | 0 |
| WDR mut | 1 | 0 | 257 | 2 |
| SRPX wt | 4 | 1 | 14 | 2 |
| SRPX mut | 3 | 2 | 381 | 104 |
| AFMID wt | 2 | 0 | 59 | 2 |
| AFMID mut | 2 | 1 | 88 | 1 |
| HELZ2 wt | 4 | 0 | 21 | 20 |
| HELZ2 mut | 3 | 0 | 465 | 341 |
| PLSCR4 wt | 0 | 0 | 11 | 0 |
| PLSCR4 mut | 2 | 0 | 5 | 0 |
| GCN1L1 wt | 2 | 1 | 6 | 0 |
| GCN1L1 mut | 1 | 1 | 10 | 2 |
| CENPL wt | 2 | 1 | 8 | 0 |
| CENPL mut | 2 | 1 | 53 | 1 |
| AHNAK wt | 4 | 0 | 4 | 0 |
| AHNAK mut | 0 | 22 | 12 | 1 |
| TC3713 | 7 | 76 | >750 | >750 |
| TC3713 + W6/32 | 0 | 2 | 85 | 17 |
| TC3903 | 18 | 12 | 22 | 1 |
| Anti-CD3 | >750 | >750 | >750 | >750 |

Example 3

This example demonstrates that CD8+PD-1+, CD8+PD-1+TIM-3−, CD8+PD-1+TIM-3+, and CD8+PD-1+CD27hi cell populations, but not bulk CD8+, CD8+TIM-3−, CD8+TIM-3+, CD8+PD-1−CD27hi, or CD8+PD-1− cell populations, isolated from peripheral blood recognize target cells electroporated with RNA encoding unique, patient-specific mutated epitopes.

Pheresis from melanoma patient 3903 was thawed and rested overnight in the absence of cytokines. CD8+ cells were enriched by bead separation and then sorted according to PD-1 and TIM-3 expression into the following populations: CD8+ bulk, CD8+PD-1−, CD8+PD-1+, CD8+TIM- 3−, CD8+TIM-3+, CD8+PD-1+TIM-3−, CD8+PD-1+TIM-3+, CD8+PD-1-CD27hi, and CD8+PD-1+CD27hi. The numbers of sorted cells were expanded in vitro for 15 days. On day 15, the cells were washed and co-cultured with target autologous dendritic cells electroporated with RNA encoding mutated tandem minigenes (TMGs 1-26; each encoding multiple 25mers containing a mutation flanked by the endogenous sequence) identified by exome sequencing of a tumor from patient 3903. The effector cells were co-cultured with the target cells at a ratio of $2\times10^4$ effector cells: to about $1\times10^5$ DCs. The effector cells were also co-cultured with the autologous tumor cell line (TC3903) or with an allogeneic tumor cell line (TC3903). Reactivity was assessed by quantifying IFN-gamma spots 16 h after the co-culture by IFN-γ ELISpot. The results are shown in Tables 3A-3C.

As shown in Tables 3A-3C, CD8+PD-1+, CD8+PD-1+TIM-3−, CD8+PD-1+TIM-3+, and CD8+PD-1+CD27hi cell populations, but not bulk CD8+, CD8+TIM-3−, CD8+TIM-3+, CD8+PD-1-CD27hi, or CD8+PD-1− cell populations, isolated from peripheral blood recognized target cells electroporated with RNA encoding unique, patient-specific mutated epitopes. In melanoma patient 3903, CD8+ PBL subsets expressing PD-1 were enriched in cells recognizing TMG-9 (Tables 2A-2B). In this patient, further enrichment in mutation-specific cells from peripheral blood was observed when selecting CD8+ cells expressing PD-1 in combination with TIM-3 or CD27 (TMG-8, TMG-3, and weaker recognition of TMG-7 and TMG-11) (Tables 3A-3C).

CD8+ lymphocytes expressing PD-1 in the peripheral blood of patient 3903 were enriched in cells capable of recognizing the autologous tumor cell line (Tables 3A-3C).

The sorted cells were also co-cultured with autologous DCs electroporated with RNA encoding full-length MART-1, GP100, tyrosinase, NY-ESO-1, MAGE-A3, or SSX2. CD8+ lymphocytes expressing PD-1 in the peripheral blood of patient 3903 also recognized mutation-specific cells and cancer germline antigens SSX2 and MAGE-A3.

TABLE 3A

| | Number of IFN-γ spots measured per $2 \times 10^4$ effector cells in each blood-derived CD8+ subset | | |
|---|---|---|---|
| Epitope | CD8+ | CD8+PD-1− | CD8+PD-1+ |
| No target | 0 | 0 | 0 |
| CEF peptide pool | 44 | 119 | >500 |
| irrelevant TMG | 0 | 1 | 1 |
| TMG-1 | 0 | 0 | 0 |
| TMG-2 | 0 | 3 | 1 |
| TMG-3 | 4 | 5 | 0 |
| TMG-4 | 9 | 1 | 3 |
| TMG-5 | 9 | 1 | 1 |
| TMG-6 | 22 | 2 | 6 |
| TMG-7 | 2 | 1 | 0 |
| TMG-8 | 7 | 4 | 15 |
| TMG-9 | 9 | 0 | 303 |
| TMG-10 | 1 | 1 | 0 |
| TMG-11 | 8 | 2 | 29 |
| TMG-12 | 11 | 5 | 11 |
| TMG-13 | 1 | 2 | 2 |
| TMG-14 | 9 | 21 | 1 |
| TMG-15 | 3 | 12 | 40 |
| TMG-16 | 0 | 0 | 0 |
| TMG-17 | 2 | 3 | 2 |
| TMG-18 | 4 | 1 | 0 |
| TMG-19 | 0 | 3 | 0 |
| TMG-20 | 1 | 1 | 1 |
| TMG-21 | 0 | 2 | 1 |
| TMG-22 | 2 | 3 | 3 |
| TMG-23 | 0 | 0 | 1 |
| TMG-24 | 0 | 1 | 12 |
| TMG-25 | 0 | 4 | 17 |
| TMG-26 | 1 | 0 | 3 |
| DMSO | 0 | 0 | 0 |
| Peptide Nos 8-2 | 1 | 1 | 9 |
| Peptide nos. 9-4 | 3 | 0 | >500 |
| TC3903 | 2 | 0 | >500 |
| TC3713 | 41 | 17 | 12 |
| Anti-CD3 1 μg/ml | >500 | >500 | >500 |

TABLE 3B

| | Number of IFN-γ spots measured per $2 \times 10^4$ effector cells in each blood-derived CD8+ subset | | | |
|---|---|---|---|---|
| Epitope | CD8+TIM-3− | CD8+TIM-3+ | CD8+PD-1+TIM-3− | CD8+PD-1+TIM-3+ |
| No target | 0 | 0 | 0 | 0 |
| CEF peptide pool | 35 | 7 | 280 | 0 |
| irrelevant TMG | 3 | 23 | 0 | 4 |
| TMG-1 | 3 | 3 | 1 | 3 |
| TMG-2 | 5. | 13 | 3 | 3 |
| TMG-3 | 1 | 17 | 3 | 6 |
| TMG-4 | 3 | 15 | 0 | 3 |
| TMG-5 | 2 | 17 | 7 | 50 |
| TMG-6 | 0 | 9 | 2 | 0 |
| TMG-7 | 4 | 14 | 8 | 224 |
| TMG-8 | 3 | 0 | 79 | >500 |
| TMG-9 | 9 | 11 | 639 | 426 |
| TMG-10 | 3 | 1 | 1 | 4 |
| TMG-11 | 18 | 0 | 38 | 204 |
| TMG-12 | 11 | 51 | 24 | 63 |
| TMG-13 | 2 | 21 | 3 | 1 |
| TMG-14 | 27 | 57 | 11 | 0 |
| TMG-15 | 5 | 35 | 4 | 16 |
| TMG-16 | 3 | 15 | 2 | 1 |
| TMG-17 | 2 | 28 | 2 | 8 |
| TMG-18 | 1 | 26 | 5 | 19 |
| TMG-19 | 0 | 8 | 0 | 0 |
| TMG-20 | 1 | 16 | 1 | 0 |
| TMG-21 | 1 | 9 | 1 | 0 |
| TMG-22 | 3 | 22 | 4 | 4 |
| TMG-23 | 1 | 4 | 4 | 2 |
| TMG-24 | 3 | 13 | 34 | 9 |
| TMG-25 | 8 | 22 | 3 | 2 |
| TMG-26 | 0 | 7 | 0 | 0 |
| DMSO | 0 | 0 | 2 | 0 |
| Peptide Nos 8-2 | 2 | 27 | 70 | >500 |
| Peptide nos. 9-4 | 0 | 2 | >500 | 10 |
| TC3903 | 1 | 34 | 227 | 365 |
| TC3713 | 13 | 1 | 3. | 109 |
| Anti-CD3 1 μg/ml | >500 | >500 | >500 | >500 |

TABLE 3C

| Epitopes | Number of IFN-γ spots measured per $2 \times 10^4$ effector cells in each blood-derived CD8+ subset | |
|---|---|---|
| | CD8+PD-1−CD27hi | CD8+PD-1+CD27hi |
| No target | 0 | 0 |
| CEF peptide pool | 79 | 422 |
| irrelevant TMG | 6 | 2 |
| TMG-1 | 2 | 0 |
| TMG-2 | 2 | 3 |
| TMG-3 | 8 | 306 |
| TMG-4 | 4 | 0 |
| TMG-5 | 3 | 8 |
| TMG-6 | 2 | 0 |
| TMG-7 | 3 | 0 |
| TMG-8 | 7 | 82 |
| TMG-9 | 4 | 395 |
| TMG-10 | 0 | 21 |
| TMG-11 | 1 | 52 |
| TMG-12 | 5 | 12 |
| TMG-13 | 1 | 5 |
| TMG-14 | 5 | 4 |
| TMG-15 | 9 | 7 |
| TMG-16 | 3 | 0 |
| TMG-17 | 1 | 2 |
| TMG-18 | 0 | 22 |
| TMG-19 | 0 | 0 |
| TMG-20 | 1 | 0 |
| TMG-21 | 3 | 1 |
| TMG-22 | 1 | 1 |
| TMG-23 | 0 | 0 |
| TMG-24 | 2 | 0 |
| TMG-25 | 2 | 0 |
| TMG-26 | 2 | 0 |
| DMSO | 1 | 0 |
| Peptide Nos 8-2 | 0 | 58 |
| Peptide nos. 9-4 | 0 | 401 |
| TC3903 | 0 | >500 |
| TC3713 | 1 | 13 |
| Anti-CD3 1 μg/ml | 222 | 303 |

Example 4

This example demonstrates that CD8+PD-1+, CD8+PD-1hi, CD8+PD-1+TIM-3+, CD8+PD-1+CD27hi, and CD8+PD-1+CD27− cell populations, but not bulk CD8+, CD8+TIM-3−, CD8+TIM-3+, or CD8+PD-1− cell populations, isolated from peripheral blood recognize target cells electroporated with RNA encoding unique, patient-specific mutated epitopes.

Pheresis from melanoma patient 3784 was thawed and rested overnight in the absence of cytokines. CD8+ cells were enriched by bead separation and then sorted according to PD-1 and TIM-3 expression into the following populations: CD8+ bulk, CD8+PD-1−, CD8+PD-1+, CD8+PD-1hi, CD8+TIM-3−, CD8+TIM-3+, CD8+PD-1+TIM-3+, CD8+PD-1+CD27hi, and CD8+PD-1+CD27−. The numbers of sorted cells were expanded in vitro for 15 days. On day 15, the cells were washed and co-cultured with target autologous dendritic cells electroporated with RNA encoding mutated tandem minigenes (TMGs 1-9; each encoding multiple 25mers containing a mutation flanked by the endogenous sequence) identified by exome sequencing of a tumor from patient 3784. The effector cells were co-cultured with the target cells at a ratio of $2 \times 10^4$ effector cells: to about $1 \times 10^5$ DCs. The effector cells were also co-cultured with autologous DCs electroporated with RNA encoding epitopes for cytomegalovirus (CMV), Epstein-Barr virus (EBV), FLU (CEF), or an irrelevant TMG. T cells were also co-cultured with the autologous tumor cell line (TC3784) or with an allogeneic tumor cell line (TC3903). Reactivity was assessed by quantifying IFN-gamma spots 16 h after the co-culture by IFN-γ ELISpot.

The results are shown in Tables 4A-4C. As shown in Tables 4A-4C, CD8+PD-1+, CD8+PD-1hi, CD8+PD-1+TIM-3+, CD8+PD-1+CD27hi, and CD8+PD-1+CD27− cell populations, but not bulk CD8+, CD8+TIM-3−, CD8+TIM-3+, or CD8+PD-1− cell populations, isolated from peripheral blood recognized target cells electroporated with RNA encoding unique, patient-specific mutated epitopes.

In this patient, the peripheral blood CD8+ lymphocytes expressing PD-1 were enriched in mutation-specific cells recognizing up to three antigens (TMG-3, TMG-5, and TMG-8). Peripheral blood CD8+PD-1+ and PD-1hi T cells also recognized gp100.

Further separation of peripheral blood CD8+PD-1+ lymphocytes into CD27hi or CD27− separated the lymphocytes recognizing TMG-3 from those recognizing TMG-5 and TMG-8.

The co-culture of the sorted cells with the autologous tumor cell line or the allogeneic tumor cell line revealed that peripheral blood CD8+ lymphocytes expressing PD-1 alone or in combination with TIM-3 or CD27 were enriched in tumor-reactive cells.

TABLE 4A

| Epitope | Number of IFN-γ spots measured per $2 \times 10^4$ effector cells in each blood-derived CD8+ subset | | | |
|---|---|---|---|---|
| | CD8+ | CD8+PD-1− | CD8+PD-1+ | CD8+PD-1hi |
| No target | 0 | 0 | 0 | 0 |
| CEF peptide pool | 259 | 138 | 10. | 57 |
| irrelevant TMG | 18 | 3 | 11 | 14 |
| TMG-1 | 11 | 0 | 4 | 6 |
| TMG-2 | 7 | 0 | 6 | 4 |
| TMG-3 | 14 | 0 | 77 | 291 |
| TMG-4 | 7 | 0 | 9 | 39 |
| TMG-5 | 7 | 2 | 88 | 77 |
| TMG-6 | 24 | 2 | 3 | 10 |
| TMG-7 | 11 | 1 | 9 | 2 |
| TMG-8 | 18 | 0 | 217 | 111 |
| TMG-9 | 13 | 0 | 6 | 8 |
| MART-1 | 5 | 1 | 48 | 7 |
| GP100 | 27 | 1 | 154 | 418 |
| TYR | 17 | 2 | 9 | 6 |
| MAGE-A3 | 14 | 2 | 29 | 156 |
| NY-ESO-1 | 9 | 0 | 6 | 33 |
| SSX2 | 16 | 0 | 0 | 33 |
| TC3784 | 120 | 41 | 491 | >500 |
| TC3903 | 22 | 18 | 129 | 212 |
| Anti-CD3 | >500 | 424 | >500 | >500 |

TABLE 4B

| Epitope | Number of IFN-γ spots measured per 2 × 10$^4$ effector cells in each blood-derived CD8+ subset | | | | |
|---|---|---|---|---|---|
| | CD8+TIM-3− | CD8+TIM-3+ | CD8+PD-1+TIM-3+ | CD8+PD-1+CD27hi | CD8+PD-1+CD27− |
| No target | 2 | 0 | 0 | 0 | 1 |
| CEF peptide pool | 152 | 27 | 3 | 4 | 45 |
| irrelevant TMG | 1 | 2 | 6 | 6 | 10 |
| TMG-1 | 0 | 2 | 0 | 0 | 11 |
| TMG-2 | 0 | 1 | 2 | 2 | 4 |
| TMG-3 | 1 | 0 | 98 | 12 | 276 |
| TMG-4 | 1 | 1 | 2 | 1 | 3 |
| TMG-5 | 0 | 2 | 87 | 319 | 3 |
| TMG-6 | 0 | 1 | 3 | 1 | 4 |
| TMG-7 | 0 | 0 | 6 | 0 | 3 |
| TMG-8 | 5 | 1 | 402 | 175 | 5 |
| TMG-9 | 0 | 0 | 2 | 4 | 2 |
| MART-1 | 3 | 24 | 3 | 0 | 222 |
| GP100 | 11 | 36 | >500 | 362 | 381 |
| TYR | 2 | 0 | 7 | 3 | 6 |
| MAGE-A3 | 1 | 0 | 304 | 91 | 6 |
| NY-ESO-1 | 3 | 3 | 15 | 6 | 23 |
| SSX2 | 1 | 1 | 16 | 4 | 5 |
| TC3784 | 100 | 292 | >500 | 500 | 223 |
| TC3903 | 30 | 23 | 26 | 177 | 76 |
| Anti-CD3 | 482 | 489 | >500 | 492 | >500 |

Example 5

This example demonstrates that CD8+PD-1+ and CD8+PD-1hi cell populations, but not bulk CD8+ or CD8+PD-1− cell populations, isolated from peripheral blood recognize target cells electroporated with RNA encoding unique, patient-specific mutated epitopes.

Pheresis from a colorectal cancer patient 3971 was thawed and rested overnight in the absence of cytokines. CD8+ cells were enriched by bead separation and then sorted according to PD-1 expression into the following populations: CD8+ bulk, CD8+PD-1−, CD8+PD-1+, and CD8+PD-1hi. The numbers of sorted cells were expanded in vitro for 15 days. On day 15, the cells were washed and co-cultured with target autologous dendritic cells electroporated with RNA encoding mutated tandem minigenes (TMGs 1-9; each encoding multiple 25mers containing a mutation flanked by the endogenous sequence) identified by exome sequencing from the patient's tumor (at a ratio of 2×10$^4$ effector cells: about 1×10$^5$ DCs). TMG-1 encoded mutated CASP8 peptide. The cells were also co-cultured with cells electroporated with RNA encoding a mock (empty) control vector or irrelevant TMG. Reactivity was assessed by quantifying IFN-gamma spots 16 h after the co-culture by IFN-γ ELISpot. The results are shown in Table 5. As shown in Table 5, CD8+PD-1+ and CD8+PD-4hi cell populations, but not bulk CD8+ or CD8+PD-1− cell populations, isolated from peripheral blood recognized target cells electroporated with TMG-1 or TMG-3 RNA.

TABLE 5

| Epitope | Number of IFN-γ spots measured per 2 × 10$^4$ effector cells in each blood-derived CD8+ subset | | | |
|---|---|---|---|---|
| | CD8+ | CD8+PD-1− | CD8+PD-1+ | CD8+PD-1hi |
| No target | 0 | 0 | 0 | 0 |
| irrelevant TMG | 1 | 1 | 0 | 0 |
| TMG-1 | 2 | 7 | 41 | 277 |
| TMG-2 | 0 | 0 | 0 | 0 |
| TMG-3 | 2 | 0 | 3 | 175 |
| TMG-4 | 1 | 2 | 1 | 0 |
| TMG-5 | 0 | 0 | 0 | 0 |
| TMG-6 | 2 | 3 | 7 | 0 |
| TMG-7 | 0 | 1 | 1 | 0 |
| TMG-8 | 0 | 1 | 0 | 0 |
| TMG-9 | 0 | 0 | 1 | 1 |
| Anti-CD3 | >500 | >500 | >500 | >500 |

Example 6

This example demonstrates the isolation of a nucleotide sequence encoding a TCR having antigenic specificity for target cells electroporated with RNA encoding unique, patient-specific mutated epitopes from a CD8+PD-1hi cell population.

The TMG-1 and TMG-3 reactive cells present in the CD8+PD-1hi cell population of Example 5 (colorectal cancer patient) were selected by FACS based on the upregulation of 4-1BB (CD137). On day 15, PD-1hi bulk cells, as well as CD137−, and CD137+ fractions, were co-cultured with target DCs electroporated with RNA encoding for TMG-1 or TMG-3, or plate-bound OKT3. Reactivity was assessed by CD137 upregulation after 20 h. The number of cells and the percentage of cells (with respect to bulk cells) having the indicated phenotype are shown in Table 6A.

TABLE 6A

| Target cells co-cultured with CD8+PD-1hi cells | Gated on live cells, single cells, CD3+CD8+ cells | | |
|---|---|---|---|
| | Irrelevant TMG | TMG-1 | TMG-3 |
| CD137− | 99.8 ($1.7 \times 10^5$ cells) | 99.1 ($1.7 \times 10^5$ cells) | 99.2 ($1.7 \times 10^5$ cells) |
| CD137+ | 0.0 | 0.3 (634 cells) | 0.2 (489 cells) |

The numbers of cells in Table 6A were expanded in vitro for 14 days. The cell yields obtained are shown in Table 6B.

TABLE 6B

| Target cells co-cultured with CD8+PD-1hi cells | Irrelevant TMG | TMG-1 | TMG-3 |
|---|---|---|---|
| CD137− | $1.4 \times 10^8$ | $1.8 \times 10^8$ | $1.4 \times 10^8$ |
| CD137+ | — | $8.5 \times 10^7$ | $7.8 \times 10^7$ |

A nucleotide sequence encoding a TCR was isolated from the TMG-1 and TMG-3 reactive cells that were selected on the basis of CD137 upregulation. The CD137+ TMG-1 reactive cells (>97% one clonotype) comprised an alpha chain CDR3 amino acid sequence of CAVRDRGTGGFK-TIF (SEQ ID NO: 1) and a beta chain CDR3 amino acid sequence of CASITKDRAYEQYF (SEQ ID NO: 2). The CD137+ TMG-3 reactive cells (>93% one clonotype) comprised an alpha chain CDR3 amino acid sequence of CAYR-SASDMRF (SEQ ID NO: 3) and a beta chain CDR3 amino acid sequence of CASSPETGGISEQYF (SEQ ID NO: 4).

Accordingly, the selection of CD137+ cells that were reactive against target cells electroporated with TMG-1 or TMG-3 from CD8+PD-1hi lymphocytes sorted from the peripheral blood led to the generation of highly enriched TMG-1 and TMG-3 specific populations, each encoding for one dominant TCR.

Example 7

This example demonstrates the identification of the mutation recognized by TMG-1 reactive cells isolated from CD8+PD-1+ peripheral blood cells.

Following 15 days in culture, the sorted TMG-1-reactive, CD137− and CD137+ effector populations of Example 6 were co-cultured with autologous DCs that were electroporated with TMG-1 RNA or were pulsed with wild type or mutated CASP8 minimal epitopes. Reactivity was assessed by quantifying IFN-gamma spots 16 h after the co-culture by IFN-γ ELISpot. The resulting numbers of IFN-γ spots measured per $2\times10^4$ cells are shown in Table 7.

TABLE 7

| | Sorted vs TMG-1 | | |
|---|---|---|---|
| | PD-1hi bulk | CD137− | CD137+ |
| No target | 0 | 0.0 | 0 |
| irrelevant TMG | 0 | 0 | 0 |
| TMG-1 | 120 | 11 | >500 |
| wt CASP8 | 0 | 0 | 1 |
| mut CASP8 | 70 | 14 | >500 |
| anti-CD3 | >500 | >500 | >500 |

As shown in Table 7, the TMG-1 reactive cells enriched from peripheral blood recognized a unique mutation in CASP8 identified through exome sequencing of 3971 tumor.

Example 8

This example demonstrates the identification of the mutation recognized by TMG-3 reactive cells isolated from CD8+PD-1+ peripheral blood cells.

Following 15 days in culture, the sorted TMG-3-reactive, CD137− and CD137+ effector cell populations of Example 6 were co-cultured with autologous DCs that were pulsed with mutated long peptides (μg/ml) derived from TMG-3 (Nos. 1-16 in Table 8). Reactivity was assessed by quantifying IFN-gamma spots 16 h after the co-culture by IFN-γ ELISpot. The resulting numbers of IFN-γ spots measured per $2\times10^4$ cells are shown in Table 8.

TABLE 8

| | Sorted vs. TMG-3 | | |
|---|---|---|---|
| Long peptide# | CD8+PD-1hi bulk | CD137− | CD137+ |
| DMSO | 0 | 0 | 0 |
| 1 | 61 | 21 | >500 |
| 2 | 0 | 1 | 0 |
| 3 | 1 | 0 | 2 |
| 4 | 0 | 0 | 4 |
| 5 | 2 | 0 | 1 |
| 6 | 0 | 0 | 0 |
| 7 | 1 | 0 | 4 |
| 8 | 0 | 0 | 2 |
| 9 | 0 | 0 | 1 |
| 10 | 0 | 0 | 1 |
| 11 | 0 | 0 | 0 |
| 12 | 0 | 0 | 0 |
| 13 | 0 | 0 | 0 |
| 14 | 0 | 0 | 0 |
| 15 | 0 | 0 | 1 |
| 16 | 0 | 0 | 1 |
| Anti-CD3 1 μg/ml | >500 | >500 | >500 |

As shown in Table 8, the TMG-3 reactive cells enriched from CD8+PD-hi population selected from peripheral blood recognized long peptide TMG-3 number 1, which encoded a mutated HISTH3B peptide.

Example 9

This example demonstrates the reactivity of PBL engineered to express the mutated CASP8 peptide specific T-cell receptor isolated in Example 6.

PBL were transduced with the nucleotide sequence encoding the TMG-1 specific TCR of Example 6 or an empty vector (control). Autologous B cells were pulsed for 2 h with either wild type or mutated CASP8 peptides. The pulsed cells were co-cultured with TCR transduced or vector transduced cells (at a ratio of $2\times10^5$ B cells: $2\times10^4$ effector cells). Reactivity was measured by 4-1BB upregulation 24 h later. The frequency of 4-1BB within the CD3+CD8+ cells is shown in FIG. 1. As shown in FIG. 1, PBL engineered to express the CASP8 mut specific T-cell receptor isolated in Example 6 were reactive against the mutated CASP8 peptide.

Example 10

This example demonstrates that CD8+PD-1+ and CD8+PD-1hi cell populations, but not bulk CD8+ or CD8+PD-1− cell populations, isolated from peripheral blood recognize target cells pulsed with unique, patient-specific mutated epitopes. This example also demonstrates that CD4+PD-1+ and CD4+PD-1hi cell populations, but not bulk CD4+ or CD4+PD-1− cell populations, isolated from peripheral blood recognize target cells electroporated with RNA encoding NY-ESO-1.

Pheresis from a melanoma patient (3998) was thawed and rested overnight in the absence of cytokines. CD8+ cells were sorted according to PD-1 expression into the following populations: CD8+ bulk, CD8+PD-1−, CD8+PD-1+, and CD8+PD-1hi as described in Example 2. CD4+ cells were sorted according to PD-1 expression into the following populations: CD4+ bulk, CD4+PD-1−, CD4+PD-1+, and CD4+PD-1hi as described in Example 2. The numbers of the sorted cells were expanded in vitro for 15 days. On day 15, the cells were washed and co-cultured with target autologous DCs electroporated with RNA encoding mutated tandem minigenes (TMGs 1-7; each encoding multiple 25mers containing a mutation flanked by the endogenous sequence) identified by exome sequencing of a tumor from patient 3998, or RNA encoding MART-1, gp100, tyrosinase, NY-ESO-1, MAGE-A3, or SSX2. The cells were also co-cultured with autologous tumor cell line or allogeneic tumor cell line (3713). T cells were also co-cultured with anti-CD3 antibody as a control. Reactivity was assessed by quantifying IFN-gamma spots 16 hours (h) after the co-culture by IFN-γ ELISpot. The results are shown in Tables 9A and 9B.

As shown in Table 9A, the CD8+PD-1+ and CD8+PD-1hi cell populations, but not bulk CD8+ or CD8+PD-1− cell populations, isolated from peripheral blood recognized target cells electroporated with RNA encoding with unique, patient-specific mutated epitopes (TMG-1). As shown in Table 9A, the CD8+PD-1hi cell population, but not bulk CD8+, CD8+PD-1+, or CD8+PD-1− cell populations, isolated from peripheral blood recognized target cells electroporated with RNA encoding with unique, patient-specific mutated epitopes (TMG-3). The CD8+PD-1+ and CD8+PD-1hi cell populations isolated from peripheral blood recognized target cells electroporated with RNA encoding NY-ESO-1 (Table 9A).

TABLE 9A

Cells isolated from Pheresis of 3998

|  | CD8+ | CD8+PD-1− | CD8+PD-1+ | CD8+PD-1hi |
|---|---|---|---|---|
| No target | 0 | 1 | 0 | 0 |
| Irrel. TMG | 2 | 15 | 1 | 0 |
| CEF | 84 | 43 | 53 | 39 |
| TMG-1 | 67 | 34 | 394 | 478 |
| TMG-2 | 11 | 15 | 6 | 4 |
| TMG-3 | 16 | 7 | 56 | 159 |
| TMG-4 | 4 | 24 | 7 | 0 |
| TMG-5 | 4 | 4 | 36 | 11 |
| TMG-6 | 0 | 5 | 2 | 0 |
| TMG-7 | 9 | 19 | 2 | 1 |
| MART-1 | 3 | 11 | 2 | 2 |
| GP-100 | 11 | 28 | 16 | 5 |
| Tyrosinase | 11 | 15 | 3 | 8 |
| NY-ESO-1 | 179 | 34 | >500 | >500 |
| MAGE-A3 | 6 | 6 | 6 | 0 |
| SSX2 | 12 | 13 | 9 | 24 |
| TC3998 | 110 | 63 | >500 | >500 |
| TC3713 | 215 | 229 | 150 | 10 |
| Anti-CD3 1 μg/ml | >500 | >500 | >500 | >500 |

TABLE 9B

Cells isolated from Pheresis of 3998

|  | CD4+ | CD4+PD-1− | CD4+PD-1+ | CD4+PD-1hi |
|---|---|---|---|---|
| No target | 3 | 0 | 0 | 3 |
| Irrel. TMG | 1 | 30 | 35 | 6 |
| CEF | 8 | 6 | 36 | 6 |
| TMG-1 | 26 | 20 | 12 | 11 |
| TMG-2 | 14 | 20 | 14 | 14 |
| TMG-3 | 26 | 15 | 21 | 20 |
| TMG-4 | 30 | 29 | 19 | 6 |
| TMG-5 | 5 | 6 | 17 | 8 |
| TMG-6 | 3 | 9 | 6 | 8 |
| TMG-7 | 24 | 24 | 12 | 4 |
| MART-1 | 56 | 17 | 13 | 6 |
| GP-100 | 14 | 25 | 24 | 18 |
| Tyrosinase | 29 | 24 | 36 | 7 |
| NY-ESO-1 | 42 | 29 | 320 | >500 |
| MAGE-A3 | 13 | 19 | 13 | 17 |
| SSX2 | 24 | 20 | 14 | 10 |
| TC3998 | 22 | 16 | 170. | 84 |
| TC3713 | 34 | 57 | 16 | 15 |
| Anti-CD3 1 μg/ml | >500 | >500 | >500 | >500 |

As shown in Table 9B, CD4+PD-1+ and CD4+PD-1hi cell populations, but not bulk CD4+ or CD4+PD-1− cell populations, isolated from peripheral blood recognized target cells electroporated with RNA encoding NY-ESO-1.

Examples 11-17

The following materials and methods were employed for the experiments described in Examples 11-17.

Subjects, Tumor Biopsies, and PBMCs.

Leukapheresis products, and tumor samples were obtained from individuals with stage IV melanoma enrolled on a clinical protocol (03-C-0277), approved by the institutional-review board (IRB) of the National Cancer Institute (NCI). Informed consent was obtained from all subjects, and they all had progressive disease at the time of sample acquisition. The 5 individuals studied in detail were chosen on the basis of availability of pre-treatment leukapheresis, and matched frozen fresh tumor to perform whole-exome sequencing and transcriptome analysis. Patients were either treatment naïve (NCI-3998), or had undergone prior therapies including surgery, chemotherapy, and immunotherapy (NCI-3713, 3784, 3903, and 3926). The patient characteristics are provided in Table 10. The patients that received prior therapies had been last treated from 7-55 months before the leukapheresis product was obtained. A summary of the individuals included in the phenotypic characterization of circulating and tumor-infiltrating lymphocytes is provided in Table 11. Melanoma specimens were surgically resected and digested into single cell suspensions using the GENTLEMACS Dissociator (Miltenyi Biotec, Gladbach, Germany) as described in Gros et al., J. Clin. Invest., 124: 2246-2259 (2014), and cryopreserved. Peripheral blood mononuclear cells (PBMC) were obtained by leukapheresis, prepared over a Ficoll-Hypaque gradient (LSMTM; MP Biomedicals, Santa Ana, Calif.), and cryopreserved until analysis. Melanoma cell lines were established from enzymatically separated tumor cells cultured in RPMI 1640 supplemented with 10% FBS (HyClone Defined, Logan, Utah) at 37° C. and 5% $CO_2$. Melanoma cell lines were mycoplasma negative, and were authenticated based on the identification of patient-specific somatic mutations, and HLA molecules.

TABLE 10

| Patient | Cancer type | Prior therapy | Months from end of last therapy to leukapheresis (mo) | % PD-1+ (of CD8+) PBMC | # putative mutations[d] | Mutations evaluated[e] |
|---|---|---|---|---|---|---|
| 3713 | Mel[a] | IL-2, anti-CTLA-4 | 7 mo | 4.1% | 4359 | 7 minimal epitopes |
| 3998 | Mel | No treatment | — | 1.9% | 279 | 115 (TMG#1-7) |
| 3784 | Mel | Surgery, IFN | 14 mo | 2.1% | 440 | 140 (TMG1-9) |
| 3903 | Mel | Surgery, MART-F5 TCR[b] | 55 mo | 3.4% | 414 | 308 (TMG#1-26) |
| 3926 | Mel | IL-2, surgery, chemo.[c] | 8 mo | 7.4% | 346 | 128 (TMG#1-11) |
| 3759 | Mel | Surgery, IFN | 1 mo | 1.0% | n.d.[f] | n.e.[g] |
| 3992 | Mel | Anti-PD-1, anti-CTLA-4 | 5 mo | 8% | n.d. | n.e. |

[a]Melanoma;
[b]Adoptive transfer of autologous T cells that were gene-engineered to express a MART-1 HLA-A*0201-restricted T-cell receptor.
[c]Chemotherapy patient 3926: dacarbazine and vinblastine.
[d]Putative non-synonymous mutations were defined by: >2 exome variant reads, ≥10% variant frequency in the exome, ≥10 normal reads, and tumor/normal variant frequency ≥5. Common single nucleotide polymorphisms were filtered.
[e]Mutations evaluated were selected based on whole-exome and transcriptome analysis.
[f]Not deteremined.
[g]Not evaluated.

TABLE 11

| Variable/trait | Total (%) |
|---|---|
| Total no. patients | 18 |
| Sex | |
| Male | 14 (78) |
| Female | 4 (22) |
| Age | |
| 31-40 | 4 (22) |
| 41-50 | 3 (17) |
| 51-60 | 9 (50) |
| 61-70 | 2 (11) |
| Prior Treatment | |
| Surgery | 17 (94) |
| Chemotherapy | 2 (11) |
| Radiotherapy | 2 (11) |
| Immunotherapy | 12 (67) |
| Any 2 or more | 13 (72) |
| Any 3 or more | 8 (44) |
| No treatment | 1 (5) |

Exome and RNA sequencing.

Tumor biopsies and normal PBMC were subjected to DNA extraction, library construction, exome capture of approximately 20,000 coding genes, and next-generation sequencing by Macrogen (Rockville, Md.), Personal Genome Diagnostics (PGDX, Baltimore, Md.), or the Broad Institute (Cambridge, Mass.). The average number of distinct high quality sequences at each base ranged between 100 and 150 for the individual exome libraries. Alignments and variant calling were performed, as described in Tran et al., Science, 344: 641-645 (2014). The total number of putative non-synonymous mutations (Table 10) was determined using filters consisting of >2 exome variant reads, ≥10% variant allele frequency (VAF) in the tumor exome, >10 normal reads, tumor/normal variant frequency ≥5, and filtering out single nucleotide polymorphisms in dbSNP build 138. An mRNA sequencing library was also prepared from a tumor biopsy using Illumina TRUSEQ RNA library prep kit. RNA alignment was performed using STAR (Dobin et al., Bioinformatics, 29: 15-21 (2013)) duplicates, were marked using picard's MARKDUPLICATE tools, and FPKM values were calculated using cufflinks (Trapnell et al., Nature Biotechnol., 8: 511-515 (2010)). The levels of transcripts encoding putative non-synonymous variants, calculated as fragments per kilobase per million mapped reads (FPKM), were used to assess expression of candidate mutations identified using whole exome data.

The following criteria were used to prioritize mutations for immunological screening (Table 12). Initially, mutations with a variant allele frequency (VAF)>10% in the tumor exome, as well as mutations that were identified in both transcriptome and exome analysis without any additional filters, were selected. For some samples (NCI-3903), the mutations selected based on exome only were prioritized by selecting those with >10 variant reads to increase the confidence of mutation calling. For each of the immunogenic antigens detected, the amino acid changes are specified.

TABLE 12

| Patient | TMG# | Mutation Type | Gene | WT AA | Mut AA | AA position | Wt 25-mer | Mut 25-mer |
|---|---|---|---|---|---|---|---|---|
| 3998 | TMG1 | SNV | MAGEA6 | E | K | 168 | DSLQLVFGIELME VDPIGHVYIFAT (SEQ ID NO: 80) | DSLQLVFGIELMK VDPIGHVYIFAT (SEQ ID NO: 77) |

TABLE 12-continued

| Patient | TMG# | Mutation Type | Gene | WT AA | Mut AA | AA position | Wt 25-mer | Mut 25-mer |
|---------|------|---------------|------|-------|--------|-------------|-----------|------------|
| 3998 | TMG3 | SNV | PDS5A | Y | F | 1000 | MATEKLLSLLPEYVVPYMIHLLAHD PDFTRSQ (SEQ ID NO: 81) | MATEKLLSLLPEFVVPYMIYLLAHD PDFTRSQ (SEQ ID NO: 78) |
|  |  |  |  | H | Y | 1007 |  |  |
| 3998 | TMG5 | SNV | MED13 | P | S | 1691 | PHIKSTVSVQIIPCQYLLQPVKHED (SEQ ID NO: 82) | PHIKSTVSVQIISCQYLLQPVKHED (SEQ ID NO: 79) |

Antibodies, and Phenotypic Characterization of T Cells.

Fluorescently labeled antibodies were purchased from BD Biosciences, San Jose, Calif. (UCHT1, 1.6:100, CD3 PE-CF594; SK7, 1:100, CD3 APC-Cy7; SK1, 0.5:100, CD8 PE-Cy7; 4B4-1, 1.25:100, CD137 APC; NK-1, 3:100, CD57 FITC; J168-540, 1.2:100, BTLA PE), eBioscience, San Diego, Calif. (H57-597, 0.5:100, mTCRB FITC; 0323, 2:100, CD27 BV605), Biolegend, San Diego, Calif. (EH12.2H7, 0.7:100, PD-1 BV421), R&D Systems, Minneapolis, Minn. (344823, 2.6:100, TIM-3 PE and APC), Enzo Life Sciences, Farmingdale, N.Y. (17B4. 1:100, LAG-3 FITC) and Miltenyi Biotec (4B4-1, 2.6:100, 4-1BB PE). Anti-PD-1 antibody was from Amplimmune (Gaithersburg, Md., AMP-514, 1/300, PD-1 Alexa Fluor 647). Cell-sorting experiments were carried out using anti-PD-1 AMP-514 antibody.

To perform the phenotypic characterization, PBMC and tumor single cell suspensions were thawed into T-cell media (1:1 mix of AIMV media [Life Technologies, Waltham, Mass.] and RPMI 1640 media [Lonza, Walkersville, Md.], 5% in-house human serum, 100 U/ml penicillin and 100 μg/ml streptomycin [Life Technologies], 2 mM L-glutamine [Life Technologies], 10 μg/ml gentamicin [Quality Biological Inc., Gaithersburg, Md.], 12.5 mM HEPES [Life Technologies]) supplemented with DNAse (Genentech Inc. San Francisco, Calif., 1:1000), centrifuged, and plated at 2e6 cells/well in a 24-well plate in the absence of cytokines. After resting the cells overnight at 37° C. and 5% $CO_2$, cells were harvested, and 2e6 cells were resuspended in 50 μl of staining buffer (PBS, 0.5% BSA, 2 mM EDTA) containing antibodies. Cells were incubated for 30 minutes at 4° C. and washed twice prior to acquisition. Flow cytometry acquisition was carried out on a modified FORTESSA analyzer, equipped to detect 18 fluorescence parameters, or CANTO II flow cytometers (BD Biosciences). Flow cytometry data were analyzed using FLOWJO software (Ashland, Oreg.). Data were gated on live cells (PI negative), single cells. Gates were set based on fluorescence minus one (FMO) controls.

T-Cell Sorting and In Vitro Expansion.

Cell-sorting was carried out using the BD JAZZ cell sorter (BD Biosciences). For all experiments requiring cell-sorting from PBMC, CD8$^+$ cells were first enriched using CD8 microbeads (Miltenyi), and stained as described above in "Antibodies, and phenotypic characterization of T cells." When sorting T cells from fresh tumor single cell suspensions, this pre-enrichment step was not performed. Cells were gated on live (PI negative), single cells, CD3$^+$, and CD8$^+$ cells, and on the population of interest. Half of the T cells isolated were spun and snap frozen to perform TRB deep sequencing, and the other half were expanded in vitro. T-cell yields ranged from $3 \times 10^3$ to $3 \times 10^5$. A similar sorting strategy was used to sort the 4-1BB$^+$ lymphocytes, following a 20 h co-culture.

T cells were expanded in vitro using an excess of irradiated allogeneic feeders cells (5000 rad) pooled from three donors in T-cell media supplemented with 30 ng/ml anti-CD3 (OKT3, Miltenyi Biotec) and 3000 IU of IL-2 (Aldesleukin, Chiron). After day 6, half of the media was replaced with fresh T-cell media containing IL-2 every other day. At day 15, T cells were either used in co-culture assays or cryopreserved, until future analysis. Of note, enrichment of mutation-specific T cells was consistent between replicate CD8$^{30}$PD-1$^+$ T cell cultures, but stochastic outgrowth or loss of T cell reactivities can be observed and become more apparent when starting with less than $3 \times 10^3$ CD8$^+$PD-1$^+$ T cells. The minimum material required to sort $3 \times 10^3$ CD8$^+$ PD-1$^+$ cells is approximately $1 \times 10^7$ PBMC.

Generation of Autologous Antigen Presenting Cells (APCs).

Immature dendritic cells (CD11c$^+$, CD14$^-$, CD80$^{low}$, CD86$^+$ and HLA-DR$^+$) were generated from PBMC using the plastic adherence method, as described in Tran et al., Science, 344: 641-645 (2014). On day 3, DC media was added, and at day 5-6 DCs were harvested and used in electroporation experiments or cryopreserved. DC media comprised of RPMI supplemented with 5% human serum, 100 U/ml penicillin and 100 μg/ml streptomycin, 2 mM L-glutamine (Life Technologies), 800 IU/ml GM-CSF and 200 U/ml IL-4 (Peprotech, Rocky Hill, N.J.). When used after cryopreservation, cells were thawed into DC media, spun at 1000 RPM for 10 min, resuspended in DC media at $2 \times 10^6$ cells/ml, and incubated at 37° C. and 5% $CO_2$ for 2 h, prior to electroporation or peptide pulsing.

Autologous B cells were isolated from autologous PBMC by positive selection using CD19$^+$ microbeads (Miltenyi Biotec) and expanded using irradiated NIH3T3 CD40L cells and IL-4 (Peprotech), as described in Tran et al., Science, 344: 641-645 (2014). B cells were harvested at day 5-6 after the initial stimulation, and either re-stimulated, cryopreserved, or used in co-culture assays. When used after cryopreservation, B cells were thawed into B cell media 16-24 h prior to using them in co-culture assays. B cell media comprised of IMDM media (Quality Biological Inc., Gaithersburg, Md.) supplemented with 10% human serum, 100 U/ml penicillin and 100 μg/ml streptomycin, 2 mM L-glutamine, and 200 U/ml IL-4 (Peprotech, Rocky Hill, N.J.).

Construction of TMGs, and In Vitro Transcription of TMG RNA.

Tandem minigenes (TMGs) were constructed as described in Lu et al., Clin. Cancer Res., 20: 3401-3410 (2014); Tran et al., Science, 344: 641-645 (2014). Briefly, a minigene was constructed for each non-synonymous variant identified, composed of the mutated amino acid flanked by 12 amino acids of the wild-type protein sequence. Up to 16 minigenes were strung together to generate a tandem minigene (TMG) construct. These TMG constructs were codon optimized and cloned in frame into pcRNA2SL using EcoRI and BamHI. pcRNA2SL is based on the pcDNA3.1, and was modified to include a signal sequence and a DC-LAMP trafficking sequence to enhance processing and presentation (Wu et al., *PNAS*, 92: 11671-11675 (1995)). The sequences were verified by ranger sequencing. Following linearization of the constructs, phenol chloroform extraction was performed and DNA was precipitated with sodium acetate and ethanol. Next, 1 µg of linearized DNA was used to generate in vitro transcribed RNA using the MMESSAGE MMACHINE T7 Ultra kit (Life Technologies), as instructed by the manufacturer. RNA was precipitated using $LiCl_2$, and resuspended at 1 µg/µl. To screen for recognition of cancer germline antigens NY-ESO-1, MAGEA3 and SSX2, and melanoma differentiation antigens MART1, GP100 and TYROSINASE, full-length amino acid sequences were cloned individually into pcRNA2SL using EcoRI and BamHI, and these constructs were used to generate IVT RNA.

Transfection of RNA or DNA.

DCs were resuspended in Opti-MEM (Life Technologies) at $10\text{-}40 \times 10^6$ cells/ml. 8 µg of IVT RNA was aliquoted into the bottom of a 2 mm gap electroporation cuvette, and 100 µl of DCs were added. DCs were electroporated with 150 V, 10 ms, and 1 pulse, using a BTX-830 square wave electroporator (Holliston, Mass.). Cells were gently resuspended into DC media and transferred into ultra-low attachment polysterene 24-well plate (corning) at approximately $1 \times 10^6$ DCs/ml, and rested overnight at 37° C., 5% $CO_2$. Transfection efficiencies were routinely between 70-90% assessed with a control GFP RNA (not shown). In co-culture assays, the irrelevant TMG RNA control was a random TMG from a different patient.

HLA alleles were cloned into pcDNA3.1. To interrogate which HLA alleles presented the neo-antigens identified, COST cells were co-transfected with TMG DNA constructs and plasmids encoding the individual HLA molecules using LIPOFECTAMINE 2000 reagent (Life Technologies). After 16 h, cells were harvested and used as targets in co-culture assays.

HLA-I Alleles, Peptide Prediction and Pulsing.

HLA was determined from next generation sequencing data using the algorithm PHLAT (Bai et al., BMC Genomics, 15: 325 (2014)). (NCI-3713: HLA-A*02:01, A*29:02, B*44:03, B*51:01, C*15:02, C*16:01. NCI-3998: HLA-A*01:01, A*30:02, B*15:01, B*18:01, C*03:03, C*05:01. NCI-3784: HLA-A*01:01, A*03:01, B*07:02, C*07:02. NCI-3903: HLA-A*02:01, A*24:02, B*27:02, B*38:01, C*02:02, C*12:03. NCI-3926: HLA-A*01:01, A*02:01, B*08:01, B*13:02, C*06:02, C*07:01).

Candidate 8 to 11-mers containing the mutated residues that were predicted to bind with high affinity to the patients' HLA-I molecules were identified using the immune epitope database (IEDB) (Vita et al., *Nucleic Acids Res.*, 43: D405-412 (2015)). Crude and HPLC peptides were synthesized by GenScript (Piscataway, N.J.), and resuspended in DMSO at 10 mg/ml and stored at −20° C.

For experiments requiring peptide pulsing, DCs or B cells were resuspended in DC or B cell media, respectively, at 1e6 cells/ml. DCs were incubated overnight at 37° C. and 5% $CO_2$ with wild-type or mutated 25-mers at a concentration of 10 µg/ml in DC media. B cells were pulsed with 1 µg/ml or with 10-fold serial dilutions of minimal epitopes starting at 10 µg/ml for 2 h at 37° C. and 5% $CO_2$. DCs or B cells were washed once with PBS prior to co-incubation with T cells.

Co-Culture Assays: IFN-γ ELISPOT, and Flow Cytometry Detection of Activation Marker 4-1BB.

Both IFN-γ enzyme-linked immunospot assay (ELISPOT) and 4-1BB upregulation at 20 h after the co-culture were used to measure target cell recognition by T cells. After 15 days of T-cell expansion, or following overnight rest of cryopreserved T cells in T cell media supplemented with 3000 IU/ml IL-2, T cells were washed to remove excess cytokines. In the ELISPOT assays, $2 \times 10^4$ T cells were added per well in a 96-well plate. When DCs electroporated with IVT RNA encoding for TMGs or shared antigens were used as targets, approximately $3\text{-}7 \times 10^4$ cells/well were used in a 96-well plate. When peptide-pulsed B cells were used, $8 \times 10^4$ to $1.5 \times 10^5$ cells were added per well. All co-cultures were carried out in T-cell media in the absence of exogenously added cytokines. T cells cultured alone or stimulated with plate bound anti-CD3 (OKT3) were used as controls in all the assays. CEF RNA encoding for epitopes derived from CMV, EBV, and Flu (CEF) were included as controls in all the immunological screening assays (Nielsen et al., *J. Immunol., Meth.*, 360: 149-156 (2010)).

IFN-γ ELISPOT assays were carried out as described in Tran et al., *Science*, 344: 641-645 (2014). The raw data were plotted without subtracting the background. Greater than 40 spots, and greater than twice the background was considered positive T cell reactivity. Prior to processing the ELISPOT assay, cells were harvested for flow-cytometry detection of 4-1BB upregulation, as described in Tran et al., *Science*, 344: 641-645 (2014).

TCR Deep Sequencing and Analysis.

TCR-α (TRA) and TCR-β (TRB) deep sequencing were performed on genomic DNA by Adaptive Biotechnologies (Seattle, Wash.). For the enriched populations of TMG-reactive cells, DNA was extracted from 1 e6 lymphocytes. The number of circulating and tumor-resident $CD8^+$ lymphocytes that were sequenced ranged from $3 \times 10^3$ to $3 \times 10^5$. The coverage per sample was >10×. Only productive TCR rearrangements were used in the calculations of TCR frequencies and TRB overlap. Analysis of TRB overlap of CDR3 nucleotide sequences between two given populations was calculated using an IMMUNOSEQ analyzer (Adaptive Biotechnologies, Seattle, Wash.) using the following formula: sample TRB overlap=[shared sequence reads in A+shared sequence reads in B]/Σsequence reads in (A+B). Weighing in the frequency of the shared sequences rather than the total number of shared sequences helped account for potentially different sized samples. A TRB overlap of 1 represents 100% overlap between two populations.

Retroviral Vector Construction, Production and Transduction of T cells.

For NCI-3998, TCRs were constructed by pairing the dominant TRA and TRB chains, and for each population the TCRs were designated based on the rank of the TRA and TRB (TCR A rank #/B rank #) within the population sequenced. In total, 2 TCRs were assembled from the TMG1 ($MAGEA6_{E>K}$)-reactive population (TCR A1/B1, TCR A1/B2), and 4 TCRs from the TMG3 ($PDS5A_{Y>F;\ H>Y}$)-reactive, as well as the TMG5 ($MED13_{P>S}$)-reactive populations (TCR A1/B1, TCR A1/B2, TCR A2B1, TCR A2/B2). Briefly, TRA V-J regions and TRB V-D-J regions were fused to the mouse constant TCR-alpha and beta chains (Cohen et al., *Cancer Res.*, 66: 8878-8886 (2006)), respectively. Mouse constant regions were modified, as described in (Cohen et al., *Cancer Res.*, 67: 3898-3903 (2007); Haga-Friedman et al., *J. Immunol.*, 188: 5538-5546 (2012). The full-length TCRB and TCRA chains were cloned, in this orientation, into pMSGV1 retroviral vector separated by a furin SGSG P2A linker (GenScript). For all TCRs, the amino acid residue at position 2 of the beta chain was changed from a glycine to an alanine in order to facilitate cloning into the vector.

Transient retroviral supernatants were generated, and autologous PBMCs were transduced as described in Tran et al., Science, 344: 641-645 (2014). Transduced T cells were used at day 15 or cryopreserved until used. GFP and mock transduced T cells were used as controls in all transduction experiments.

Statistical Analysis.

Data were reported as the median, mean±SEM, or mean±SD, as specified. The Mann-Whitney test was used to compare the percentage of PD-1 expression between PBMC and fresh tumor single cell suspensions. Dunn's test for multiple comparisons was used to analyze the statistical differences in TRB overlap. Statistical analysis was carried out using PRISM program 6.0 (GRAPHPAD Software Inc., La Jolla, Calif.). Unless otherwise specified, experiments were performed without duplicates. All data are representative of at least 2 experiments.

Example 11

This example demonstrates the expression of PD-1 on peripheral blood and tumor-infiltrating CD8$^+$ T cells in patients with melanoma.

The expression of PD-1 on peripheral blood and tumor-infiltrating CD8$^+$ T cells was compared. PD-1 expression accounted for approximately 36% of the CD8$^+$ TIL population, but matched peripheral blood samples from the same individuals contained only a median of 4.1% CD8$^+$PD-1$^+$ cells. Moreover, circulating CD8$^+$ lymphocytes had limited co-expression of the inhibitory and co-stimulatory cell surface receptors PD-1, TIM-3, LAG-3 and 4-1BB compared to tumor-resident CD8$^+$ lymphocytes. Thus, few PD-1-expressing circulating CD8$^+$ lymphocytes are present in patients with melanoma.

Example 12

This example demonstrates the screening of circulating in vitro expanded CD8$^+$ cells from melanoma patients for recognition of mutations.

It was next examined whether selection of circulating CD8+PD-1+ lymphocytes was able to prospectively identify neoantigen-specific CD8+ T cells in the blood of four individuals with melanoma. A high-throughput personalized screening strategy capable of evaluating T cell reactivity to neoantigens presented on all of the HLA restriction elements of the individual was used. Briefly, mutations selected on the basis of tumor-exome and transcriptome analyses were incorporated into oligonucleotides (minigenes) that encoded a 25-residue peptide (25-mer), and these oligonucleotides were then concatenated to yield tandem minigenes (TMGs; designated in numerical order and for each patient). Each TMG encoded up to 16 minigenes, and the requisite number of TMGs that allowed for the expression of all of the mutant 25-mers that were identified were constructed.

In parallel, CD8$^+$ lymphocytes were separated from pre-treatment peripheral blood mononuclear cells (PBMCs) into CD8$^+$, CD8$^+$PD-1$^-$, CD8$^+$PD-1$^+$, and CD8$^+$PD-1$^{hi}$ (defined as the top 20% of PD-1-expressing CD8$^+$ T cells), and expanded for 15 days. In vitro transcribed TMG RNA was electroporated into immature autologous dendritic cells (DCs) that were employed as targets in a T cell co-culture assay. Using this approach, the circulating in vitro expanded CD8$^+$ subsets from 4 individuals with metastatic melanoma (patients NCI-3998, NCI-3784, NCI-3903, and NCI-3926, see Table 10) were screened for recognition of 115, 140, 308, and 128 mutations, respectively.

Example 13

This example demonstrates the detection of mutation-reactive lymphocytes within the CD8$^+$PD-1$^+$ subset of Example 12.

Although the unseparated peripheral blood CD8+ cells, as well as the CD8+PD-1− lymphocytes, from NCI-3998 showed limited recognition of the mutant 25-mers encoded by TMG1 (hereafter referred to as recognition of TMG1 or TMG1 reactive), the circulating CD8+PD-1+ lymphocyte subset showed enhanced TMG1 reactivity and low, but reproducible, reactivity to TMG3 and TMG5. Based on upregulation of the activation marker 4-1BB, the frequency of CD8+PD-1+ cells that were reactive to DCs expressing these TMG-encoded peptides was 1.8% for TMG1, 0.5% for TMG3 and 0.3% for TMG5. Additionally, recognition of TMG1 and TMG3 by the CD8+PD-1$^{hi}$ subset was also observed. Similarly, CD8+PD-1+ and CD8+PD-1$^{hi}$, but not CD8+ or CD8+PD-1+, lymphocytes from the peripheral blood of subjects NCI-3784 and NCI-3903 showed T cell reactivity to neoantigens. Circulating CD8$^+$PD-1$^+$ cells from NCI-3784 recognized at least three neo-antigens encoded by TMG3, TMG5 and TMG8, and peripheral blood CD8$^+$PD-1$^+$ lymphocytes isolated from NCI-3903 detected at least one neo-antigen expressed by TMG9. NCI-3926 peripheral blood lymphocytes did not show T-cell reactivity to any of the neo-antigens screened. Overall, circulating mutation-reactive lymphocytes were prospectively identified in 3 of 4 melanoma patients evaluated, and these cells were consistently detected within the CD8$^+$PD-1$^+$ lymphocytes. Notably, with the exception of NCI-3998, who displayed low level recognition of TMG1 in the unseparated population of circulating CD8$^+$ T cells, selection of CD8$^+$PD-1$^+$ or PD-1$^{hi}$ lymphocytes from the blood of the patients was necessary to expose CD8+ T cell reactivity to neoantigens.

Example 14

This example demonstrates the isolation of TCRs from the mutation-reactive lymphocytes of Example 13.

The specific neo-antigens targeted by the mutation-reactive lymphocytes were next analyzed. Given the low frequency of some of the reactivities, and the polyclonal nature of the circulating PD-1$^+$ subset, TMG-reactive cells were enriched by selecting 4-1BB$^+$ lymphocytes following a co-culture with specific TMGs, expanding them in vitro, and co-incubating them with DCs individually pulsed with the mutated 25-mers encoded by the corresponding TMG (Table 12). In a representative example, TMG1−, TMG3− and TMG5− reactive cells isolated from the circulating CD8+PD-1+ subset of subject NCI-3998 showed reactivity to neoantigens derived from mutations in the genes MAGE family member A6 (MAGEA6), PDS5 cohesion-associated factor A (PDS5A) and mediator complex subunit 13 (MED13) (which are referred to as MAGEA6$_{E>K}$, PDS5A$_{Y>F;H>Y}$ and MED13$_{P>S}$, respectively). The minimal predicted epitopes were determined, synthesized, and tested, and the TMG-reactive cells demonstrated specific recognition of the mutated neo-epitopes over the wild-type counterparts. The HLA alleles presenting the neo-antigens were also identified. Although MAGEA6$_{E>K}$ and PDS5A$_{Y>F;H>Y}$ were presented by the alleles encoding HLA-A*30:02 and HLA-C*03:03, respectively, recognition of the MED13$_{P>S}$ neo-epitope was restricted to alleles encoding HLA-A*30:02 and HLA-B*15:01. Deep-sequencing analyses of the variable V-J or V-D-J region of the TRA and TRB genes (which encode the hypervariable regions of the TCR-α and TCR-β chains that are important for peptide recognition by the TCR) of the enriched populations of neoantigen-specific CD8+ T cells revealed multiple dominant TRA and TRB sequences that were unique for each of the T cell populations. To study the specificity of the mutation-specific cells at the clonal level, TCRs were constructed by pairing the sequences encoding the 2 most dominant TRA and TRB CDR3 sequences (Linnemann et al., Nature Med., 19: 1534-1541 (2013)) from the MAGEA6$_{E>K}$, PDS5A$_{Y>F;H>Y}$, or the MED13$_{P>S}$ neo-antigen specific lymphocytes, and cloning them into retroviral vectors used to transduce autologous PBMCs. The full-length alpha and beta chain amino acid sequences encoded by the vectors are shown in Table 13. The two TCRs constructed by pairing the most dominant and the second most dominant TRA and TRB sequences (which are referred to as TCR A1/B1 and TCR A2/B2) from the MAGEA6$_{E>K}$-reactive population displayed MAGEA6$_{E>K}$ recognition, based on 4-1BB upregulation against the mutated MAGEA6$_{E>K}$ minimal epitope. Four TCRs (TCR A1/B1, TCR A1/B2, TCR A2/B1, TCR A2/B2) were assembled for each of the remaining MED13$_{P>S}$ and PDS5A$_{Y>F;H>Y}$-specific lymphocyte populations. Two of the four potential MED13$_{P>S}$-specific TCR-expressing lymphocytes tested, TCRA1/B1 and TCRA2/B2, recognized the MED13$_{P>S}$ mutated 25-mer peptide and recognition of MED13$_{P>S}$ was restricted to HLA-B*15:01 and HLA-A*30:02, respectively. Finally, out of four PDS5A$_{Y>F;H>Y}$ TCRs constructed and screened, one single TCR displayed specific recognition of TMG3 and the PDS5A$_{Y>F;H>Y}$ neo-epitope.

mutated antigens derived from TIL also existed in the blood of Patient 3713 prior to TIL therapy.

Patient NCI-3713 experienced a complete tumor regression following administration of TIL-3713. Previous studies showed that TIL-3713 derived from a lung metastasis recognized multiple mutated neo-epitopes including WDR46$_{T>I}$, SRPX$_{P>L}$, AFMID$_{A>V}$, HELZ2$_{D>N}$, CENPL$_{P>L}$, AHNAK$_{S>F}$, and PRDX3$_{P>L}$. Analysis of the pre-treatment PBMCs from this patient demonstrated recognition of 6 of 7 neo-epitopes tested (recognizing WDR46$_{T>I}$, SRPX$_{P>L}$, AFMID$_{A>V}$, HELZ2$_{D>N}$, CENPL$_{P>L}$, and PRDX3$_{P>L}$, but not AHNAK$_{S>F}$). Reactivity was uniquely identified within the circulating CD8$^+$ PD-1$^+$ and CD8+PD-1$^{hi}$, but not the CD8$^+$ or the CD8$^+$PD-1$^+$ lymphocytes. T-cell reactivities observed were mutation-specific, as they displayed preferential recognition of the mutated over the wild-type peptides, and the percentage of neo-antigen-specific cells based on 4-1BB up-regulation ranged from 0.5% to up to 21% of the CD8$^+$PD-1$^{hi}$ cells. Thus, selection of circulating CD8$^+$PD-1$^+$ lymphocytes revealed that the T-cell response to mutated antigens derived from TIL also existed in the blood of this patient prior to TIL therapy.

Example 16

This example demonstrates the recognition of autologous tumor by the enriched populations of mutation-specific T cells and T-cell receptors isolated in Example 14.

In view of their potential use to treat cancer, the recognition of autologous tumor by the enriched populations of mutation-specific T cells and T-cell receptors isolated was next examined. MAGEA6$_{E>K}$, PDS5A$_{Y>F;H>Y}$, or the MED13$_{P>S}$ TCR-transduced T cells from NCI-3998, and mutation-specific CD8$^+$ T cells derived from the blood of

TABLE 13

| Reactivity | TRA rank/TRB rank (T-cell population of origin) | TRAV/TRAJ | TCR alpha chain sequence | TRBV/TRBJ | TCR beta chain sequence |
|---|---|---|---|---|---|
| MAGEA6$^{E168K}$ | A1/B1 (TMG1 enriched) | TRAV21*01/ TRAJ21*01F | SEQ ID NO: 51 | TRBV7-3*01/ TRBJ1-2*01 | SEQ ID NO: 52 |
| MAGEA6$^{E168K}$ | A2/B2 (TMG1 enriched) | TRAV39*01/ TRAJ58*01 | SEQ ID NO: 53 | TRBV7-6*01/ TRBJ1-2*01 | SEQ ID NO: 54 |
| PDS5A$_{Y1000F; H1007Y}$ | A1/B2 (TMG3-enriched) | TRAV38-1*01/ TRAJ53*01 | SEQ ID NO: 55 | TRBV27*01/ TRBJ2-2*01 | SEQ ID NO: 56 |
| MED13$_{P1691S}$ | A1/B1 (TMG5-enriched) | TRAV12-1*01/ TRAJ27*01 | SEQ ID NO: 57 | TRBV9*01/ TRBJ2-1*01 | SEQ ID NO: 58 |
| MED13$_{P1691S}$ | A2/B2 (TMG5-enriched) | TRAV12-2*01/ TRAJ29*01 | SEQ ID NO: 59 | TRBV27*01/ TRBJ2-7*01 | SEQ ID NO: 60 |

In NCI-3784, peripheral blood neo-antigen specific responses were identified for three mutated antigens FLNA$_{R>C}$, KIF16B$_{L>P}$, and SON$_{R>C}$ presented by HLA-B*07:02. Moreover, circulating CD8$^+$PD-1$^+$ lymphocytes reactive against TMG9 from NCI-3903 displayed mutation-specific recognition of KIF1BP$_{P>S}$ 8-mer presented by HLA-B*38:01, and this population contained 3 dominant TRB clonotypes. Thus, selection of circulating CD8$^+$PD-1$^+$ lymphocytes led to the prospective identification of a diverse mutation-specific T-cell response in 3 of 4 melanoma patients tested, with 3, 3, and 1 unique, patient-specific neo-antigens recognized, respectively.

Example 15

Figure 2A:
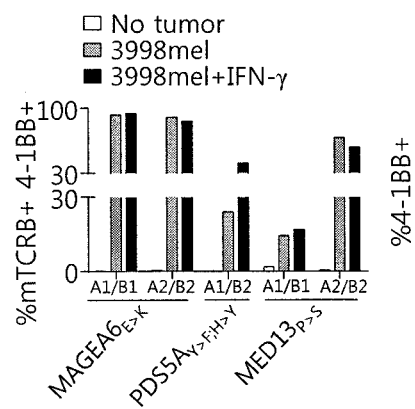
FIG. 2A is a graph showing the reactivity (as determined by 4-1BB upregulation on CD3+CD8+ cells) of retrovirally transduced lymphocytes from subject NCI-3998 expressing MAGEA6$_{E>K}$, PDS5A$_{Y>F;H>Y}$, and MED13$_{P>S}$-specific TCRs against the autologous tumor cell line 3998 mel.
Figure 2B:
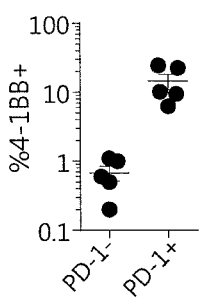
FIG. 2B is a graph showing the reactivity of the circulating CD8+PD-1− and CD8+PD-1+ lymphocytes against their autologous tumor cell line. Frequency of 4-1BB on CD3+ cells is shown (mean±SEM).

This example demonstrates that selection of circulating CD8+PD-1+ lymphocytes reveals that the T-cell response to NCI-3784, and 3903 recognized their corresponding autologous tumor cell line at variable levels (FIG. 2A), either with or without pre-treatment of the autologous tumor cell lines with IFN-γ, which can enhance processing and presentation of epitopes on HLA molecules. Furthermore, in all 5 individuals studied, the circulating CD8$^+$PD-1$^+$, but not the CD8$^+$PD-1$^-$ cells, displayed direct tumor recognition, as evidenced by detection of 4-1BB up-regulation (FIG. 2B) and IFN-γ release. The frequency of tumor-reactive cells within the circulating CD8$^+$PD-1$^+$ lymphocytes ranged from 6.3% to 24.6%. Circulating CD8$^+$PD-1$^+$ cells from NCI-3926 did not recognize any of the mutated antigens tested, but recognized autologous tumor. Additionally, the percentage of tumor-reactive CD8$^+$PD-1$^+$ lymphocytes from NCI-3998 and 3784 (9.5%, and 24.6%, respectively) exceeded that observed against the neo-antigens evaluated, suggesting that either additional neo-antigens or non-mutated tumor antigens may be recognized by the circulating CD8+PD-1+ subset. Indeed, in all four patients evaluated, the circulating CD8+PD-1+ and or CD8+PD-1$^{hi}$ cells also displayed recognition of one or more cancer germline antigens or melanoma differentiation antigens tested, including NY-ESO-1, MAGEA3, SSX2, MART1, GP100 and TYR. While the peripheral blood CD8+PD-1+ T cells from NCI-3903 recognized SSX2, circulating CD8+PD-1+ T-cell subsets derived from NCI-3926 and NCI-3998 recognized NY-ESO-1, and the CD8+PD-1$^{hi}$ lymphocytes from NCI-3784 displayed reactivity against MAGEA3, and GP100. MART1 and TYR were not recognized by any of the CD8+ T-cell subsets tested. The relative frequency of circulating CD8+PD-1+ T cells targeting mutated antigens and self-antigens was highly variable from patient to patient. The relative frequency of circulating CD8+PD-1+ T cells targeting mutated antigens and self-antigens for representative Patient 3998 is shown in Table 14.

TABLE 14

|  | Peripheral blood | | | | Tumor | |
| --- | --- | --- | --- | --- | --- | --- |
|  | CD8+PD-1+ | | CD8+PD-1hi | | CD8+PD-1+ | |
|  | % 4-1BB+ | % of total reactivities detected | % 4-1BB+ | % of total reactivities detected | % 4-1BB+ | % of total reactivities detected |
| MAGEA6$_{E168K}$ (TMG1) | 2.4 | 10.0 | 2.9 | 8.8 | 3.8 | 30.1 |
| PDS5A$_{Y1000F; H1007Y}$ (TMG3) | 0.6 | 2.5 | 0.5 | 1.5 | 0.2 | 1.6 |
|  | 0.3 | 1.3 | N.D. | N.D. | 0.9 | 7.4 |
| MED13$_{P1691S}$ (TMG5) | 3.3 | 13.8 | 3.4 | 10.3 | 4.9 | 40.2 |
| Mutated antigens | 20.7 | 86.2 | 29.7 | 89.7 | 7.3 | 59.8 |
| NY-ESO-1 | 20.7 | 86.2 | 29.7 | 89.7 | 7.3 | 59.8 |
| Self-antigens |  |  |  |  |  |  |
| 3998mel | 9.5 |  | 7.2 |  |  | 11.2 |

Example 17

This example demonstrates the characteristics of the CD8+PD-1+ lymphocytes of Examples 11-16.

Figure 2C:
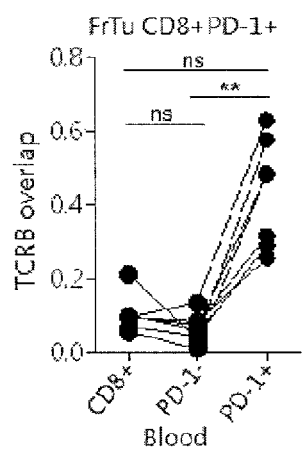
FIG. 2C is a graph showing the TCRB overlap between the tumor-resident CD8$^+$PD-1$^+$ cells, and the blood-derived CD8$^{30}$, CD8$^+$PD-1$^-$, and CD8$^+$PD-1$^+$ cells. TCRB overlap of 1 indicates 100% similarity between two populations. n.s. not significant, **P<0.01 using Dunn's test for multiple comparisons.

The findings in Examples 11-16 indicated that circulating CD8+PD-1+ lymphocytes were enriched in cancer mutation-specific cells as well as other tumor-specific T cells. Additionally, simultaneous screening of matched circulating and tumor-resident CD8+PD-1+ lymphocytes in 4 patients revealed a high degree of similarity in the tumor antigens targeted by both populations. In concordance, TRB deep sequencing of matched tumor-resident and circulating lymphocytes in the absence of in vitro expansion manifested a relatively high degree of overlap between TRB repertoires of the tumor-infiltrating and circulating CD8+PD-1+ subsets, but far less with the circulating CD8+ or CD8+PD-1− (FIG. 2C). The specific antigens recognized by the circulating CD8+PD-1+ lymphocytes and the TIL infusion product these patients received were also similar.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated or purified nucleic acid comprising a nucleotide sequence encoding a TCR, or an antigen-binding portion thereof, wherein the TCR, and the antigen-binding portion thereof, comprise the amino acid sequences of:
 (a) SEQ ID NOs: 5-10 or
 (b) SEQ ID NOs: 13-18.

2. The nucleic acid according to claim 1, wherein the TCR, and the antigen-binding portion thereof, comprise the amino acid sequences of:
 (a) SEQ ID NOs: 11-12 or
 (b) SEQ ID NOs: 19-20.

3. The nucleic acid according to claim 1, wherein the TCR, and the antigen-binding portion thereof, further comprise the amino acid sequences of:
 (a) SEQ ID NO: 45, wherein
  (i) X at position 48 is Thr or Cys;
  (ii) X at position 112 is Ser, Gly, Ala, Val, Leu, Ile, Pro, Phe, Met, or Trp;
  (iii) X at position 114 is Met, Gly, Ala, Val, Leu, Ile, Pro, Phe, Met, or Trp; and
  (iv) X at position 115 is Gly, Ala, Val, Leu, Ile, Pro, Phe, Met, or Trp; and
 (b) SEQ ID NO: 46, wherein X at position 57 is Ser or Cys.

4. The nucleic acid according to claim 1, wherein the TCR, and the antigen-binding portion thereof, comprise the amino acid sequences of:
 (a) SEQ ID NOs: 51-52 or
 (b) SEQ ID NOs: 53-54.

5. An isolated or purified nucleic acid comprising a nucleotide sequence encoding a polypeptide, wherein the polypeptide comprises the amino acid sequences of:
 (a) SEQ ID NOs: 5-10 or
 (b) SEQ ID NOs: 13-18.

6. The nucleic acid according to claim 5, wherein the polypeptide comprises the amino acid sequence of:
 (a) SEQ ID NOs: 11-12 or
 (b) SEQ ID NOs: 19-20.

7. The nucleic acid according to claim 5, wherein the polypeptide further comprises the amino acid sequences of:
 (a) SEQ ID NO: 45, wherein
  (i) X at position 48 is Thr or Cys;
  (ii) X at position 112 is Ser, Gly, Ala, Val, Leu, Ile, Pro, Phe, Met, or Trp;
  (iii) X at position 114 is Met, Gly, Ala, Val, Leu, Ile, Pro, Phe, Met, or Trp; and
  (iv) X at position 115 is Gly, Ala, Val, Leu, Ile, Pro, Phe, Met, or Trp; and
 (b) SEQ ID NO: 46, wherein X at position 57 is Ser or Cys.

8. The nucleic acid according to claim 5, wherein the polypeptide comprises the amino acid sequences of:
 (a) SEQ ID NOs: 51-52 or
 (b) SEQ ID NOs: 53-54.

9. An isolated or purified nucleic acid comprising a nucleotide sequence encoding a protein, wherein the protein comprises:
 (a) a first polypeptide chain comprising the amino acid sequences of SEQ ID NOs: 5-7 and a second polypeptide chain comprising the amino acid sequences of SEQ ID NOs: 8-10 or
 (b) a first polypeptide chain comprising the amino acid sequences of SEQ ID NOs: 13-15 and a second polypeptide chain comprising the amino acid sequences of SEQ ID NOs: 16-18.

10. The nucleic acid of claim 9, wherein the protein comprises:
 (a) a first polypeptide chain comprising the amino acid sequence of SEQ ID NO: 11 and a second polypeptide chain comprising the amino acid sequence of SEQ ID NO: 12 or
 (b) a first polypeptide chain comprising the amino acid sequence of SEQ ID NO: 19 and a second polypeptide chain comprising the amino acid sequence of SEQ ID NO: 20.

11. The nucleic acid of claim 9, wherein:
 (a) the first polypeptide chain further comprises the amino acid sequence of SEQ ID NO: 45, wherein
  (i) X at position 48 is Thr or Cys;
  (ii) X at position 112 is Ser, Gly, Ala, Val, Leu, Ile, Pro, Phe, Met, or Trp;
  (iii) X at position 114 is Met, Gly, Ala, Val, Leu, Ile, Pro, Phe, Met, or Trp; and
  (iv) X at position 115 is Gly, Ala, Val, Leu, Ile, Pro, Phe, Met, or Trp; and
 (b) the second polypeptide chain further comprises the amino acid sequence of SEQ ID NO: 46, wherein X at position 57 is Ser or Cys.

12. The nucleic acid according to claim 9, wherein the protein comprises:
 (a) a first polypeptide chain comprising the amino acid sequence of SEQ ID NO: 51 and a second polypeptide chain comprising the amino acid sequence of SEQ ID NO: 52 or (b) a first polypeptide chain comprising the amino acid sequence of SEQ ID NO: 53 and a second polypeptide chain comprising the amino acid sequence of SEQ ID NO: 54.

13. A recombinant expression vector comprising the nucleic acid of claim 1.

14. A host cell comprising the recombinant expression vector of claim 13.

15. A population of cells comprising at least one host cell of claim 14.

16. A pharmaceutical composition comprising the population of cells of claim 15 and a pharmaceutically acceptable carrier.

* * * * *

SEQUENCE LISTING

<160> NUMBER OF SEQ ID NOS: 82

<210> SEQ ID NO 1
<211> LENGTH: 15
<212> TYPE: PRT
<213> ORGANISM: Homo sapiens

<400> SEQUENCE: 1

Cys Ala Val Arg Asp Arg Gly Thr Gly Gly Phe Lys Thr Ile Phe
1               5                   10                  15

<210> SEQ ID NO 2
<211> LENGTH: 14
<212> TYPE: PRT
<213> ORGANISM: Homo sapiens

<400> SEQUENCE: 2

Cys Ala Ser Ile Thr Lys Asp Arg Ala Tyr Glu Gln Tyr Phe
1               5                   10

<210> SEQ ID NO 3
<211> LENGTH: 11
<212> TYPE: PRT
<213> ORGANISM: Homo sapiens

<400> SEQUENCE: 3

Cys Ala Tyr Arg Ser Ala Ser Asp Met Arg Phe
1               5                   10

<210> SEQ ID NO 4
<211> LENGTH: 15
<212> TYPE: PRT
<213> ORGANISM: Homo sapiens

<400> SEQUENCE: 4

Cys Ala Ser Ser Pro Glu Thr Gly Gly Ile Ser Glu Gln Tyr Phe
1               5                   10                  15

<210> SEQ ID NO 5
<211> LENGTH: 6
<212> TYPE: PRT
<213> ORGANISM: Homo sapiens

<400> SEQUENCE: 5

Asp Ser Ala Ile Tyr Asn
1               5

<210> SEQ ID NO 6
<211> LENGTH: 7
<212> TYPE: PRT
<213> ORGANISM: Homo sapiens

<400> SEQUENCE: 6

Ile Gln Ser Ser Gln Arg Glu
1               5

<210> SEQ ID NO 7
<211> LENGTH: 9
<212> TYPE: PRT
<213> ORGANISM: Homo sapiens

<400> SEQUENCE: 7

Ala Val Asp Asn Phe Asn Lys Phe Tyr
1               5

```
<210> SEQ ID NO 8
<211> LENGTH: 5
<212> TYPE: PRT
<213> ORGANISM: Homo sapiens

<400> SEQUENCE: 8

Ser Gly His Thr Ala
1               5

<210> SEQ ID NO 9
<211> LENGTH: 6
<212> TYPE: PRT
<213> ORGANISM: Homo sapiens

<400> SEQUENCE: 9

Phe Gln Gly Thr Gly Ala
1               5

<210> SEQ ID NO 10
<211> LENGTH: 11
<212> TYPE: PRT
<213> ORGANISM: Homo sapiens

<400> SEQUENCE: 10

Ala Ser Ser Ser Gln Gly Gly Tyr Gly Tyr Thr
1               5                   10

<210> SEQ ID NO 11
<211> LENGTH: 129
<212> TYPE: PRT
<213> ORGANISM: Homo sapiens

<400> SEQUENCE: 11

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
                20                  25                  30

Pro Glu Gly Glu Asn Leu Val Leu Asn Cys Ser Phe Thr Asp Ser Ala
            35                  40                  45

Ile Tyr Asn Leu Gln Trp Phe Arg Gln Asp Pro Gly Lys Gly Leu Thr
50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Asp
            100                 105                 110

Asn Phe Asn Lys Phe Tyr Phe Gly Ser Gly Thr Lys Leu Asn Val Lys
        115                 120                 125

Pro

<210> SEQ ID NO 12
<211> LENGTH: 132
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X is Gly or Ala

<400> SEQUENCE: 12
```

Met Xaa Thr Arg Leu Cys Trp Ala Ala Leu Cys Leu Leu Gly Ala
1               5                   10                  15

Asp His Thr Gly Ala Gly Val Ser Gln Thr Pro Ser Asn Lys Val Thr
            20                  25                  30

Glu Lys Gly Lys Tyr Val Glu Leu Arg Cys Asp Pro Ile Ser Gly His
            35                  40                  45

Thr Ala Leu Tyr Trp Tyr Arg Gln Ser Leu Gly Gln Gly Pro Glu Phe
        50                  55                  60

Leu Ile Tyr Phe Gln Gly Thr Gly Ala Ala Asp Ser Gly Leu Pro
65                  70                  75                  80

Asn Asp Arg Phe Phe Ala Val Arg Pro Glu Gly Ser Val Ser Thr Leu
            85                  90                  95

Lys Ile Gln Arg Thr Glu Arg Gly Asp Ser Ala Val Tyr Leu Cys Ala
            100                 105                 110

Ser Ser Ser Gln Gly Gly Tyr Gly Tyr Thr Phe Gly Ser Gly Thr Arg
            115                 120                 125

Leu Thr Val Val
    130

<210> SEQ ID NO 13
<211> LENGTH: 5
<212> TYPE: PRT
<213> ORGANISM: Homo sapiens

<400> SEQUENCE: 13

Thr Thr Ser Asp Arg
1               5

<210> SEQ ID NO 14
<211> LENGTH: 7
<212> TYPE: PRT
<213> ORGANISM: Homo sapiens

<400> SEQUENCE: 14

Leu Leu Ser Asn Gly Ala Val
1               5

<210> SEQ ID NO 15
<211> LENGTH: 8
<212> TYPE: PRT
<213> ORGANISM: Homo sapiens

<400> SEQUENCE: 15

Ala Gly Ser Gly Ser Arg Leu Thr
1               5

<210> SEQ ID NO 16
<211> LENGTH: 5
<212> TYPE: PRT
<213> ORGANISM: Homo sapiens

<400> SEQUENCE: 16

Ser Gly His Val Ser
1               5

<210> SEQ ID NO 17
<211> LENGTH: 6
<212> TYPE: PRT
<213> ORGANISM: Homo sapiens

<400> SEQUENCE: 17

```
Phe Asn Tyr Glu Ala Gln
1               5

<210> SEQ ID NO 18
<211> LENGTH: 11
<212> TYPE: PRT
<213> ORGANISM: Homo sapiens

<400> SEQUENCE: 18

Ala Ser Ser Phe Asp Arg Gly Tyr Gly Tyr Thr
1               5                   10

<210> SEQ ID NO 19
<211> LENGTH: 126
<212> TYPE: PRT
<213> ORGANISM: Homo sapiens

<400> SEQUENCE: 19

Met Lys Lys Leu Leu Ala Met Ile Leu Trp Leu Gln Leu Asp Arg Leu
1               5                   10                  15

Ser Gly Glu Leu Lys Val Glu Gln Asn Pro Leu Phe Leu Ser Met Gln
            20                  25                  30

Glu Gly Lys Asn Tyr Thr Ile Tyr Cys Asn Tyr Ser Thr Thr Ser Asp
        35                  40                  45

Arg Leu Tyr Trp Tyr Arg Gln Asp Pro Gly Lys Ser Leu Glu Ser Leu
    50                  55                  60

Phe Val Leu Leu Ser Asn Gly Ala Val Lys Gln Glu Gly Arg Leu Met
65                  70                  75                  80

Ala Ser Leu Asp Thr Lys Ala Arg Leu Ser Thr Leu His Ile Thr Ala
                85                  90                  95

Ala Val His Asp Leu Ser Ala Thr Tyr Phe Cys Ala Gly Ser Gly Ser
            100                 105                 110

Arg Leu Thr Phe Gly Glu Gly Thr Gln Leu Thr Val Asn Pro
        115                 120                 125

<210> SEQ ID NO 20
<211> LENGTH: 132
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X is Gly or Ala

<400> SEQUENCE: 20

Met Xaa Thr Ser Leu Leu Cys Trp Val Val Leu Gly Phe Leu Gly Thr
1               5                   10                  15

Asp His Thr Gly Ala Gly Val Ser Gln Ser Pro Arg Tyr Lys Val Thr
            20                  25                  30

Lys Arg Gly Gln Asp Val Ala Leu Arg Cys Asp Pro Ile Ser Gly His
        35                  40                  45

Val Ser Leu Tyr Trp Tyr Arg Gln Ala Leu Gly Gln Gly Pro Glu Phe
    50                  55                  60

Leu Thr Tyr Phe Asn Tyr Glu Ala Gln Gln Asp Lys Ser Gly Leu Pro
65                  70                  75                  80

Asn Asp Arg Phe Ser Ala Glu Arg Pro Glu Gly Ser Ile Ser Thr Leu
                85                  90                  95

Thr Ile Gln Arg Thr Glu Gln Arg Asp Ser Ala Met Tyr Arg Cys Ala
            100                 105                 110
```

```
Ser Ser Phe Asp Arg Gly Tyr Gly Tyr Thr Phe Gly Ser Gly Thr Arg
        115                 120                 125

Leu Thr Val Val
    130

<210> SEQ ID NO 21
<211> LENGTH: 6
<212> TYPE: PRT
<213> ORGANISM: Homo sapiens

<400> SEQUENCE: 21

Thr Ser Glu Asn Asn Tyr
1               5

<210> SEQ ID NO 22
<211> LENGTH: 8
<212> TYPE: PRT
<213> ORGANISM: Homo sapiens

<400> SEQUENCE: 22

Gln Glu Ala Tyr Lys Gln Gln Asn
1               5

<210> SEQ ID NO 23
<211> LENGTH: 15
<212> TYPE: PRT
<213> ORGANISM: Homo sapiens

<400> SEQUENCE: 23

Ala Phe Thr Glu Leu Asn Ser Gly Gly Ser Asn Tyr Lys Leu Thr
1               5                   10                  15

<210> SEQ ID NO 24
<211> LENGTH: 5
<212> TYPE: PRT
<213> ORGANISM: Homo sapiens

<400> SEQUENCE: 24

Met Asn His Glu Tyr
1               5

<210> SEQ ID NO 25
<211> LENGTH: 6
<212> TYPE: PRT
<213> ORGANISM: Homo sapiens

<400> SEQUENCE: 25

Ser Met Asn Val Glu Val
1               5

<210> SEQ ID NO 26
<211> LENGTH: 15
<212> TYPE: PRT
<213> ORGANISM: Homo sapiens

<400> SEQUENCE: 26

Ala Ser Ser Leu Ser Gly Gly Leu Leu Arg Thr Gly Glu Leu Phe
1               5                   10                  15

<210> SEQ ID NO 27
<211> LENGTH: 138
<212> TYPE: PRT
<213> ORGANISM: Homo sapiens

<400> SEQUENCE: 27
```

Met Thr Arg Val Ser Leu Leu Trp Ala Val Val Ser Thr Cys Leu
1               5                   10                  15

Glu Ser Gly Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45

Glu Asn Asn Tyr Tyr Leu Phe Trp Tyr Lys Gln Pro Pro Ser Arg Gln
    50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Thr Ala Met Tyr Phe Cys
            100                 105                 110

Ala Phe Thr Glu Leu Asn Ser Gly Gly Ser Asn Tyr Lys Leu Thr Phe
        115                 120                 125

Gly Lys Gly Thr Leu Leu Thr Val Asn Pro
    130                 135

<210> SEQ ID NO 28
<211> LENGTH: 135
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X is Gly or Ala

<400> SEQUENCE: 28

Met Xaa Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Ser Leu Ser Gly Gly Leu Leu Arg Thr Gly Glu Leu Phe Phe Gly Glu
        115                 120                 125

Gly Ser Arg Leu Thr Val Leu
    130                 135

<210> SEQ ID NO 29
<211> LENGTH: 6
<212> TYPE: PRT
<213> ORGANISM: Homo sapiens

<400> SEQUENCE: 29

Asn Ser Ala Ser Gln Ser
1               5

<210> SEQ ID NO 30
<211> LENGTH: 6
<212> TYPE: PRT
<213> ORGANISM: Homo sapiens

<400> SEQUENCE: 30

Val Tyr Ser Ser Gly Asn
1               5

<210> SEQ ID NO 31
<211> LENGTH: 10
<212> TYPE: PRT
<213> ORGANISM: Homo sapiens

<400> SEQUENCE: 31

Val Val Asn Thr Asn Ala Gly Lys Ser Thr
1               5                   10

<210> SEQ ID NO 32
<211> LENGTH: 5
<212> TYPE: PRT
<213> ORGANISM: Homo sapiens

<400> SEQUENCE: 32

Ser Gly Asp Leu Ser
1               5

<210> SEQ ID NO 33
<211> LENGTH: 6
<212> TYPE: PRT
<213> ORGANISM: Homo sapiens

<400> SEQUENCE: 33

Tyr Tyr Asn Gly Glu Glu
1               5

<210> SEQ ID NO 34
<211> LENGTH: 15
<212> TYPE: PRT
<213> ORGANISM: Homo sapiens

<400> SEQUENCE: 34

Ala Ser Ser Gly Arg Val Thr Gly Gly Phe Tyr Asn Glu Gln Phe
1               5                   10                  15

<210> SEQ ID NO 35
<211> LENGTH: 130
<212> TYPE: PRT
<213> ORGANISM: Homo sapiens

<400> SEQUENCE: 35

Met Ile Ser Leu Arg Val Leu Leu Val Ile Leu Trp Leu Gln Leu Ser
1               5                   10                  15

Trp Val Trp Ser Gln Arg Lys Glu Val Glu Gln Asp Pro Gly Pro Phe
            20                  25                  30

Asn Val Pro Glu Gly Ala Thr Val Ala Phe Asn Cys Thr Tyr Ser Asn
        35                  40                  45

Ser Ala Ser Gln Ser Phe Phe Trp Tyr Arg Gln Asp Cys Arg Lys Glu
    50                  55                  60

Pro Lys Leu Leu Met Ser Val Tyr Ser Ser Gly Asn Glu Asp Gly Arg
65                  70                  75                  80

Phe Thr Ala Gln Leu Asn Arg Ala Ser Gln Tyr Ile Ser Leu Leu Ile
                85                  90                  95

Arg Asp Ser Lys Leu Ser Asp Ser Ala Thr Tyr Leu Cys Val Val Asn
            100                 105                 110

Thr Asn Ala Gly Lys Ser Thr Phe Gly Asp Gly Thr Thr Leu Thr Val
        115                 120                 125

Lys Pro
    130

<210> SEQ ID NO 36
<211> LENGTH: 135
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X is Gly or Ala

<400> SEQUENCE: 36

Met Xaa Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Gly Arg Val Thr Gly Gly Phe Tyr Asn Glu Gln Phe Phe Gly Pro
        115                 120                 125

Gly Thr Arg Leu Thr Val Leu
    130                 135

<210> SEQ ID NO 37
<211> LENGTH: 6
<212> TYPE: PRT
<213> ORGANISM: Homo sapiens

<400> SEQUENCE: 37

Asp Arg Gly Ser Gln Ser
1               5

<210> SEQ ID NO 38
<211> LENGTH: 6
<212> TYPE: PRT
<213> ORGANISM: Homo sapiens

<400> SEQUENCE: 38

Ile Tyr Ser Asn Gly Asp
1               5

<210> SEQ ID NO 39
<211> LENGTH: 10
<212> TYPE: PRT
<213> ORGANISM: Homo sapiens

<400> SEQUENCE: 39

```
Ala Ser Ser Gly Gly Asn Thr Pro Leu Val
1               5                   10
```

<210> SEQ ID NO 40
<211> LENGTH: 5
<212> TYPE: PRT
<213> ORGANISM: Homo sapiens

<400> SEQUENCE: 40

```
Met Asn His Glu Tyr
1               5
```

<210> SEQ ID NO 41
<211> LENGTH: 6
<212> TYPE: PRT
<213> ORGANISM: Homo sapiens

<400> SEQUENCE: 41

```
Ser Met Asn Val Glu Val
1               5
```

<210> SEQ ID NO 42
<211> LENGTH: 11
<212> TYPE: PRT
<213> ORGANISM: Homo sapiens

<400> SEQUENCE: 42

```
Ala Ser Ser Phe Gly Gly Ala Tyr Glu Gln Tyr
1               5                   10
```

<210> SEQ ID NO 43
<211> LENGTH: 131
<212> TYPE: PRT
<213> ORGANISM: Homo sapiens

<400> SEQUENCE: 43

```
Met Lys Ser Leu Arg Val Leu Val Ile Leu Trp Leu Gln Leu Ser
1               5                   10                  15

Trp Val Trp Ser Gln Gln Lys Glu Val Glu Gln Asn Ser Gly Pro Leu
                20                  25                  30

Ser Val Pro Glu Gly Ala Ile Ala Ser Leu Asn Cys Thr Tyr Ser Asp
            35                  40                  45

Arg Gly Ser Gln Ser Phe Phe Trp Tyr Arg Gln Tyr Ser Gly Lys Ser
        50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Ser
            100                 105                 110

Ser Gly Gly Asn Thr Pro Leu Val Phe Gly Lys Gly Thr Arg Leu Ser
        115                 120                 125

Val Ile Ala
    130
```

<210> SEQ ID NO 44
<211> LENGTH: 131
<212> TYPE: PRT
<213> ORGANISM: Homo sapiens
<220> FEATURE:
<221> NAME/KEY: MISC_FEATURE
<222> LOCATION: (2)..(2)

-continued

<223> OTHER INFORMATION: X is Gly or Ala

<400> SEQUENCE: 44

Met Xaa Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Ser Phe Gly Gly Ala Tyr Glu Gln Tyr Phe Gly Pro Gly Thr Arg Leu
        115                 120                 125

Thr Val Thr
    130

<210> SEQ ID NO 45
<211> LENGTH: 137
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (48)..(48)
<223> OTHER INFORMATION: X is Thr or Cys
<220> FEATURE:
<221> NAME/KEY: MISC_FEATURE
<222> LOCATION: (112)..(112)
<223> OTHER INFORMATION: X is Ser, Gly, Ala, Val, Leu, Ile, Pro, Phe,
      Met, or Trp
<220> FEATURE:
<221> NAME/KEY: MISC_FEATURE
<222> LOCATION: (114)..(114)
<223> OTHER INFORMATION: X is Met, Gly, Ala, Val, Leu, Ile, Pro, Phe,
      Met, or Trp
<220> FEATURE:
<221> NAME/KEY: MISC_FEATURE
<222> LOCATION: (115)..(115)
<223> OTHER INFORMATION: X is Gly, Ala, Val, Leu, Ile, Pro, Phe, Met, or
      Trp

<400> SEQUENCE: 45

Asp Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Xaa
        35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Xaa

Val Xaa Xaa Leu Arg Ile Leu Leu Lys Val Ala Gly Phe Asn Leu
     115             120             125

Leu Met Thr Leu Arg Leu Trp Ser Ser
130             135

<210> SEQ ID NO 46
<211> LENGTH: 173
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (57)..(57)
<223> OTHER INFORMATION: X is Ser or Cys

<400> SEQUENCE: 46

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Xaa Thr Asp Pro Gln Ala Tyr Lys
50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
        115                 120                 125

Ile Thr Ser Ala Ser Tyr Gln Gln Gly Val Leu Ser Ala Thr Ile Leu
    130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170

<210> SEQ ID NO 47
<211> LENGTH: 137
<212> TYPE: PRT
<213> ORGANISM: Mus musculus

<400> SEQUENCE: 47

Asp Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Thr
        35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr 85                  90                  95

Glu Lys Ser Phe Glu Thr Asp Met Asn Leu Asn Phe Gln Asn Leu Ser
                100                 105                 110

Val Met Gly Leu Arg Ile Leu Leu Lys Val Ala Gly Phe Asn Leu
            115                 120                 125

Leu Met Thr Leu Arg Leu Trp Ser Ser
        130                 135

<210> SEQ ID NO 48
<211> LENGTH: 173
<212> TYPE: PRT
<213> ORGANISM: Mus musculus

<400> SEQUENCE: 48

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Ser Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Gly Gly Ser Pro Lys Pro
                100                 105                 110

Val Thr Gln Asn Ile Ser Ala Glu Ala Trp Gly Arg Ala Asp Cys Gly
            115                 120                 125

Ile Thr Ser Ala Ser Tyr Gln Gln Gly Val Leu Ser Ala Thr Ile Leu
        130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170

<210> SEQ ID NO 49
<211> LENGTH: 137
<212> TYPE: PRT
<213> ORGANISM: Artificial Sequence
<220> FEATURE:
<223> OTHER INFORMATION: Synthetic

<400> SEQUENCE: 49

Asp Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Cys
        35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

```
Glu Lys Ser Phe Glu Thr Asp Met Asn Leu Asn Phe Gln Asn Leu Leu
            100                 105                 110

Val Ile Val Leu Arg Ile Leu Leu Lys Val Ala Gly Phe Asn Leu
            115                 120                 125

Leu Met Thr Leu Arg Leu Trp Ser Ser
            130                 135

<210> SEQ ID NO 50
<211> LENGTH: 173
<212> TYPE: PRT
<213> ORGANISM: Artificial Sequence
<220> FEATURE:
<223> OTHER INFORMATION: Synthetic

<400> SEQUENCE: 50

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Cys Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
        115                 120                 125

Ile Thr Ser Ala Ser Tyr Gln Gln Gly Val Leu Ser Ala Thr Ile Leu
    130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170

<210> SEQ ID NO 51
<211> LENGTH: 266
<212> TYPE: PRT
<213> ORGANISM: Artificial Sequence
<220> FEATURE:
<223> OTHER INFORMATION: Synthetic

<400> SEQUENCE: 51

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
        35                  40                  45

Ile Tyr Asn Leu Gln Trp Phe Arg Gln Asp Pro Gly Lys Gly Leu Thr
    50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
```

```
            85                  90                  95
Ala Ala Ser Gln Pro Gly Asp Ser Ala Thr Tyr Leu Cys Ala Val Asp
            100                 105                 110

Asn Phe Asn Lys Phe Tyr Phe Gly Ser Gly Thr Lys Leu Asn Val Lys
            115                 120                 125

Pro Asp Ile Gln Asn Pro Glu Pro Ala Val Tyr Gln Leu Lys Asp Pro
    130                 135                 140

Arg Ser Gln Asp Ser Thr Leu Cys Leu Phe Thr Asp Phe Asp Ser Gln
145                 150                 155                 160

Ile Asn Val Pro Lys Thr Met Glu Ser Gly Thr Phe Ile Thr Asp Lys
                165                 170                 175

Cys Val Leu Asp Met Lys Ala Met Asp Ser Lys Ser Asn Gly Ala Ile
                180                 185                 190

Ala Trp Ser Asn Gln Thr Ser Phe Thr Cys Gln Asp Ile Phe Lys Glu
                195                 200                 205

Thr Asn Ala Thr Tyr Pro Ser Ser Asp Val Pro Cys Asp Ala Thr Leu
            210                 215                 220

Thr Glu Lys Ser Phe Glu Thr Asp Met Asn Leu Asn Phe Gln Asn Leu
225                 230                 235                 240

Leu Val Ile Val Leu Arg Ile Leu Leu Leu Lys Val Ala Gly Phe Asn
                245                 250                 255

Leu Leu Met Thr Leu Arg Leu Trp Ser Ser
                260                 265

<210> SEQ ID NO 52
<211> LENGTH: 305
<212> TYPE: PRT
<213> ORGANISM: Artificial Sequence
<220> FEATURE:
<223> OTHER INFORMATION: Synthetic

<400> SEQUENCE: 52

Met Ala Thr Arg Leu Leu Cys Trp Ala Ala Leu Cys Leu Leu Gly Ala
1               5                   10                  15

Asp His Thr Gly Ala Gly Val Ser Gln Thr Pro Ser Asn Lys Val Thr
            20                  25                  30

Glu Lys Gly Lys Tyr Val Glu Leu Arg Cys Asp Pro Ile Ser Gly His
        35                  40                  45

Thr Ala Leu Tyr Trp Tyr Arg Gln Ser Leu Gly Gln Gly Pro Glu Phe
    50                  55                  60

Leu Ile Tyr Phe Gln Gly Thr Gly Ala Ala Asp Asp Ser Gly Leu Pro
65                  70                  75                  80

Asn Asp Arg Phe Phe Ala Val Arg Pro Glu Gly Ser Val Ser Thr Leu
                85                  90                  95

Lys Ile Gln Arg Thr Glu Arg Gly Asp Ser Ala Val Tyr Leu Cys Ala
            100                 105                 110

Ser Ser Ser Gln Gly Gly Tyr Gly Tyr Thr Phe Gly Ser Gly Thr Arg
            115                 120                 125

Leu Thr Val Val Glu Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Cys Thr Asp Pro
```

```
                    180                 185                 190
Gln Ala Tyr Lys Glu Ser Asn Tyr Ser Tyr Cys Leu Ser Ser Arg Leu
                195                 200                 205
Arg Val Ser Ala Thr Phe Trp His Asn Pro Arg Asn His Phe Arg Cys
    210                 215                 220
Gln Val Gln Phe His Gly Leu Ser Glu Glu Asp Lys Trp Pro Glu Gly
225                 230                 235                 240
Ser Pro Lys Pro Val Thr Gln Asn Ile Ser Ala Glu Ala Trp Gly Arg
                245                 250                 255
Ala Asp Cys Gly Ile Thr Ser Ala Ser Tyr Gln Gln Gly Val Leu Ser
            260                 265                 270
Ala Thr Ile Leu Tyr Glu Ile Leu Leu Gly Lys Ala Thr Leu Tyr Ala
        275                 280                 285
Val Leu Val Ser Thr Leu Val Val Met Ala Met Val Lys Arg Lys Asn
    290                 295                 300
Ser
305

<210> SEQ ID NO 53
<211> LENGTH: 263
<212> TYPE: PRT
<213> ORGANISM: Artificial Sequence
<220> FEATURE:
<223> OTHER INFORMATION: Synthetic

<400> SEQUENCE: 53

Met Lys Lys Leu Leu Ala Met Ile Leu Trp Leu Gln Leu Asp Arg Leu
1               5                   10                  15
Ser Gly Glu Leu Lys Val Glu Gln Asn Pro Leu Phe Leu Ser Met Gln
                20                  25                  30
Glu Gly Lys Asn Tyr Thr Ile Tyr Cys Asn Tyr Ser Thr Thr Ser Asp
            35                  40                  45
Arg Leu Tyr Trp Tyr Arg Gln Asp Pro Gly Lys Ser Leu Glu Ser Leu
        50                  55                  60
Phe Val Leu Leu Ser Asn Gly Ala Val Lys Gln Glu Gly Arg Leu Met
65                  70                  75                  80
Ala Ser Leu Asp Thr Lys Ala Arg Leu Ser Thr Leu His Ile Thr Ala
                85                  90                  95
Ala Val His Asp Leu Ser Ala Thr Tyr Phe Cys Ala Gly Ser Gly Ser
            100                 105                 110
Arg Leu Thr Phe Gly Glu Gly Thr Gln Leu Thr Val Asn Pro Asp Ile
        115                 120                 125
Gln Asn Pro Glu Pro Ala Val Tyr Gln Leu Lys Asp Pro Arg Ser Gln
130                 135                 140
Asp Ser Thr Leu Cys Leu Phe Thr Asp Phe Asp Ser Gln Ile Asn Val
145                 150                 155                 160
Pro Lys Thr Met Glu Ser Gly Thr Phe Ile Thr Asp Lys Cys Val Leu
                165                 170                 175
Asp Met Lys Ala Met Asp Ser Lys Ser Asn Gly Ala Ile Ala Trp Ser
            180                 185                 190
Asn Gln Thr Ser Phe Thr Cys Gln Asp Ile Phe Lys Glu Thr Asn Ala
        195                 200                 205
Thr Tyr Pro Ser Ser Asp Val Pro Cys Asp Ala Thr Leu Thr Glu Lys
    210                 215                 220
Ser Phe Glu Thr Asp Met Asn Leu Asn Phe Gln Asn Leu Leu Val Ile
```

```
                225                 230                 235                 240

Val Leu Arg Ile Leu Leu Leu Lys Val Ala Gly Phe Asn Leu Leu Met
                245                 250                 255

Thr Leu Arg Leu Trp Ser Ser
                260

<210> SEQ ID NO 54
<211> LENGTH: 305
<212> TYPE: PRT
<213> ORGANISM: Artificial Sequence
<220> FEATURE:
<223> OTHER INFORMATION: Synthetic

<400> SEQUENCE: 54

Met Ala Thr Ser Leu Leu Cys Trp Val Val Leu Gly Phe Leu Gly Thr
1               5                   10                  15

Asp His Thr Gly Ala Gly Val Ser Gln Ser Pro Arg Tyr Lys Val Thr
                20                  25                  30

Lys Arg Gly Gln Asp Val Ala Leu Arg Cys Asp Pro Ile Ser Gly His
                35                  40                  45

Val Ser Leu Tyr Trp Tyr Arg Gln Ala Leu Gly Gln Gly Pro Glu Phe
50                  55                  60

Leu Thr Tyr Phe Asn Tyr Glu Ala Gln Gln Asp Lys Ser Gly Leu Pro
65              70                  75                  80

Asn Asp Arg Phe Ser Ala Glu Arg Pro Glu Gly Ser Ile Ser Thr Leu
                85                  90                  95

Thr Ile Gln Arg Thr Glu Gln Arg Asp Ser Ala Met Tyr Arg Cys Ala
                100                 105                 110

Ser Ser Phe Asp Arg Gly Tyr Gly Tyr Thr Phe Gly Ser Gly Thr Arg
                115                 120                 125

Leu Thr Val Val Glu Asp Leu Arg Asn Val Thr Pro Pro Lys Val Ser
                130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Cys Thr Asp Pro
                180                 185                 190

Gln Ala Tyr Lys Glu Ser Asn Tyr Ser Tyr Cys Leu Ser Ser Arg Leu
                195                 200                 205

Arg Val Ser Ala Thr Phe Trp His Asn Pro Arg Asn His Phe Arg Cys
                210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr Gln Gln Gly Val Leu Ser
                260                 265                 270

Ala Thr Ile Leu Tyr Glu Ile Leu Leu Gly Lys Ala Thr Leu Tyr Ala
                275                 280                 285

Val Leu Val Ser Thr Leu Val Val Met Ala Met Val Lys Arg Lys Asn
                290                 295                 300

Ser
305
```

```
<210> SEQ ID NO 55
<211> LENGTH: 275
<212> TYPE: PRT
<213> ORGANISM: Artificial Sequence
<220> FEATURE:
<223> OTHER INFORMATION: Synthetic

<400> SEQUENCE: 55

Met Thr Arg Val Ser Leu Leu Trp Ala Val Val Ser Thr Cys Leu
1               5                   10                  15

Glu Ser Gly Met Ala Gln Thr Val Thr Gln Ser Gln Pro Glu Met Ser
                20                  25                  30

Val Gln Glu Ala Glu Thr Val Thr Leu Ser Cys Thr Tyr Asp Thr Ser
            35                  40                  45

Glu Asn Asn Tyr Tyr Leu Phe Trp Tyr Lys Gln Pro Pro Ser Arg Gln
50                  55                  60

Met Ile Leu Val Ile Arg Gln Glu Ala Tyr Lys Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Thr Ala Met Tyr Phe Cys
                100                 105                 110

Ala Phe Thr Glu Leu Asn Ser Gly Gly Ser Asn Tyr Lys Leu Thr Phe
            115                 120                 125

Gly Lys Gly Thr Leu Leu Thr Val Asn Pro Asp Ile Gln Asn Pro Glu
130                 135                 140

Pro Ala Val Tyr Gln Leu Lys Asp Pro Arg Ser Gln Asp Ser Thr Leu
145                 150                 155                 160

Cys Leu Phe Thr Asp Phe Asp Ser Gln Ile Asn Val Pro Lys Thr Met
                165                 170                 175

Glu Ser Gly Thr Phe Ile Thr Asp Lys Cys Val Leu Asp Met Lys Ala
                180                 185                 190

Met Asp Ser Lys Ser Asn Gly Ala Ile Ala Trp Ser Asn Gln Thr Ser
            195                 200                 205

Phe Thr Cys Gln Asp Ile Phe Lys Glu Thr Asn Ala Thr Tyr Pro Ser
210                 215                 220

Ser Asp Val Pro Cys Asp Ala Thr Leu Thr Glu Lys Ser Phe Glu Thr
225                 230                 235                 240

Asp Met Asn Leu Asn Phe Gln Asn Leu Leu Val Ile Val Leu Arg Ile
                245                 250                 255

Leu Leu Leu Lys Val Ala Gly Phe Asn Leu Leu Met Thr Leu Arg Leu
            260                 265                 270

Trp Ser Ser
        275

<210> SEQ ID NO 56
<211> LENGTH: 308
<212> TYPE: PRT
<213> ORGANISM: Artificial Sequence
<220> FEATURE:
<223> OTHER INFORMATION: Synthetic

<400> SEQUENCE: 56

Met Ala Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
                20                  25                  30
```

```
Val Thr Gly Lys Lys Leu Thr Val Thr Cys Ser Gln Asn Met Asn His
         35                  40                  45

Glu Tyr Met Ser Trp Tyr Arg Gln Asp Pro Gly Leu Gly Leu Arg Gln
 50                  55                  60

Ile Tyr Tyr Ser Met Asn Val Glu Val Thr Asp Lys Gly Asp Val Pro
 65                  70                  75                  80

Glu Gly Tyr Lys Val Ser Arg Lys Glu Lys Arg Asn Phe Pro Leu Ile
                 85                  90                  95

Leu Glu Ser Pro Ser Pro Asn Gln Thr Ser Leu Tyr Phe Cys Ala Ser
            100                 105                 110

Ser Leu Ser Gly Gly Leu Leu Arg Thr Gly Glu Leu Phe Phe Gly Glu
        115                 120                 125

Gly Ser Arg Leu Thr Val Leu Glu Asp Leu Arg Asn Val Thr Pro Pro
    130                 135                 140

Lys Val Ser Leu Phe Glu Pro Ser Lys Ala Glu Ile Ala Asn Lys Gln
145                 150                 155                 160

Lys Ala Thr Leu Val Cys Leu Ala Arg Gly Phe Phe Pro Asp His Val
                165                 170                 175

Glu Leu Ser Trp Trp Val Asn Gly Lys Glu Val His Ser Gly Val Cys
            180                 185                 190

Thr Asp Pro Gln Ala Tyr Lys Glu Ser Asn Tyr Ser Tyr Cys Leu Ser
        195                 200                 205

Ser Arg Leu Arg Val Ser Ala Thr Phe Trp His Asn Pro Arg Asn His
    210                 215                 220

Phe Arg Cys Gln Val Gln Phe His Gly Leu Ser Glu Glu Asp Lys Trp
225                 230                 235                 240

Pro Glu Gly Ser Pro Lys Pro Val Thr Gln Asn Ile Ser Ala Glu Ala
                245                 250                 255

Trp Gly Arg Ala Asp Cys Gly Ile Thr Ser Ala Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Thr Leu Val Val Met Ala Met Val Lys
    290                 295                 300

Arg Lys Asn Ser
305

<210> SEQ ID NO 57
<211> LENGTH: 267
<212> TYPE: PRT
<213> ORGANISM: Artificial Sequence
<220> FEATURE:
<223> OTHER INFORMATION: Synthetic

<400> SEQUENCE: 57

Met Ile Ser Leu Arg Val Leu Leu Val Ile Leu Trp Leu Gln Leu Ser
  1               5                  10                  15

Trp Val Trp Ser Gln Arg Lys Glu Val Glu Gln Asp Pro Gly Pro Phe
                 20                  25                  30

Asn Val Pro Glu Gly Ala Thr Val Ala Phe Asn Cys Thr Tyr Ser Asn
             35                  40                  45

Ser Ala Ser Gln Ser Phe Phe Trp Tyr Arg Gln Asp Cys Arg Lys Glu
         50                  55                  60

Pro Lys Leu Leu Met Ser Val Tyr Ser Ser Gly Asn Glu Asp Gly Arg
 65                  70                  75                  80
```

```
Phe Thr Ala Gln Leu Asn Arg Ala Ser Gln Tyr Ile Ser Leu Leu Ile
                85                  90                  95

Arg Asp Ser Lys Leu Ser Asp Ser Ala Thr Tyr Leu Cys Val Val Asn
            100                 105                 110

Thr Asn Ala Gly Lys Ser Thr Phe Gly Asp Gly Thr Thr Leu Thr Val
        115                 120                 125

Lys Pro Asp Ile Gln Asn Pro Glu Pro Ala Val Tyr Gln Leu Lys Asp
    130                 135                 140

Pro Arg Ser Gln Asp Ser Thr Leu Cys Leu Phe Thr Asp Phe Asp Ser
145                 150                 155                 160

Gln Ile Asn Val Pro Lys Thr Met Glu Ser Gly Thr Phe Ile Thr Asp
                165                 170                 175

Lys Cys Val Leu Asp Met Lys Ala Met Asp Ser Lys Ser Asn Gly Ala
            180                 185                 190

Ile Ala Trp Ser Asn Gln Thr Ser Phe Thr Cys Gln Asp Ile Phe Lys
        195                 200                 205

Glu Thr Asn Ala Thr Tyr Pro Ser Ser Asp Val Pro Cys Asp Ala Thr
    210                 215                 220

Leu Thr Glu Lys Ser Phe Glu Thr Asp Met Asn Leu Asn Phe Gln Asn
225                 230                 235                 240

Leu Leu Val Ile Val Leu Arg Ile Leu Leu Leu Lys Val Ala Gly Phe
                245                 250                 255

Asn Leu Leu Met Thr Leu Arg Leu Trp Ser Ser
                260                 265

<210> SEQ ID NO 58
<211> LENGTH: 308
<212> TYPE: PRT
<213> ORGANISM: Artificial Sequence
<220> FEATURE:
<223> OTHER INFORMATION: Synthetic

<400> SEQUENCE: 58

Met Ala Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Gly Arg Val Thr Gly Gly Phe Tyr Asn Glu Gln Phe Phe Gly Pro
        115                 120                 125

Gly Thr Arg Leu Thr Val Leu Glu Asp Leu Arg Asn Val Thr Pro Pro
    130                 135                 140

Lys Val Ser Leu Phe Glu Pro Ser Lys Ala Glu Ile Ala Asn Lys Gln
145                 150                 155                 160

Lys Ala Thr Leu Val Cys Leu Ala Arg Gly Phe Phe Pro Asp His Val
                165                 170                 175
```

```
Glu Leu Ser Trp Trp Val Asn Gly Lys Glu Val His Ser Gly Val Cys
            180                 185                 190

Thr Asp Pro Gln Ala Tyr Lys Glu Ser Asn Tyr Ser Tyr Cys Leu Ser
            195                 200                 205

Ser Arg Leu Arg Val Ser Ala Thr Phe Trp His Asn Pro Arg Asn His
    210                 215                 220

Phe Arg Cys Gln Val Gln Phe His Gly Leu Ser Glu Glu Asp Lys Trp
225                 230                 235                 240

Pro Glu Gly Ser Pro Lys Pro Val Thr Gln Asn Ile Ser Ala Glu Ala
                245                 250                 255

Trp Gly Arg Ala Asp Cys Gly Ile Thr Ser Ala Ser Tyr Gln Gln Gly
                260                 265                 270

Val Leu Ser Ala Thr Ile Leu Tyr Glu Ile Leu Leu Gly Lys Ala Thr
                275                 280                 285

Leu Tyr Ala Val Leu Val Ser Thr Leu Val Val Met Ala Met Val Lys
    290                 295                 300

Arg Lys Asn Ser
305

<210> SEQ ID NO 59
<211> LENGTH: 268
<212> TYPE: PRT
<213> ORGANISM: Artificial Sequence
<220> FEATURE:
<223> OTHER INFORMATION: Synthetic

<400> SEQUENCE: 59

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Ser
            100                 105                 110

Ser Gly Gly Asn Thr Pro Leu Val Phe Gly Lys Gly Thr Arg Leu Ser
        115                 120                 125

Val Ile Ala Asp Ile Gln Asn Pro Glu Pro Ala Val Tyr Gln Leu Lys
    130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

Asp Lys Cys Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
        195                 200                 205

Lys Glu Thr Asn Ala Thr Tyr Pro Ser Ser Asp Val Pro Cys Asp Ala
    210                 215                 220
```

```
Thr Leu Thr Glu Lys Ser Phe Glu Thr Asp Met Asn Leu Asn Phe Gln
225                 230                 235                 240

Asn Leu Leu Val Ile Val Leu Arg Ile Leu Leu Lys Val Ala Gly
            245                 250                 255

Phe Asn Leu Leu Met Thr Leu Arg Leu Trp Ser Ser
            260                 265

<210> SEQ ID NO 60
<211> LENGTH: 304
<212> TYPE: PRT
<213> ORGANISM: Artificial Sequence
<220> FEATURE:
<223> OTHER INFORMATION: Synthetic

<400> SEQUENCE: 60

Met Ala Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
            35                  40                  45

Glu Tyr Met Ser Trp Tyr Arg Gln Asp Pro Gly Leu Gly Leu Arg Gln
50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Ser Phe Gly Gly Ala Tyr Glu Gln Tyr Phe Gly Pro Gly Thr Arg Leu
        115                 120                 125

Thr Val Thr Glu Asp Leu Arg Asn Val Thr Pro Pro Lys Val Ser Leu
130                 135                 140

Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
                165                 170                 175

Trp Val Asn Gly Lys Glu Val His Ser Gly Val Cys Thr Asp Pro Gln
            180                 185                 190

Ala Tyr Lys Glu Ser Asn Tyr Ser Tyr Cys Leu Ser Ser Arg Leu Arg
        195                 200                 205

Val Ser Ala Thr Phe Trp His Asn Pro Arg Asn His Phe Arg Cys Gln
210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
                245                 250                 255

Asp Cys Gly Ile Thr Ser Ala Ser Tyr Gln Gln Gly Val Leu Ser Ala
            260                 265                 270

Thr Ile Leu Tyr Glu Ile Leu Leu Gly Lys Ala Thr Leu Tyr Ala Val
        275                 280                 285

Leu Val Ser Thr Leu Val Val Met Ala Met Val Lys Arg Lys Asn Ser
290                 295                 300

<210> SEQ ID NO 61
<211> LENGTH: 142
```

<212> TYPE: PRT
<213> ORGANISM: Homo sapiens

<400> SEQUENCE: 61

```
Pro Asn Ile Gln Asn Pro Asp Pro Ala Val Tyr Gln Leu Arg Asp Ser
1               5                   10                  15
Lys Ser Ser Asp Lys Ser Val Cys Leu Phe Thr Asp Phe Asp Ser Gln
            20                  25                  30
Thr Asn Val Ser Gln Ser Lys Asp Ser Asp Val Tyr Ile Thr Asp Lys
        35                  40                  45
Thr Val Leu Asp Met Arg Ser Met Asp Phe Lys Ser Asn Ser Ala Val
    50                  55                  60
Ala Trp Ser Asn Lys Ser Asp Phe Ala Cys Ala Asn Ala Phe Asn Asn
65                  70                  75                  80
Ser Ile Ile Pro Glu Asp Thr Phe Phe Pro Ser Pro Glu Ser Ser Cys
                85                  90                  95
Asp Val Lys Leu Val Glu Lys Ser Phe Glu Thr Asp Thr Asn Leu Asn
            100                 105                 110
Phe Gln Asn Leu Ser Val Ile Gly Phe Arg Ile Leu Leu Leu Lys Val
        115                 120                 125
Ala Gly Phe Asn Leu Leu Met Thr Leu Arg Leu Trp Ser Ser
    130                 135                 140
```

<210> SEQ ID NO 62
<211> LENGTH: 177
<212> TYPE: PRT
<213> ORGANISM: Homo sapiens

<400> SEQUENCE: 62

```
Glu Asp Leu Asn Lys Val Phe Pro Pro Glu Val Ala Val Phe Glu Pro
1               5                   10                  15
Ser Glu Ala Glu Ile Ser His Thr Gln Lys Ala Thr Leu Val Cys Leu
            20                  25                  30
Ala Thr Gly Phe Phe Pro Asp His Val Glu Leu Ser Trp Trp Val Asn
        35                  40                  45
Gly Lys Glu Val His Ser Gly Val Ser Thr Asp Pro Gln Pro Leu Lys
    50                  55                  60
Glu Gln Pro Ala Leu Asn Asp Ser Arg Tyr Cys Leu Ser Ser Arg Leu
65                  70                  75                  80
Arg Val Ser Ala Thr Phe Trp Gln Asn Pro Arg Asn His Phe Arg Cys
                85                  90                  95
Gln Val Gln Phe Tyr Gly Leu Ser Glu Asn Asp Glu Trp Thr Gln Asp
            100                 105                 110
Arg Ala Lys Pro Val Thr Gln Ile Val Ser Ala Glu Ala Trp Gly Arg
        115                 120                 125
Ala Asp Cys Gly Phe Thr Ser Val Ser Tyr Gln Gln Gly Val Leu Ser
    130                 135                 140
Ala Thr Ile Leu Tyr Glu Ile Leu Leu Gly Lys Ala Thr Leu Tyr Ala
145                 150                 155                 160
Val Leu Val Ser Ala Leu Val Leu Met Ala Met Val Lys Arg Lys Asp
                165                 170                 175
Phe
```

<210> SEQ ID NO 63
<211> LENGTH: 178
<212> TYPE: PRT

<213> ORGANISM: Homo sapiens

<400> SEQUENCE: 63

Asp Leu Lys Asn Val Phe Pro Pro Glu Val Ala Val Phe Glu Pro Ser
1               5                   10                  15
Glu Ala Glu Ile Ser His Thr Gln Lys Ala Thr Leu Val Cys Leu Ala
            20                  25                  30
Thr Gly Phe Tyr Pro Asp His Val Glu Leu Ser Trp Trp Val Asn Gly
        35                  40                  45
Lys Glu Val His Ser Gly Val Ser Thr Asp Pro Gln Pro Leu Lys Glu
    50                  55                  60
Gln Pro Ala Leu Asn Asp Ser Arg Tyr Cys Leu Ser Ser Arg Leu Arg
65                  70                  75                  80
Val Ser Ala Thr Phe Trp Gln Asn Pro Arg Asn His Phe Arg Cys Gln
                85                  90                  95
Val Gln Phe Tyr Gly Leu Ser Glu Asn Asp Glu Trp Thr Gln Asp Arg
            100                 105                 110
Ala Lys Pro Val Thr Gln Ile Val Ser Ala Glu Ala Trp Gly Arg Ala
        115                 120                 125
Asp Cys Gly Phe Thr Ser Glu Ser Tyr Gln Gln Gly Val Leu Ser Ala
    130                 135                 140
Thr Ile Leu Tyr Glu Ile Leu Leu Gly Lys Ala Thr Leu Tyr Ala Val
145                 150                 155                 160
Leu Val Ser Ala Leu Val Leu Met Ala Met Val Lys Arg Lys Asp Ser
                165                 170                 175
Arg Gly

<210> SEQ ID NO 64
<211> LENGTH: 388
<212> TYPE: DNA
<213> ORGANISM: Artificial Sequence
<220> FEATURE:
<223> OTHER INFORMATION: Synthetic

<400> SEQUENCE: 64
atggagaccc tcttgggcct gcttatcctt tggctgcagc tgcaatgggt gagcagcaaa     60
caggaggtga cgcagattcc tgcagctctg agtgtcccag aaggagaaaa cttggttctc    120
aactgcagtt tcactgatag cgctatttac aacctccagt ggtttaggca ggaccctggg    180
aaaggtctca catctctgtt gcttattcag tcaagtcaga gagagcaaac aagtggaaga    240
cttaatgcct cgctggataa tcatcagga cgtagtactt tatacattgc agcttctcag    300
cctggtgact cagccaccta cctctgtgct gtagacaact tcaacaaatt ttactttgga    360
tctgggacca aactcaatgt aaaaccaa                                       388

<210> SEQ ID NO 65
<211> LENGTH: 397
<212> TYPE: DNA
<213> ORGANISM: Artificial Sequence
<220> FEATURE:
<223> OTHER INFORMATION: Synthetic

<400> SEQUENCE: 65
atgggcacca ggctcctctg ctgggcagcc ctgtgcctcc tggggcaga tcacacaggt      60 gctggagtct cccagacccc cagtaacaag gtcacagaga agggaaaata tgtagagctc    120
aggtgtgatc caatttcagg tcatactgcc ctttactggt accgacaaag cctgggggcag   180

```
ggcccagagt ttctaattta cttccaaggc acgggtgcgg cagatgactc agggctgccc      240
aacgatcggt tctttgcagt caggcctgag ggatccgtct ctactctgaa gatccagcgc      300
acagagcggg gggactcagc cgtgtatctc tgtgccagca gctcacaggg gggctatggc      360
tacaccttcg gttcggggac caggttaacc gttgtag                              397
```

```
<210> SEQ ID NO 66
<211> LENGTH: 379
<212> TYPE: DNA
<213> ORGANISM: Artificial Sequence
<220> FEATURE:
<223> OTHER INFORMATION: Synthetic

<400> SEQUENCE: 66
atgaagaagc tactagcaat gattctgtgg cttcaactag accggttaag tggagagctg       60
aaagtggaac aaaaccctct gttcctgagc atgcaggagg gaaaaaacta taccatctac      120
tgcaattatt caaccacttc agacagactg tattggtaca ggcaggatcc tgggaaaagt      180
ctggaatctc tgtttgtgtt gctatcaaat ggagcagtga agcaggaggg acgattaatg      240
gcctcacttg ataccaaagc ccgtctcagc accctccaca tcacagctgc cgtgcatgac      300
ctctctgcca cctacttctg tgccggaagt ggctctaggt tgacctttgg ggaaggaaca      360
cagctcacag tgaatcctg                                                   379
```

```
<210> SEQ ID NO 67
<211> LENGTH: 397
<212> TYPE: DNA
<213> ORGANISM: Artificial Sequence
<220> FEATURE:
<223> OTHER INFORMATION: Synthetic

<400> SEQUENCE: 67
atgggcacca gtctcctatg ctgggtggtc ctgggtttcc tagggacaga tcacacaggt       60
gctggagtct cccagtctcc caggtacaaa gtcacaaaga ggggacagga tgtagctctc      120
aggtgtgatc caatttcggg tcatgtatcc ctttattggt accgacaggc cctggggcag      180
ggcccagagt ttctgactta cttcaattat gaagcccaac aagacaaatc agggctgccc      240
aatgatcggt tctctgcaga gaggcctgag ggatccatct ccactctgac gatccagcgc      300
acagagcagc gggactcggc catgtatcgc tgtgccagca gctttgacag gggctatggc      360
tacaccttcg gttcggggac caggttaacc gttgtag                              397
```

```
<210> SEQ ID NO 68
<211> LENGTH: 415
<212> TYPE: DNA
<213> ORGANISM: Artificial Sequence
<220> FEATURE:
<223> OTHER INFORMATION: Synthetic

<400> SEQUENCE: 68
atgacacgag ttagcttgct gtgggcagtc gtggtctcca cctgtcttga atccggcatg       60
gcccagacag tcactcagtc tcaaccagag atgtctgtgc aggaggcaga gactgtgacc      120
ctgagttgca catatgacac cagtgagaat aattattatt tgttctggta caagcagcct      180
cccagcaggc agatgattct cgttattcgc caagaagctt ataagcaaca gaatgcaacg      240
gagaatcgtt tctctgtgaa cttccagaaa gcagccaaat ccttcagtct caagatctca      300
gactcacagc tggggacac tgcgatgtat ttctgtgctt tcacggaact aaatagtgga      360
ggtagcaact ataaactgac atttggaaaa ggaactctct taaccgtgaa tccaa           415
```

<210> SEQ ID NO 69
<211> LENGTH: 406
<212> TYPE: DNA
<213> ORGANISM: Artificial Sequence
<220> FEATURE:
<223> OTHER INFORMATION: Synthetic

<400> SEQUENCE: 69

```
atgggccccc agctccttgg ctatgtggtc ctttgccttc taggagcagg cccctggaa      60
gcccaagtga cccagaaccc aagatacctc atcacagtga ctggaaagaa gttaacagtg    120
acttgttctc agaatatgaa ccatgagtat atgtcctggt atcgacaaga cccagggctg    180
ggcttaaggc agatctacta ttcaatgaat gttgaggtga ctgataaggg agatgttcct    240
gaagggtaca aagtctctcg aaaagagaag aggaatttcc ccctgatcct ggagtcgccc    300
agccccaacc agacctctct gtacttctgt gccagcagtc tatccggggg actactcagg    360
accggggagc tgttttttgg agaaggctct aggctgaccg tactgg                   406
```

<210> SEQ ID NO 70
<211> LENGTH: 391
<212> TYPE: DNA
<213> ORGANISM: Artificial Sequence
<220> FEATURE:
<223> OTHER INFORMATION: Synthetic

<400> SEQUENCE: 70

```
atgatatcct tgagagtttt actggtgatc ctgtggcttc agttaagctg ggtttggagc     60
caacggaagg aggtggagca ggatcctgga cccttcaatg ttccagaggg agccactgtc    120
gctttcaact gtacttacag caacagtgct tctcagtctt tcttctggta cagacaggat    180
tgcaggaaag aacctaagtt gctgatgtcc gtatactcca gtggtaatga agatggaagg    240
tttacagcac agctcaatag agccagccag tatatttccc tgctcatcag agactccaag    300
ctcagtgatt cagccaccta cctctgtgtg gtgaacacca atgcaggcaa atcaaccttt    360
ggggatggga ctacgctcac tgtgaagcca a                                   391
```

<210> SEQ ID NO 71
<211> LENGTH: 406
<212> TYPE: DNA
<213> ORGANISM: Artificial Sequence
<220> FEATURE:
<223> OTHER INFORMATION: Synthetic

<400> SEQUENCE: 71

```
atgggcttca ggctcctctg ctgtgtggcc ttttgtctcc tgggagcagg cccagtggat     60
tctggagtca cacaaacccc aaagcacctg atcacagcaa ctggacagcg agtgacgctg    120
agatgctccc ctaggtctgg agacctctct gtgtactggt accaacagag cctggaccag    180
ggcctccagt tcctcattca gtattataat ggagaagaga gagcaaaagg aaacattctt    240
gaacgattct ccgcacaaca gttccctgac ttgcactctg aactaaacct gagctctctg    300
gagctggggg actcagcttt gtatttctgt gccagcagcg cagggtgac aggggggcttc    360
tacaatgagc agttcttcgg gccagggaca cggctcaccg tgctag                   406
```

<210> SEQ ID NO 72
<211> LENGTH: 394
<212> TYPE: DNA
<213> ORGANISM: Artificial Sequence
<220> FEATURE:

<223> OTHER INFORMATION: Synthetic

<400> SEQUENCE: 72

| | |
|---|---|
| atgaaatcct tgagagtttt actagtgatc ctgtggcttc agttgagctg ggtttggagc | 60 |
| caacagaagg aggtggagca gaattctgga cccctcagtg ttccagaggg agccattgcc | 120 |
| tctctcaact gcacttacag tgaccgaggt tcccagtcct tcttctggta cagacaatat | 180 |
| tctgggaaaa gccctgagtt gataatgttc atatactcca atggtgacaa agaagatgga | 240 |
| aggtttacag cacagctcaa taaagccagc cagtatgttt ctctgctcat cagagactcc | 300 |
| cagcccagtg attcagccac ctacctctgt gcctcgtcgg gaggaaacac acctcttgtc | 360 |
| tttggaaagg cacaagact ttctgtgatt gcaa | 394 |

<210> SEQ ID NO 73
<211> LENGTH: 394
<212> TYPE: DNA
<213> ORGANISM: Artificial Sequence
<220> FEATURE:
<223> OTHER INFORMATION: Synthetic

<400> SEQUENCE: 73

| | |
|---|---|
| atgggccccc agctccttgg ctatgtggtc ctttgccttc taggagcagg cccctggaa | 60 |
| gcccaagtga cccagaaccc aagatacctc atcacagtga ctggaaagaa gttaacagtg | 120 |
| acttgttctc agaatatgaa ccatgagtat atgtcctggt atcgacaaga cccagggctg | 180 |
| ggcttaaggc agatctacta ttcaatgaat gttgaggtga ctgataaggg agatgttcct | 240 |
| gaagggtaca agtctctcg aaaagagaag aggaatttcc ccctgatcct ggagtcgccc | 300 |
| agccccaacc agacctctct gtacttctgt gccagcagtt ttggtggggc ctacgagcag | 360 |
| tacttcgggc cgggcaccag gctcacggtc acag | 394 |

<210> SEQ ID NO 74
<211> LENGTH: 314
<212> TYPE: PRT
<213> ORGANISM: Homo sapiens

<400> SEQUENCE: 74

Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
            20                  25                  30

Thr Glu Glu Gln Glu Ala Ala Ser Ser Ser Thr Leu Val Glu Val
        35                  40                  45

Thr Leu Gly Glu Val Pro Ala Ala Glu Ser Pro Asp Pro Pro Gln Ser
    50                  55                  60

Pro Gln Gly Ala Ser Ser Leu Pro Thr Thr Met Asn Tyr Pro Leu Trp
65                  70                  75                  80

Ser Gln Ser Tyr Glu Asp Ser Ser Asn Gln Glu Glu Glu Gly Pro Ser
                85                  90                  95

Thr Phe Pro Asp Leu Glu Ser Glu Phe Gln Ala Ala Leu Ser Arg Lys
            100                 105                 110

Val Ala Lys Leu Val His Phe Leu Leu Leu Lys Tyr Arg Ala Arg Glu
        115                 120                 125

Pro Val Thr Lys Ala Glu Met Leu Gly Ser Val Val Gly Asn Trp Gln
    130                 135                 140

Tyr Phe Phe Pro Val Ile Phe Ser Lys Ala Ser Asp Ser Leu Gln Leu
145                 150                 155                 160

```
Val Phe Gly Ile Glu Leu Met Glu Val Asp Pro Ile Gly His Val Tyr
                165                 170                 175

Ile Phe Ala Thr Cys Leu Gly Leu Ser Tyr Asp Gly Leu Leu Gly Asp
            180                 185                 190

Asn Gln Ile Met Pro Lys Thr Gly Phe Leu Ile Ile Leu Ala Ile
        195                 200                 205

Ile Ala Lys Glu Gly Asp Cys Ala Pro Glu Glu Lys Ile Trp Glu Glu
    210                 215                 220

Leu Ser Val Leu Glu Val Phe Glu Gly Arg Glu Asp Ser Ile Phe Gly
225                 230                 235                 240

Asp Pro Lys Lys Leu Leu Thr Gln Tyr Phe Val Gln Glu Asn Tyr Leu
                245                 250                 255

Glu Tyr Arg Gln Val Pro Gly Ser Asp Pro Ala Cys Tyr Glu Phe Leu
            260                 265                 270

Trp Gly Pro Arg Ala Leu Ile Glu Thr Ser Tyr Val Lys Val Leu His
        275                 280                 285

His Met Val Lys Ile Ser Gly Gly Pro Arg Ile Ser Tyr Pro Leu Leu
    290                 295                 300

His Glu Trp Ala Leu Arg Glu Gly Glu Glu
305                 310

<210> SEQ ID NO 75
<211> LENGTH: 1337
<212> TYPE: PRT
<213> ORGANISM: Homo sapiens

<400> SEQUENCE: 75

Met Asp Phe Thr Ala Gln Pro Lys Pro Ala Thr Ala Leu Cys Gly Val
1               5                   10                  15

Val Ser Ala Asp Gly Lys Ile Ala Tyr Pro Pro Gly Val Lys Glu Ile
            20                  25                  30

Thr Asp Lys Ile Thr Thr Asp Glu Met Ile Lys Arg Leu Lys Met Val
        35                  40                  45

Val Lys Thr Phe Met Asp Met Asp Gln Asp Ser Glu Asp Glu Lys Gln
    50                  55                  60

Gln Tyr Leu Pro Leu Ala Leu His Leu Ala Ser Glu Phe Phe Leu Arg
65                  70                  75                  80

Asn Pro Asn Lys Asp Val Arg Leu Leu Val Ala Cys Cys Leu Ala Asp
                85                  90                  95

Ile Phe Arg Ile Tyr Ala Pro Glu Ala Pro Tyr Thr Ser His Asp Lys
            100                 105                 110

Leu Lys Asp Ile Phe Leu Phe Ile Thr Arg Gln Leu Lys Gly Leu Glu
        115                 120                 125

Asp Thr Lys Ser Pro Gln Phe Asn Arg Tyr Phe Tyr Leu Leu Glu Asn
    130                 135                 140

Leu Ala Trp Val Lys Ser Tyr Asn Ile Cys Phe Glu Leu Glu Asp Cys
145                 150                 155                 160

Asn Glu Ile Phe Ile Gln Leu Phe Arg Thr Leu Phe Ser Val Ile Asn
                165                 170                 175

Asn Ser His Asn Lys Lys Val Gln Met His Met Leu Asp Leu Met Ser
            180                 185                 190

Ser Ile Ile Met Glu Gly Asp Gly Val Thr Gln Glu Leu Leu Asp Ser
        195                 200                 205

Ile Leu Ile Asn Leu Ile Pro Ala His Lys Asn Leu Asn Lys Gln Ser
```

-continued

```
            210                 215                 220
Phe Asp Leu Ala Lys Val Leu Lys Arg Thr Val Gln Thr Ile Glu
225                 230                 235                 240

Ala Cys Ile Ala Asn Phe Phe Asn Gln Val Leu Val Leu Gly Arg Ser
                245                 250                 255

Ser Val Ser Asp Leu Ser Glu His Val Phe Asp Leu Ile Gln Glu Leu
                260                 265                 270

Phe Ala Ile Asp Pro His Leu Leu Leu Ser Val Met Pro Gln Leu Glu
                275                 280                 285

Phe Lys Leu Lys Ser Asn Asp Gly Glu Glu Arg Leu Ala Val Val Arg
                290                 295                 300

Leu Leu Ala Lys Leu Phe Gly Ser Lys Asp Ser Asp Leu Ala Thr Gln
305                 310                 315                 320

Asn Arg Pro Leu Trp Gln Cys Phe Leu Gly Arg Phe Asn Asp Ile His
                325                 330                 335

Val Pro Val Arg Leu Glu Ser Val Lys Phe Ala Ser His Cys Leu Met
                340                 345                 350

Asn His Pro Asp Leu Ala Lys Asp Leu Thr Glu Tyr Leu Lys Val Arg
                355                 360                 365

Ser His Asp Pro Glu Glu Ala Ile Arg His Asp Val Ile Val Thr Ile
                370                 375                 380

Ile Thr Ala Ala Lys Arg Asp Leu Ala Leu Val Asn Asp Gln Leu Leu
385                 390                 395                 400

Gly Phe Val Arg Glu Arg Thr Leu Asp Lys Arg Trp Arg Val Arg Lys
                405                 410                 415

Glu Ala Met Met Gly Leu Ala Gln Leu Tyr Lys Lys Tyr Cys Leu His
                420                 425                 430

Gly Glu Ala Gly Lys Glu Ala Ala Glu Lys Val Ser Trp Ile Lys Asp
                435                 440                 445

Lys Leu Leu His Ile Tyr Tyr Gln Asn Ser Ile Asp Asp Lys Leu Leu
450                 455                 460

Val Glu Lys Ile Phe Ala Gln Tyr Leu Val Pro His Asn Leu Glu Thr
465                 470                 475                 480

Glu Glu Arg Met Lys Cys Leu Tyr Tyr Leu Tyr Ala Ser Leu Asp Pro
                485                 490                 495

Asn Ala Val Lys Ala Leu Asn Glu Met Trp Lys Cys Gln Asn Met Leu
                500                 505                 510

Arg Ser His Val Arg Glu Leu Leu Asp Leu His Lys Gln Pro Thr Ser
                515                 520                 525

Glu Ala Asn Cys Ser Ala Met Phe Gly Lys Leu Met Thr Ile Ala Lys
                530                 535                 540

Asn Leu Pro Asp Pro Gly Lys Ala Gln Asp Phe Val Lys Lys Phe Asn
545                 550                 555                 560

Gln Val Leu Gly Asp Asp Glu Lys Leu Arg Ser Gln Leu Glu Leu Leu
                565                 570                 575

Ile Ser Pro Thr Cys Ser Cys Lys Gln Ala Asp Ile Cys Val Arg Glu
                580                 585                 590

Ile Ala Arg Lys Leu Ala Asn Pro Lys Gln Pro Thr Asn Pro Phe Leu
                595                 600                 605

Glu Met Val Lys Phe Leu Leu Glu Arg Ile Ala Pro Val His Ile Asp
                610                 615                 620

Ser Glu Ala Ile Ser Ala Leu Val Lys Leu Met Asn Lys Ser Ile Glu
625                 630                 635                 640
```

```
Gly Thr Ala Asp Asp Glu Glu Gly Val Ser Pro Asp Thr Ala Ile
                645                 650                 655

Arg Ser Gly Leu Glu Leu Leu Lys Val Leu Ser Phe Thr His Pro Thr
            660                 665                 670

Ser Phe His Ser Ala Glu Thr Tyr Glu Ser Leu Leu Gln Cys Leu Arg
        675                 680                 685

Met Glu Asp Asp Lys Val Ala Glu Ala Ala Ile Gln Ile Phe Arg Asn
    690                 695                 700

Thr Gly His Lys Ile Glu Thr Asp Leu Pro Gln Ile Arg Ser Thr Leu
705                 710                 715                 720

Ile Pro Ile Leu His Gln Lys Ala Lys Arg Gly Thr Pro His Gln Ala
                725                 730                 735

Lys Gln Ala Val His Cys Ile His Ala Ile Phe Thr Asn Lys Glu Val
            740                 745                 750

Gln Leu Ala Gln Ile Phe Glu Pro Leu Ser Arg Ser Leu Asn Ala Asp
        755                 760                 765

Val Pro Glu Gln Leu Ile Thr Pro Leu Val Ser Leu Gly His Ile Ser
    770                 775                 780

Met Leu Ala Pro Asp Gln Phe Ala Ser Pro Met Lys Ser Val Val Ala
785                 790                 795                 800

Asn Phe Ile Val Lys Asp Leu Leu Met Asn Asp Arg Ser Thr Gly Glu
                805                 810                 815

Lys Asn Gly Lys Leu Trp Ser Pro Asp Glu Val Ser Pro Glu Val
            820                 825                 830

Leu Ala Lys Val Gln Ala Ile Lys Leu Leu Val Arg Trp Leu Leu Gly
        835                 840                 845

Met Lys Asn Asn Gln Ser Lys Ser Ala Asn Ser Thr Leu Arg Leu Leu
    850                 855                 860

Ser Ala Met Leu Val Ser Glu Gly Asp Leu Thr Glu Gln Lys Arg Ile
865                 870                 875                 880

Ser Lys Ser Asp Met Ser Arg Leu Arg Leu Ala Ala Gly Ser Ala Ile
                885                 890                 895

Met Lys Leu Ala Gln Glu Pro Cys Tyr His Glu Ile Ile Thr Pro Glu
            900                 905                 910

Gln Phe Gln Leu Cys Ala Leu Val Ile Asn Asp Glu Cys Tyr Gln Val
        915                 920                 925

Arg Gln Ile Phe Ala Gln Lys Leu His Lys Ala Leu Val Lys Leu Leu
    930                 935                 940

Leu Pro Leu Glu Tyr Met Ala Ile Phe Ala Leu Cys Ala Lys Asp Pro
945                 950                 955                 960

Val Lys Glu Arg Arg Ala His Ala Arg Gln Cys Leu Leu Lys Asn Ile
                965                 970                 975

Ser Ile Arg Arg Glu Tyr Ile Lys Gln Asn Pro Met Ala Thr Glu Lys
            980                 985                 990

Leu Leu Ser Leu Leu Pro Glu Tyr Val Val Pro Tyr Met Ile His Leu
        995                 1000                1005

Leu Ala His Asp Pro Asp Phe Thr Arg Ser Gln Asp Val Asp Gln
    1010                1015                1020

Leu Arg Asp Ile Lys Glu Cys Leu Trp Phe Met Leu Glu Val Leu
    1025                1030                1035

Met Thr Lys Asn Glu Asn Asn Ser His Ala Phe Met Lys Lys Met
    1040                1045                1050
```

Ala Glu Asn Ile Lys Leu Thr Arg Asp Ala Gln Ser Pro Asp Glu
    1055                1060                1065

Ser Lys Thr Asn Glu Lys Leu Tyr Thr Val Cys Asp Val Ala Leu
    1070                1075                1080

Cys Val Ile Asn Ser Lys Ser Ala Leu Cys Asn Ala Asp Ser Pro
    1085                1090                1095

Lys Asp Pro Val Leu Pro Met Lys Phe Phe Thr Gln Pro Glu Lys
    1100                1105                1110

Asp Phe Cys Asn Asp Lys Ser Tyr Ile Ser Glu Glu Thr Arg Val
    1115                1120                1125

Leu Leu Leu Thr Gly Lys Pro Lys Pro Ala Gly Val Leu Gly Ala
    1130                1135                1140

Val Asn Lys Pro Leu Ser Ala Thr Gly Arg Lys Pro Tyr Val Arg
    1145                1150                1155

Ser Thr Gly Thr Glu Thr Gly Ser Asn Ile Asn Val Asn Ser Glu
    1160                1165                1170

Leu Asn Pro Ser Thr Gly Asn Arg Ser Arg Glu Gln Ser Ser Glu
    1175                1180                1185

Ala Ala Glu Thr Gly Val Ser Glu Asn Glu Glu Asn Pro Val Arg
    1190                1195                1200

Ile Ile Ser Val Thr Pro Val Lys Asn Ile Asp Pro Val Lys Asn
    1205                1210                1215

Lys Glu Ile Asn Ser Asp Gln Ala Thr Gln Gly Asn Ile Ser Ser
    1220                1225                1230

Asp Arg Gly Lys Lys Arg Thr Val Thr Ala Ala Gly Ala Glu Asn
    1235                1240                1245

Ile Gln Gln Lys Thr Asp Glu Lys Val Asp Glu Ser Gly Pro Pro
    1250                1255                1260

Ala Pro Ser Lys Pro Arg Arg Gly Arg Arg Pro Lys Ser Glu Ser
    1265                1270                1275

Gln Gly Asn Ala Thr Lys Asn Asp Asp Leu Asn Lys Pro Ile Asn
    1280                1285                1290

Lys Gly Arg Lys Arg Ala Ala Val Gly Gln Glu Ser Pro Gly Gly
    1295                1300                1305

Leu Glu Ala Gly Asn Ala Lys Ala Pro Lys Leu Gln Asp Leu Ala
    1310                1315                1320

Lys Lys Ala Ala Pro Ala Glu Arg Gln Ile Asp Leu Gln Arg
    1325                1330                1335

<210> SEQ ID NO 76
<211> LENGTH: 2174
<212> TYPE: PRT
<213> ORGANISM: Homo sapiens

<400> SEQUENCE: 76

Met Ser Ala Ser Phe Val Pro Asn Gly Ala Ser Leu Glu Asp Cys His
1               5                   10                  15

Cys Asn Leu Phe Cys Leu Ala Asp Leu Thr Gly Ile Lys Trp Lys Lys
                20                  25                  30

Tyr Val Trp Gln Gly Pro Thr Ser Ala Pro Ile Leu Phe Pro Val Thr
            35                  40                  45

Glu Glu Asp Pro Ile Leu Ser Ser Phe Ser Arg Cys Leu Lys Ala Asp
        50                  55                  60

Val Leu Gly Val Trp Arg Arg Asp Gln Arg Pro Gly Arg Glu Leu
65                  70                  75                  80

-continued

Trp Ile Phe Trp Trp Gly Glu Asp Pro Ser Phe Ala Asp Leu Ile His
                85                  90                  95

His Asp Leu Ser Glu Glu Asp Gly Val Trp Glu Asn Gly Leu Ser
            100                 105                 110

Tyr Glu Cys Arg Thr Leu Leu Phe Lys Ala Val His Asn Leu Leu Glu
        115                 120                 125

Arg Cys Leu Met Asn Arg Asn Phe Val Arg Ile Gly Lys Trp Phe Val
    130                 135                 140

Lys Pro Tyr Glu Lys Asp Glu Lys Pro Ile Asn Lys Ser Glu His Leu
145                 150                 155                 160

Ser Cys Ser Phe Thr Phe Phe Leu His Gly Asp Ser Asn Val Cys Thr
                165                 170                 175

Ser Val Glu Ile Asn Gln His Gln Pro Val Tyr Leu Leu Ser Glu Glu
                180                 185                 190

His Ile Thr Leu Ala Gln Gln Ser Asn Ser Pro Phe Gln Val Ile Leu
            195                 200                 205

Cys Pro Phe Gly Leu Asn Gly Thr Leu Thr Gly Gln Ala Phe Lys Met
        210                 215                 220

Ser Asp Ser Ala Thr Lys Lys Leu Ile Gly Glu Trp Lys Gln Phe Tyr
225                 230                 235                 240

Pro Ile Ser Cys Cys Leu Lys Glu Met Ser Glu Glu Lys Gln Glu Asp
                245                 250                 255

Met Asp Trp Glu Asp Asp Ser Leu Ala Ala Val Glu Val Leu Val Ala
                260                 265                 270

Gly Val Arg Met Ile Tyr Pro Ala Cys Phe Val Leu Val Pro Gln Ser
            275                 280                 285

Asp Ile Pro Thr Pro Ser Pro Val Gly Ser Thr His Cys Ser Ser Ser
        290                 295                 300

Cys Leu Gly Val His Gln Val Pro Ala Ser Thr Arg Asp Pro Ala Met
305                 310                 315                 320

Ser Ser Val Thr Leu Thr Pro Pro Thr Ser Pro Glu Glu Val Gln Thr
                325                 330                 335

Val Asp Pro Gln Ser Val Gln Lys Trp Val Lys Phe Ser Ser Val Ser
            340                 345                 350

Asp Gly Phe Asn Ser Asp Ser Thr Ser His His Gly Gly Lys Ile Pro
        355                 360                 365

Arg Lys Leu Ala Asn His Val Val Asp Arg Val Trp Gln Glu Cys Asn
    370                 375                 380

Met Asn Arg Ala Gln Asn Lys Arg Lys Tyr Ser Ala Ser Ser Gly Gly
385                 390                 395                 400

Leu Cys Glu Glu Ala Thr Ala Ala Lys Val Ala Ser Trp Asp Phe Val
                405                 410                 415

Glu Ala Thr Gln Arg Thr Asn Cys Ser Cys Leu Arg His Lys Asn Leu
            420                 425                 430

Lys Ser Arg Asn Ala Gly Gln Gln Gly Gln Ala Pro Ser Leu Gly Gln
        435                 440                 445

Gln Gln Gln Ile Leu Pro Lys His Lys Thr Asn Glu Lys Gln Glu Lys
    450                 455                 460

Ser Glu Lys Pro Gln Lys Arg Pro Leu Thr Pro Phe His His Arg Val
465                 470                 475                 480

Ser Val Ser Asp Asp Val Gly Met Asp Ala Asp Ser Ala Ser Gln Arg
                485                 490                 495

```
Leu Val Ile Ser Ala Pro Asp Ser Gln Val Arg Phe Ser Asn Ile Arg
            500                 505                 510
Thr Asn Asp Val Ala Lys Thr Pro Gln Met His Gly Thr Glu Met Ala
            515                 520                 525
Asn Ser Pro Gln Pro Pro Leu Ser Pro His Pro Cys Asp Val Val
        530                 535                 540
Asp Glu Gly Val Thr Lys Thr Pro Ser Thr Pro Gln Ser Gln His Phe
545                 550                 555                 560
Tyr Gln Met Pro Thr Pro Asp Pro Leu Val Pro Ser Lys Pro Met Glu
                565                 570                 575
Asp Arg Ile Asp Ser Leu Ser Gln Ser Phe Pro Gln Tyr Gln Glu
            580                 585                 590
Ala Val Glu Pro Thr Val Tyr Val Gly Thr Ala Val Asn Leu Glu Glu
            595                 600                 605
Asp Glu Ala Asn Ile Ala Trp Lys Tyr Tyr Lys Phe Pro Lys Lys Lys
            610                 615                 620
Asp Val Glu Phe Leu Pro Pro Gln Leu Pro Ser Asp Lys Phe Lys Asp
625                 630                 635                 640
Asp Pro Val Gly Pro Phe Gly Gln Glu Ser Val Thr Ser Val Thr Glu
                645                 650                 655
Leu Met Val Gln Cys Lys Lys Pro Leu Lys Val Ser Asp Glu Leu Val
            660                 665                 670
Gln Gln Tyr Gln Ile Lys Asn Gln Cys Leu Ser Ala Ile Ala Ser Asp
            675                 680                 685
Ala Glu Gln Glu Pro Lys Ile Asp Pro Tyr Ala Phe Val Glu Gly Asp
            690                 695                 700
Glu Glu Phe Leu Phe Pro Asp Lys Lys Asp Arg Gln Asn Ser Glu Arg
705                 710                 715                 720
Glu Ala Gly Lys Lys His Lys Val Glu Asp Gly Thr Ser Ser Val Thr
                725                 730                 735
Val Leu Ser His Glu Glu Asp Ala Met Ser Leu Phe Ser Pro Ser Ile
            740                 745                 750
Lys Gln Asp Ala Pro Arg Pro Thr Ser His Ala Arg Pro Pro Ser Thr
            755                 760                 765
Ser Leu Ile Tyr Asp Ser Asp Leu Ala Val Ser Tyr Thr Asp Leu Asp
        770                 775                 780
Asn Leu Phe Asn Ser Asp Glu Asp Glu Leu Thr Pro Gly Ser Lys Lys
785                 790                 795                 800
Ser Ala Asn Gly Ser Asp Asp Lys Ala Ser Cys Lys Glu Ser Lys Thr
                805                 810                 815
Gly Asn Leu Asp Pro Leu Ser Cys Ile Ser Thr Ala Asp Leu His Lys
            820                 825                 830
Met Tyr Pro Thr Pro Ser Leu Glu Gln His Ile Met Gly Phe Ser
            835                 840                 845
Pro Met Asn Met Asn Asn Lys Glu Tyr Gly Ser Met Asp Thr Thr Pro
        850                 855                 860
Gly Gly Thr Val Leu Glu Gly Asn Ser Ser Ile Gly Ala Gln Phe
865                 870                 875                 880
Lys Ile Glu Val Asp Glu Gly Phe Cys Ser Pro Lys Pro Ser Glu Ile
                885                 890                 895
Lys Asp Phe Ser Tyr Val Tyr Lys Pro Glu Asn Cys Gln Ile Leu Val
            900                 905                 910
Gly Cys Ser Met Phe Ala Pro Leu Lys Thr Leu Pro Ser Gln Tyr Leu
```

```
                915                 920                 925
Pro Pro Ile Lys Leu Pro Glu Glu Cys Ile Tyr Arg Gln Ser Trp Thr
        930                 935                 940
Val Gly Lys Leu Glu Leu Leu Ser Ser Gly Pro Ser Met Pro Phe Ile
945                 950                 955                 960
Lys Glu Gly Asp Gly Ser Asn Met Asp Gln Glu Tyr Gly Thr Ala Tyr
                965                 970                 975
Thr Pro Gln Thr His Thr Ser Phe Gly Met Pro Pro Ser Ser Ala Pro
                980                 985                 990
Pro Ser Asn Ser Gly Ala Gly Ile Leu Pro Ser Pro Ser Thr Pro Arg
                995                 1000                1005
Phe Pro Thr Pro Arg Thr Pro Arg Thr Pro Arg Thr Pro Arg Gly
        1010                1015                1020
Ala Gly Gly Pro Ala Ser Ala Gln Gly Ser Val Lys Tyr Glu Asn
        1025                1030                1035
Ser Asp Leu Tyr Ser Pro Ala Ser Thr Pro Ser Thr Cys Arg Pro
        1040                1045                1050
Leu Asn Ser Val Glu Pro Ala Thr Val Pro Ser Ile Pro Glu Ala
        1055                1060                1065
His Ser Leu Tyr Val Asn Leu Ile Leu Ser Glu Ser Val Met Asn
        1070                1075                1080
Leu Phe Lys Asp Cys Asn Phe Asp Ser Cys Cys Ile Cys Val Cys
        1085                1090                1095
Asn Met Asn Ile Lys Gly Ala Asp Val Gly Val Tyr Ile Pro Asp
        1100                1105                1110
Pro Thr Gln Glu Ala Gln Tyr Arg Cys Thr Cys Gly Phe Ser Ala
        1115                1120                1125
Val Met Asn Arg Lys Phe Gly Asn Asn Ser Gly Leu Phe Leu Glu
        1130                1135                1140
Asp Glu Leu Asp Ile Ile Gly Arg Asn Thr Asp Cys Gly Lys Glu
        1145                1150                1155
Ala Glu Lys Arg Phe Glu Ala Leu Arg Ala Thr Ser Ala Glu His
        1160                1165                1170
Val Asn Gly Gly Leu Lys Glu Ser Glu Lys Leu Ser Asp Asp Leu
        1175                1180                1185
Ile Leu Leu Leu Gln Asp Gln Cys Thr Asn Leu Phe Ser Pro Phe
        1190                1195                1200
Gly Ala Ala Asp Gln Asp Pro Phe Pro Lys Ser Gly Val Ile Ser
        1205                1210                1215
Asn Trp Val Arg Val Glu Glu Arg Asp Cys Cys Asn Asp Cys Tyr
        1220                1225                1230
Leu Ala Leu Glu His Gly Arg Gln Phe Met Asp Asn Met Ser Gly
        1235                1240                1245
Gly Lys Val Asp Glu Ala Leu Val Lys Ser Ser Cys Leu His Pro
        1250                1255                1260
Trp Ser Lys Arg Asn Asp Val Ser Met Gln Cys Ser Gln Asp Ile
        1265                1270                1275
Leu Arg Met Leu Leu Ser Leu Gln Pro Val Leu Gln Asp Ala Ile
        1280                1285                1290
Gln Lys Lys Arg Thr Val Arg Pro Trp Gly Val Gln Gly Pro Leu
        1295                1300                1305
Thr Trp Gln Gln Phe His Lys Met Ala Gly Arg Gly Ser Tyr Gly
        1310                1315                1320
```

```
Thr Asp Glu Ser Pro Glu Pro Leu Pro Ile Pro Thr Phe Leu Leu
1325                1330                1335

Gly Tyr Asp Tyr Asp Tyr Leu Val Leu Ser Pro Phe Ala Leu Pro
1340                1345                1350

Tyr Trp Glu Arg Leu Met Leu Glu Pro Tyr Gly Ser Gln Arg Asp
1355                1360                1365

Ile Ala Tyr Val Val Leu Cys Pro Glu Asn Glu Ala Leu Leu Asn
1370                1375                1380

Gly Ala Lys Ser Phe Phe Arg Asp Leu Thr Ala Ile Tyr Glu Ser
1385                1390                1395

Cys Arg Leu Gly Gln His Arg Pro Val Ser Arg Leu Leu Thr Asp
1400                1405                1410

Gly Ile Met Arg Val Gly Ser Thr Ala Ser Lys Lys Leu Ser Glu
1415                1420                1425

Lys Leu Val Ala Glu Trp Phe Ser Gln Ala Ala Asp Gly Asn Asn
1430                1435                1440

Glu Ala Phe Ser Lys Leu Lys Leu Tyr Ala Gln Val Cys Arg Tyr
1445                1450                1455

Asp Leu Gly Pro Tyr Leu Ala Ser Leu Pro Leu Asp Ser Ser Leu
1460                1465                1470

Leu Ser Gln Pro Asn Leu Val Ala Pro Thr Ser Gln Ser Leu Ile
1475                1480                1485

Thr Pro Pro Gln Met Thr Asn Thr Gly Asn Ala Asn Thr Pro Ser
1490                1495                1500

Ala Thr Leu Ala Ser Ala Ala Ser Ser Thr Met Thr Val Thr Ser
1505                1510                1515

Gly Val Ala Ile Ser Thr Ser Val Ala Thr Ala Asn Ser Thr Leu
1520                1525                1530

Thr Thr Ala Ser Thr Ser Ser Ser Ser Ser Asn Leu Asn Ser
1535                1540                1545

Gly Val Ser Ser Asn Lys Leu Pro Ser Phe Pro Pro Phe Gly Ser
1550                1555                1560

Met Asn Ser Asn Ala Ala Gly Ser Met Ser Thr Gln Ala Asn Thr
1565                1570                1575

Val Gln Ser Gly Gln Leu Gly Gly Gln Gln Thr Ser Ala Leu Gln
1580                1585                1590

Thr Ala Gly Ile Ser Gly Glu Ser Ser Ser Leu Pro Thr Gln Pro
1595                1600                1605

His Pro Asp Val Ser Glu Ser Thr Met Asp Arg Asp Lys Val Gly
1610                1615                1620

Ile Pro Thr Asp Gly Asp Ser His Ala Val Thr Tyr Pro Pro Ala
1625                1630                1635

Ile Val Val Tyr Ile Ile Asp Pro Phe Thr Tyr Glu Asn Thr Asp
1640                1645                1650

Glu Ser Thr Asn Ser Ser Ser Val Trp Thr Leu Gly Leu Leu Arg
1655                1660                1665

Cys Phe Leu Glu Met Val Gln Thr Leu Pro Pro His Ile Lys Ser
1670                1675                1680

Thr Val Ser Val Gln Ile Ile Pro Cys Gln Tyr Leu Leu Gln Pro
1685                1690                1695

Val Lys His Glu Asp Arg Glu Ile Tyr Pro Gln His Leu Lys Ser
1700                1705                1710
```

```
Leu Ala Phe Ser Ala Phe Thr Gln Cys Arg Arg Pro Leu Pro Thr
1715                1720                1725

Ser Thr Asn Val Lys Thr Leu Thr Gly Phe Gly Pro Gly Leu Ala
1730                1735                1740

Met Glu Thr Ala Leu Arg Ser Pro Asp Arg Pro Glu Cys Ile Arg
1745                1750                1755

Leu Tyr Ala Pro Pro Phe Ile Leu Ala Pro Val Lys Asp Lys Gln
1760                1765                1770

Thr Glu Leu Gly Glu Thr Phe Gly Glu Ala Gly Gln Lys Tyr Asn
1775                1780                1785

Val Leu Phe Val Gly Tyr Cys Leu Ser His Asp Gln Arg Trp Ile
1790                1795                1800

Leu Ala Ser Cys Thr Asp Leu Tyr Gly Glu Leu Leu Glu Thr Cys
1805                1810                1815

Ile Ile Asn Ile Asp Val Pro Asn Arg Ala Arg Arg Lys Lys Ser
1820                1825                1830

Ser Ala Arg Lys Phe Gly Leu Gln Lys Leu Trp Glu Trp Cys Leu
1835                1840                1845

Gly Leu Val Gln Met Ser Ser Leu Pro Trp Arg Val Val Ile Gly
1850                1855                1860

Arg Leu Gly Arg Ile Gly His Gly Glu Leu Lys Asp Trp Ser Cys
1865                1870                1875

Leu Leu Ser Arg Arg Asn Leu Gln Ser Leu Ser Lys Arg Leu Lys
1880                1885                1890

Asp Met Cys Arg Met Cys Gly Ile Ser Ala Ala Asp Ser Pro Ser
1895                1900                1905

Ile Leu Ser Ala Cys Leu Val Ala Met Glu Pro Gln Gly Ser Phe
1910                1915                1920

Val Ile Met Pro Asp Ser Val Ser Thr Gly Ser Val Phe Gly Arg
1925                1930                1935

Ser Thr Thr Leu Asn Met Gln Thr Ser Gln Leu Asn Thr Pro Gln
1940                1945                1950

Asp Thr Ser Cys Thr His Ile Leu Val Phe Pro Thr Ser Ala Ser
1955                1960                1965

Val Gln Val Ala Ser Ala Thr Tyr Thr Thr Glu Asn Leu Asp Leu
1970                1975                1980

Ala Phe Asn Pro Asn Asn Asp Gly Ala Asp Gly Met Gly Ile Phe
1985                1990                1995

Asp Leu Leu Asp Thr Gly Asp Leu Asp Pro Asp Ile Ile Asn
2000                2005                2010

Ile Leu Pro Ala Ser Pro Thr Gly Ser Pro Val His Ser Pro Gly
2015                2020                2025

Ser His Tyr Pro His Gly Gly Asp Ala Gly Lys Gly Gln Ser Thr
2030                2035                2040

Asp Arg Leu Leu Ser Thr Glu Pro His Glu Glu Val Pro Asn Ile
2045                2050                2055

Leu Gln Gln Pro Leu Ala Leu Gly Tyr Phe Val Ser Thr Ala Lys
2060                2065                2070

Ala Gly Pro Leu Pro Asp Trp Phe Trp Ser Ala Cys Pro Gln Ala
2075                2080                2085

Gln Tyr Gln Cys Pro Leu Phe Leu Lys Ala Ser Leu His Leu His
2090                2095                2100

Val Pro Ser Val Gln Ser Asp Glu Leu Leu His Ser Lys His Ser
```

```
                  2105                2110                2115
His Pro Leu Asp Ser Asn Gln Thr Ser Asp Val Leu Arg Phe Val
        2120                2125                2130

Leu Glu Gln Tyr Asn Ala Leu Ser Trp Leu Thr Cys Asp Pro Ala
        2135                2140                2145

Thr Gln Asp Arg Arg Ser Cys Leu Pro Ile His Phe Val Val Leu
        2150                2155                2160

Asn Gln Leu Tyr Asn Phe Ile Met Asn Met Leu
        2165                2170

<210> SEQ ID NO 77
<211> LENGTH: 25
<212> TYPE: PRT
<213> ORGANISM: Homo sapiens

<400> SEQUENCE: 77

Asp Ser Leu Gln Leu Val Phe Gly Ile Glu Leu Met Lys Val Asp Pro
1               5                   10                  15

Ile Gly His Val Tyr Ile Phe Ala Thr
            20                  25

<210> SEQ ID NO 78
<211> LENGTH: 32
<212> TYPE: PRT
<213> ORGANISM: Homo sapiens

<400> SEQUENCE: 78

Met Ala Thr Glu Lys Leu Leu Ser Leu Leu Pro Glu Phe Val Val Pro
1               5                   10                  15

Tyr Met Ile Tyr Leu Leu Ala His Asp Pro Asp Phe Thr Arg Ser Gln
            20                  25                  30

<210> SEQ ID NO 79
<211> LENGTH: 25
<212> TYPE: PRT
<213> ORGANISM: Homo sapiens

<400> SEQUENCE: 79

Pro His Ile Lys Ser Thr Val Ser Val Gln Ile Ile Ser Cys Gln Tyr
1               5                   10                  15

Leu Leu Gln Pro Val Lys His Glu Asp
            20                  25

<210> SEQ ID NO 80
<211> LENGTH: 25
<212> TYPE: PRT
<213> ORGANISM: Homo sapiens

<400> SEQUENCE: 80

Asp Ser Leu Gln Leu Val Phe Gly Ile Glu Leu Met Glu Val Asp Pro
1               5                   10                  15

Ile Gly His Val Tyr Ile Phe Ala Thr
            20                  25

<210> SEQ ID NO 81
<211> LENGTH: 32
<212> TYPE: PRT
<213> ORGANISM: Homo sapiens

<400> SEQUENCE: 81

Met Ala Thr Glu Lys Leu Leu Ser Leu Leu Pro Glu Tyr Val Val Pro
```

```
1               5                   10                  15
Tyr Met Ile His Leu Leu Ala His Asp Pro Asp Phe Thr Arg Ser Gln
             20                  25                  30

<210> SEQ ID NO 82
<211> LENGTH: 25
<212> TYPE: PRT
<213> ORGANISM: Homo sapiens

<400> SEQUENCE: 82

Pro His Ile Lys Ser Thr Val Ser Val Gln Ile Ile Pro Cys Gln Tyr
1               5                   10                  15

Leu Leu Gln Pro Val Lys His Glu Asp
             20                  25
```